US010952602B2

(12) United States Patent
Kiser et al.

(10) Patent No.: US 10,952,602 B2
(45) Date of Patent: Mar. 23, 2021

(54) METHODS AND DEVICES FOR ENDOSCOPIC ACCESS TO THE HEART

(71) Applicant: Atrius Limited, Dublin (IE)

(72) Inventors: Andy Christopher Kiser, West End, NC (US); Mark Douglas Landers, Pinehurst, NC (US)

(73) Assignee: CONVEYOR CARDIOVASCULAR LIMITED, Dublin (IE)

( * ) Notice: Subject to any disclaimer, the term of this patent is extended or adjusted under 35 U.S.C. 154(b) by 7 days.

(21) Appl. No.: 15/960,017

(22) Filed: Apr. 23, 2018

(65) Prior Publication Data
US 2018/0303332 A1 Oct. 25, 2018

Related U.S. Application Data

(62) Division of application No. 12/642,137, filed on Dec. 18, 2009, now abandoned.
(Continued)

(51) Int. Cl.
*A61B 1/00* (2006.01)
*A61B 1/313* (2006.01)
(Continued)

(52) U.S. Cl.
CPC .............. *A61B 1/3137* (2013.01); *A61B 1/04* (2013.01); *A61B 1/3132* (2013.01);
(Continued)

(58) Field of Classification Search
CPC ............ A61B 1/00137; A61B 1/00089; A61B 1/00101
(Continued)

(56) References Cited

U.S. PATENT DOCUMENTS 4,817,634 A 4/1989 Holleman et al.
4,823,794 A 4/1989 Pierce
(Continued)

FOREIGN PATENT DOCUMENTS

JP H11-503646 3/1999
JP 2004-298623 A 10/2004
(Continued)

OTHER PUBLICATIONS

Aberg, H., "Atrial Fibrillation. I. A study of Atrial Thrombosis and Systemic Embolism in a Necropsy Material," 1969, Acta Med. Scand., 185:373-379.
(Continued)

*Primary Examiner* — Alexandra L Newton
*Assistant Examiner* — Rynae Boler
(74) *Attorney, Agent, or Firm* — Myers Bigel, P.A.

(57) ABSTRACT

Disclosed are devices for cardioscopic and pericardioscopic access to the heart, including direct access to the left atrium. In certain embodiments, the device may comprise an atrial portal having a configuration such that the distal end of the atrial portal can access the atrium while the proximal end of the portal can extend to outside of the subject. The devices and methods may also include a pericardioscopic portal for emplacement of the atrial portal. Also, methods for using such atrial portals and pericardial portals to perform surgery on the heart, and in some cases to directly access the left atrium, and systems (e.g., kits) comprising these portals in combination with other therapeutic devices are disclosed.

13 Claims, 34 Drawing Sheets

Related U.S. Application Data

(60) Provisional application No. 61/262,372, filed on Nov. 18, 2009, provisional application No. 61/203,173, filed on Dec. 19, 2008.

(51) Int. Cl.

| | | |
|---|---|---|
| *A61B 1/04* | (2006.01) | |
| *A61B 17/00* | (2006.01) | |
| *A61B 17/04* | (2006.01) | |
| *A61B 17/34* | (2006.01) | |
| A61B 18/14 | (2006.01) | |
| A61B 17/06 | (2006.01) | |
| A61F 2/24 | (2006.01) | |

(52) U.S. Cl.
CPC ...... *A61B 17/0057* (2013.01); *A61B 17/0401* (2013.01); *A61B 17/3421* (2013.01); *A61B 17/0485* (2013.01); *A61B 17/0487* (2013.01); *A61B 18/1477* (2013.01); *A61B 18/1492* (2013.01); *A61B 2017/00243* (2013.01); *A61B 2017/00637* (2013.01); *A61B 2017/00663* (2013.01); *A61B 2017/0404* (2013.01); *A61B 2017/0409* (2013.01); *A61B 2017/0412* (2013.01); *A61B 2017/0427* (2013.01); *A61B 2017/0437* (2013.01); *A61B 2017/0464* (2013.01); *A61B 2017/0496* (2013.01); *A61B 2017/06052* (2013.01); *A61B 2017/3425* (2013.01); *A61B 2017/3445* (2013.01); *A61B 2018/1425* (2013.01); *A61F 2/2433* (2013.01)

(58) Field of Classification Search
USPC ........................................................ 600/127
See application file for complete search history.

(56) References Cited

U.S. PATENT DOCUMENTS

| | | | |
|---|---|---|---|
| 5,013,296 A | 5/1991 | Buckberg et al. | |
| 5,327,909 A | 7/1994 | Kiser et al. | |
| 5,391,156 A | 2/1995 | Hildwein et al. | |
| 5,935,107 A | 8/1999 | Taylor et al. | |
| 5,980,455 A | 11/1999 | Daniel et al. | |
| 6,110,185 A | 8/2000 | Barra et al. | |
| 6,293,920 B1 | 9/2001 | Sweezer et al. | |
| 6,322,578 B1 | 11/2001 | Houle et al. | |
| 6,346,074 B1 | 2/2002 | Roth | |
| 6,482,171 B1 | 11/2002 | Corvi et al. | |
| 6,533,770 B1 | 3/2003 | Lepulu et al. | |
| 6,535,764 B2 | 3/2003 | Imran et al. | |
| 6,564,805 B2 | 5/2003 | Garrison et al. | |
| 6,613,069 B2 | 9/2003 | Boyd et al. | |
| 6,651,672 B2 | 11/2003 | Roth | |
| 6,679,268 B2 | 1/2004 | Stevens et al. | |
| 6,709,441 B2 | 3/2004 | Bolduc et al. | |
| 6,866,650 B2 | 3/2005 | Stevens et al. | |
| 6,878,106 B1 | 4/2005 | Herrmann | |
| 6,893,442 B2 | 5/2005 | Whayne | |
| 6,899,704 B2 | 5/2005 | Sterman et al. | |
| 6,974,436 B1 | 12/2005 | Aboul-Hosn et al. | |
| 6,994,669 B1 | 2/2006 | Gannoe et al. | |
| 7,028,692 B2 | 4/2006 | Sterman et al. | |
| 7,056,326 B2 | 6/2006 | Bolduc et al. | |
| 7,063,698 B2 | 6/2006 | Whayne et al. | |
| 7,112,211 B2 | 9/2006 | Gifford, III et al. | |
| 7,122,044 B2 | 10/2006 | Bolduc et al. | |
| 7,131,447 B2 | 11/2006 | Sterman et al. | |
| 7,213,601 B2 | 5/2007 | Stevens et al. | |
| 7,410,487 B2 | 8/2008 | Whayne | |
| 7,463,932 B2 | 12/2008 | Cawthra, Jr. | |
| 7,651,510 B2 | 1/2010 | Bolduc et al. | |
| 7,763,041 B2 | 7/2010 | Bolduc et al. | |
| 7,930,016 B1* | 4/2011 | Saadat .................. | A61B 1/0008 600/101 |
| 7,935,129 B2 | 5/2011 | Gifford, III et al. | |
| 8,182,530 B2 | 5/2012 | Huber | |
| 8,602,970 B2 | 12/2013 | Muyari et al. | |
| 2002/0002372 A1 | 1/2002 | Jahns et al. | |
| 2002/0049457 A1 | 4/2002 | Kaplan et al. | |
| 2002/0056460 A1 | 5/2002 | Boyd et al. | |
| 2003/0130713 A1* | 7/2003 | Stewart ............ | A61B 17/00234 607/119 |
| 2003/0158563 A1 | 8/2003 | McClellan et al. | |
| 2004/0077928 A1 | 4/2004 | Moriyanna | |
| 2004/0127967 A1 | 7/2004 | Osypka | |
| 2005/0075656 A1 | 4/2005 | Beaupre | |
| 2005/0107816 A1 | 5/2005 | Pingleton et al. | |
| 2006/0004388 A1 | 1/2006 | Whayne et al. | |
| 2006/0020162 A1 | 1/2006 | Whayne et al. | |
| 2006/0200124 A1 | 9/2006 | Whayne et al. | |
| 2006/0206113 A1 | 9/2006 | Whayne et al. | |
| 2006/0224153 A1* | 10/2006 | Fischell .............. | A61B 18/1492 606/41 |
| 2006/0235357 A1* | 10/2006 | Woodward ............... | A61M 1/10 604/264 |
| 2006/0235381 A1 | 10/2006 | Whayne et al. | |
| 2006/0293646 A1 | 12/2006 | Whayne et al. | |
| 2006/0293740 A1 | 12/2006 | Heil, Jr. et al. | |
| 2007/0043351 A1 | 2/2007 | Fleischman et al. | |
| 2007/0083082 A1 | 4/2007 | Kiser et al. | |
| 2007/0083225 A1 | 4/2007 | Kiser et al. | |
| 2007/0249991 A1* | 10/2007 | Whayne .............. | A61B 17/0218 604/28 |
| 2007/0250058 A1 | 10/2007 | Whayne et al. | |
| 2008/0045898 A1 | 2/2008 | Stewart et al. | |
| 2008/0114288 A1 | 5/2008 | Whayne et al. | |
| 2008/0114342 A1 | 5/2008 | Whayne et al. | |
| 2008/0114354 A1 | 5/2008 | Whayne et al. | |
| 2008/0114355 A1 | 5/2008 | Whayne et al. | |
| 2008/0243081 A1 | 10/2008 | Nance et al. | |
| 2008/0243111 A1 | 10/2008 | Gammie et al. | |
| 2008/0243119 A1 | 10/2008 | Whayne | |
| 2008/0294175 A1 | 11/2008 | Bardsley et al. | |
| 2009/0024213 A1 | 1/2009 | Raman et al. | |
| 2009/0082778 A1 | 3/2009 | Beane et al. | |

FOREIGN PATENT DOCUMENTS

| | | |
|---|---|---|
| JP | 2008-528239 | 7/2008 |
| JP | 2009-523034 A | 6/2009 |
| JP | 2010-537725 A | 12/2010 |
| WO | WO 96/32882 | 10/1996 |
| WO | WO 2006/083794 A2 | 8/2006 |
| WO | WO 2007/046860 | 4/2007 |
| WO | WO 07/127664 A1 | 11/2007 |
| WO | WO 2008/005990 A1 | 1/2008 |
| WO | WO 2008/057117 | 5/2008 |
| WO | WO 2009/029387 A1 | 3/2009 |

OTHER PUBLICATIONS

Blackshear, J. and Odell, J., "Appendage Obliteration to Reduce Stroke in Cardiac Surgical Patients With Atrial Fibrillation," 1996, Ann. Thorac. Surg., 61:755-759.

Kannel, W. et al., "Prevalence, Incidence, Prognosis, and Predisposing Conditions for Atrial Fibrillation: Population-Based Estimates," 1998, Am. J. Cardiol., 82:2N-9N.

Sandercock, P. et al., "Atrial fibrillation and stroke: prevalence in different types of stroke and influence on early and long term prognosis (Oxfordshire community stroke project)," 1992, BMJ, 305:1460-1465.

Stoddard, M. et al., "Left Atrial Appendage Thrombus Is Not Uncommon in Patients With Acute Atrial Fibrillation and a Recent Embolic Event: A Transesophageal Echocardiographic Study," 1995, J. Am. Coll. Cardiol., 25:452-459.

Wolf, P. et al., "Secular trends in the prevalence of atrial fibrillation: The Framingham Study," 1996, Am. Heart J., 131:790-795.

Abashian et al., "Effect of Ablation on Local Activation Intervals and Dominant Frequencies of Fibrillation," Computers in Cardiology, 2007; 34:781-783.

(56) References Cited

OTHER PUBLICATIONS

Beaufort-Krol et al., "Comparison of Longevity, Pacing, and Sensing Characteristics of Steroid-Eluting Epicardial Versus Conventional Endocardial Pacing Leads in Children," J. Thorac. Cardiovasc. Surg. 1999; 117:523-528.
Budde et al., "Robot-assisted 13 MHz epicardial ultrasound for endoscopic quality assessment of coronary anastomoses," Interactive Cardiovascular and Thoracic Surgery 2004; 3:616-620.
Cohen et al.. "Permanent Epicardial Pacing in Pediatric Patients Seventeen Years of Experience and 1200 Outpatient Visits," Circulation 2001; 103:2585-2590.
Covidien, web page available at http://www.autosuture.com.
Kiser et al., "Achieving Metrics during Beating Heart Ex-Maze Procedures Improve Outcomes," Heart Surg. Forum, 2008; 11(4): E237-E242.
Kiser et al., "Blunt Tracheobronchial Injuries: Treatment and Outcomes," Ann. Thorac Surg., Jun. 2001: 71 (6):2059-2065.
Kiser et al. "Evaluation of a Novel Epicardial Atrial Fibrillation Treatment System," Ann Thorac Surg., Jan. 2008; 85(1 ): 300-304.
Kiser et al., "MP8: Clinical Evaluation of the Extra-Cardiac Maze (Ex-Maze) Procedure," Innovations, 2007, vol. 2, No. 3: 129.
Kiser et al., "Presentation Number: VI3—Paracardioscopic Ex-Maze Procedure for Atrial Fibrillation," Innovations, 2008, vol. 3, No. 2: 117-118.
Kiser, "In Their Own Words—The College's Chapter Visit Program: Becoming involved in the Political Process," Bull Am Coll Surg., Oct. 2000; 85(10):19-20.
Milano et al., "Transmyocardial holmium laser revascularization: feasibility of a thoracoscopic approach," European Journal of Cardia-Thoracic Surgery 1998; 14:105-110.
Robicsek, "Minimally Invasive MIDCABG and TMLR," Ann. Thorac. Surg. 1999; Mar.; 67(3):892.
Spittell et al., "Venous Complications After Insertion of a Transvenous Pacemaker," Mayo Clin. Proc. 1992; 67(3):258-265.
Bailey et al., "Abstract 2865: Short Term Results of the Convergent Endo-Epicardial Ablation Procedure for the Treatment of Long Standing Persistent Atrial Fibrillation," Circulation, 2009; 120:S707.
Dumas et al., "Abstract 3102: Translesion Myocardial Impedance as an Indicator of Lesion Production by RF Ablation," Circulation, 2006; 114:11_654-11_655.
Dumas et al., "Myocardial electrical impedance as a predictor of the quality of RF-induced linear lesions," Physiol Meas., Oct. 2008; 29(10): 1195-1207, Epub Sep. 18, 2008.
Himel et al., "Abstract 1786: Translesion stimulation-excitation delay rapidly indicates quality lesion completeness and increased conduction path length around ablated tissue," Circulation, 2006; 114:11_352.
Himel et al., "Translesion stimulation-excitation delay indicates quality of linear lesions produced by radiofrequency ablation in rabbit hearts," Physiol. Meas., 2007, 28: 611-623.
Kiser et al., "Lung Retrieval from Non-Heart Beating Cadavers with the Use of a Rat Lung Transplant Model," J Thorac Cardiovasc Surg., Jul. 2001; 122(1 ): 18-23.
Kiser et al., "Metastatic Melanoma to the Pleural Space," Ann Thorac Surg., Oct. 2002; 74(4): 1257.
Kiser et al., "Pacemakers and Intraoperative Cardiac Interactions: Implications for Surgeons," Bull Am Coll Surg., Mar. 2000; 85(3): 18-20.
Kiser et al., "Paracardioscopic Creation of a Comprehensive Biatrial Lesion Pattern During Minimally Invasive Atrial Fibrillation Treatment," J. Am. Coll. Cardiol., Mar. 2008: 51 :A 12; 1008-115. Abstract.
Kiser et al., "Primary Percutaneous Endoscopic Button Gastrostomy: A Modification of the "Push" Technique," J. Am. Coll. Surg., Jun. 1999; 188(6): 704-706.
Kiser et al., "Spontaneous Hemopneumothorax in Women," South Med. J., Dec. 2000; 93(12): 1209-1211.
Kiser et al., "The Surgeon at Work: Subcutaneous Injection of Donor Sites for Split-Thickness Skin Grafts,"J. Am. Coll. Surg., Mar. 1996; 182(3): 265-267.
Kiser et al., "Totally Extracardiac Maze Procedure Performed on the Beating Heart," Ann Thorac Surg., Nov. 2007; 84(5): 1783-1785.
Kiser, "Paracardioscopy Provides Endoscopic Visualization of the Heart," Innovations, Jul./Aug. 2009; vol. 4, No. 4: 233-235.
Blackshear et al., "Appendage obliteration to reduce stroke in cardiac surgical patients with atrial fibrillation," Ann Thorac Surg., Feb. 1996; 61(2):755-9.
Edgerton et al., "Total thoracoscopic ablation of atrial fibrillation using the Dallas lesion set, partial autonomic denervation, and left atrial appendectomy," Operative Techniques in Thorac. and Cardiovasc Surg., 2009;14:224-242.
Rodriguez et al., "Minimally invasive bi-atrial cryomaze operation for atrial fibrillation," Operative Techniques in Thorac and Cardiovasc Surg., 2009;14:208-223.
Supplementary Search Report, EP 09 83 2837, dated Jan. 25, 2013.
Office Action corresponding to Canadian Patent Application No. 2,751,814; dated Aug. 16, 2013; 3 pages.
Notice of Reason for Rejection, Japanese Patent Application No. 2015-113914, dated May 10, 2016, 4 pages.

\* cited by examiner

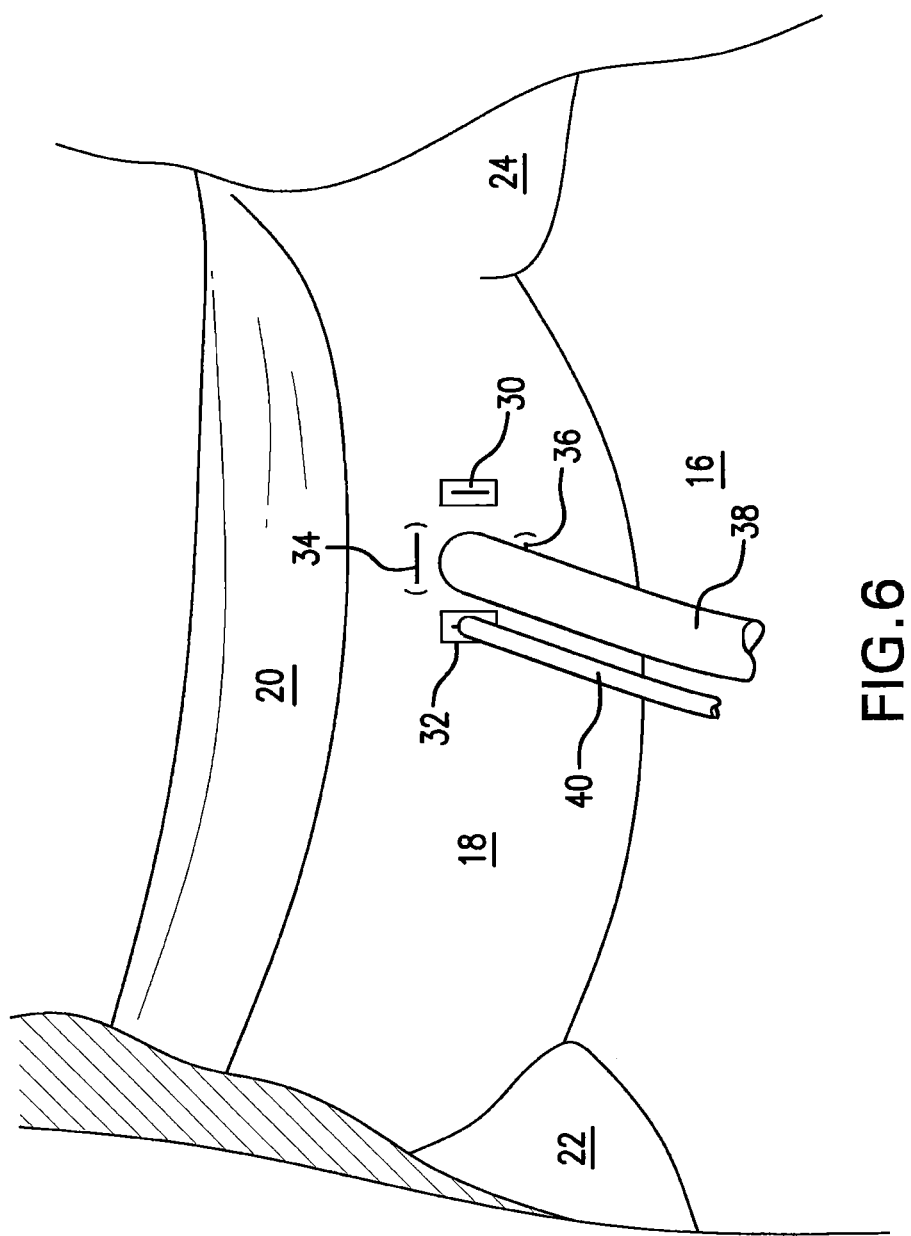

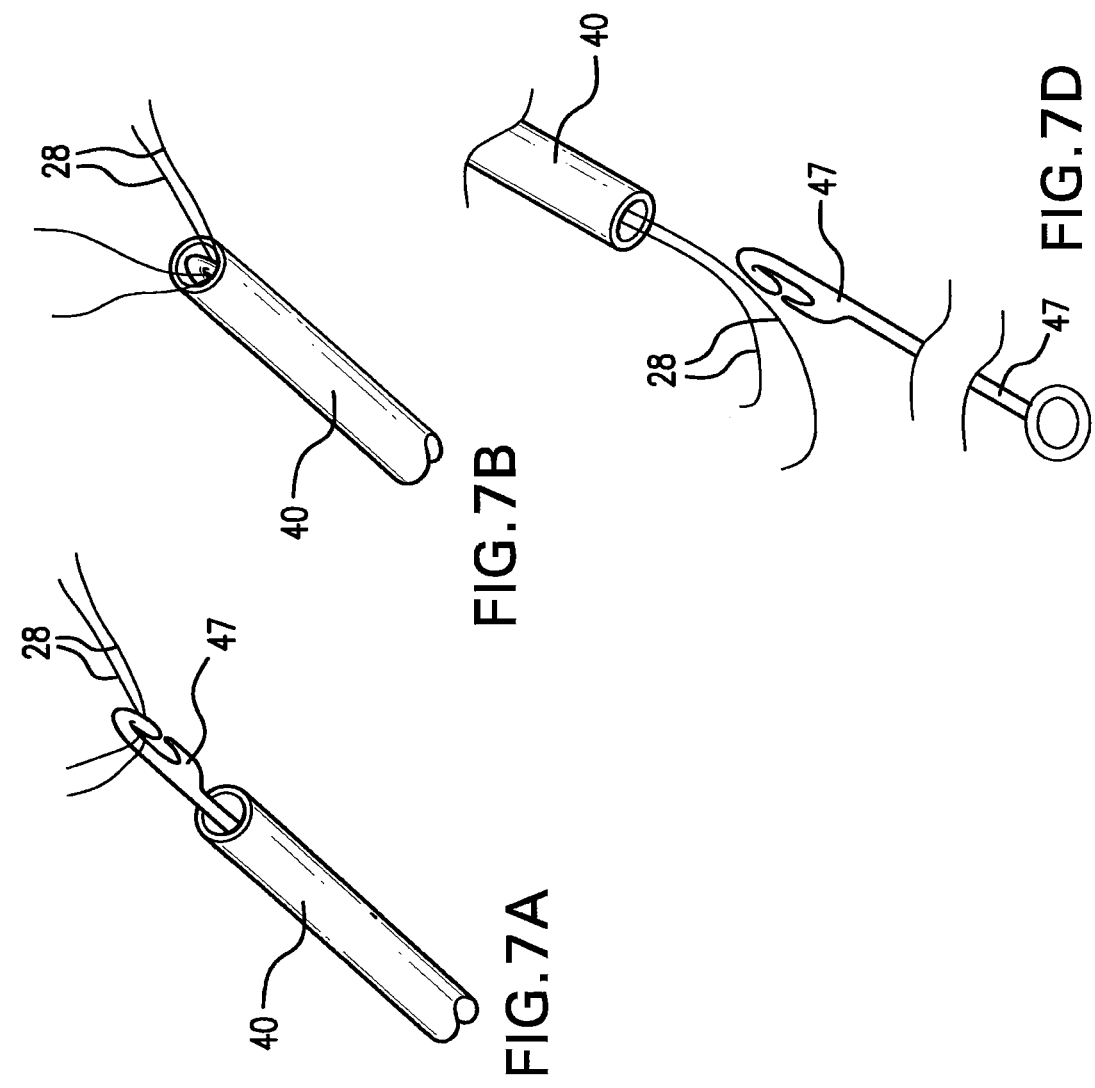

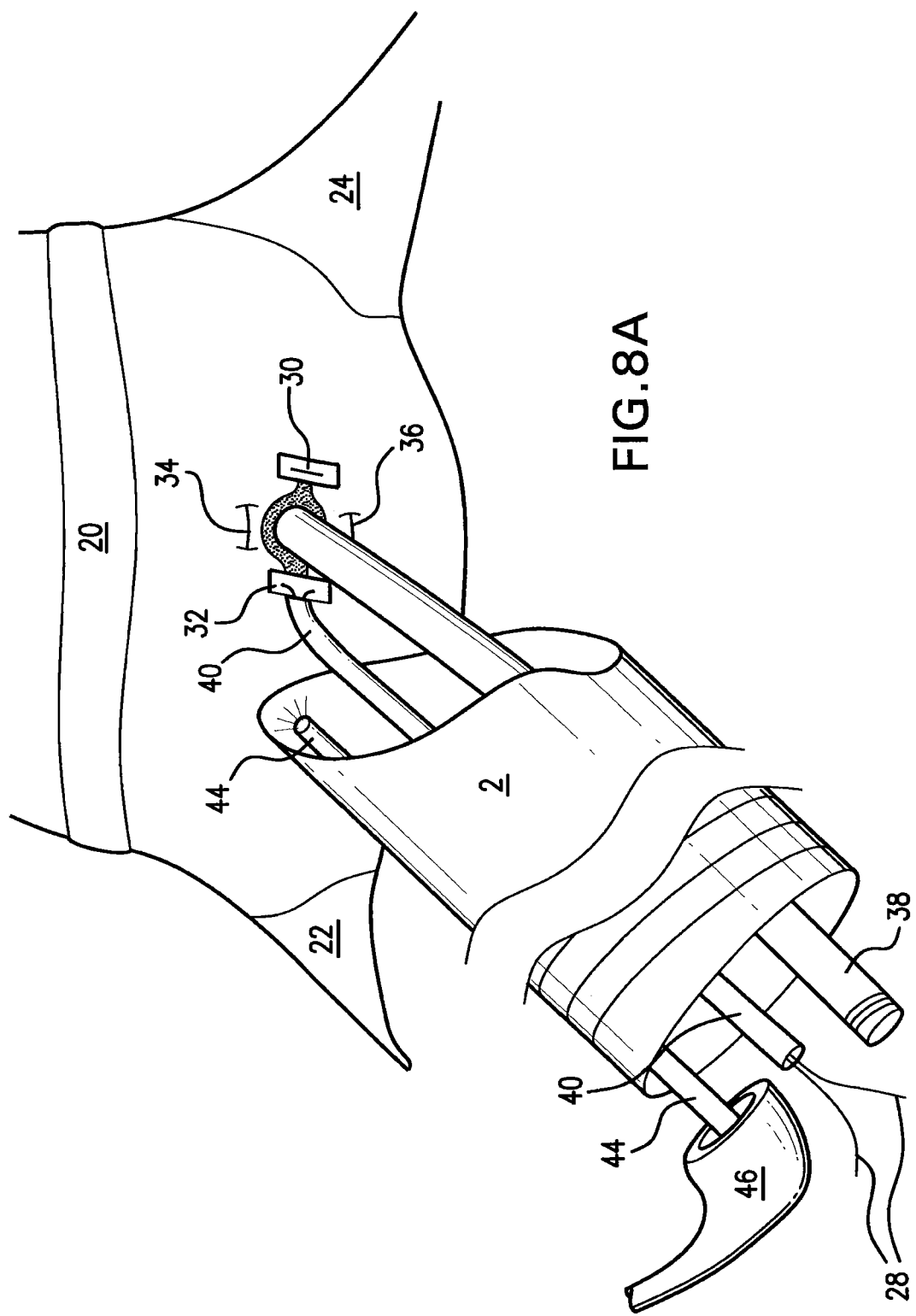

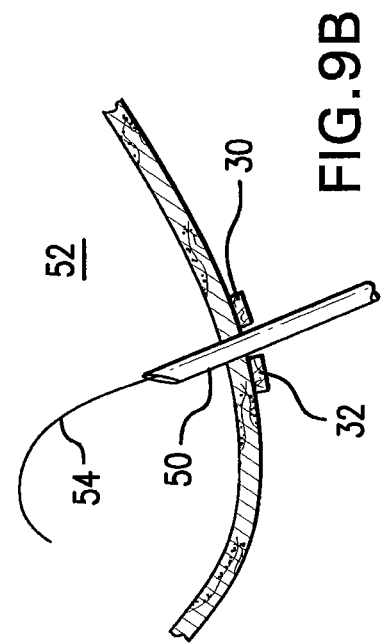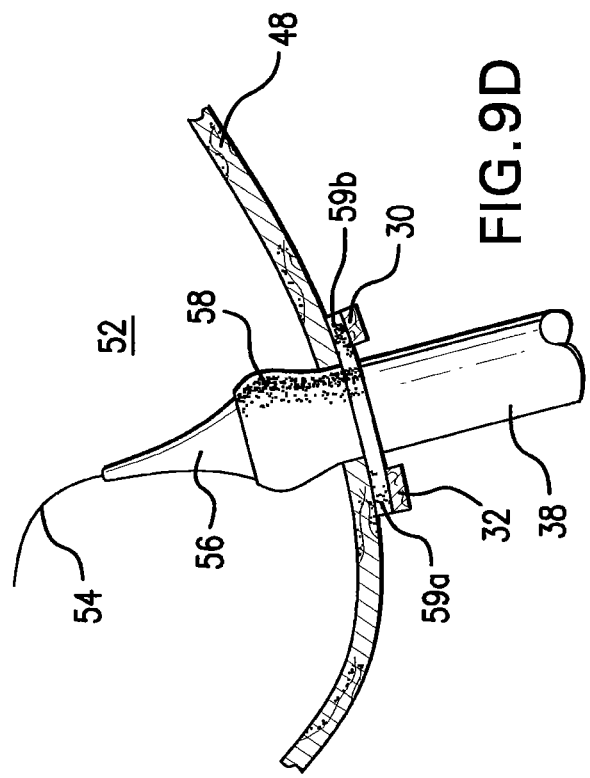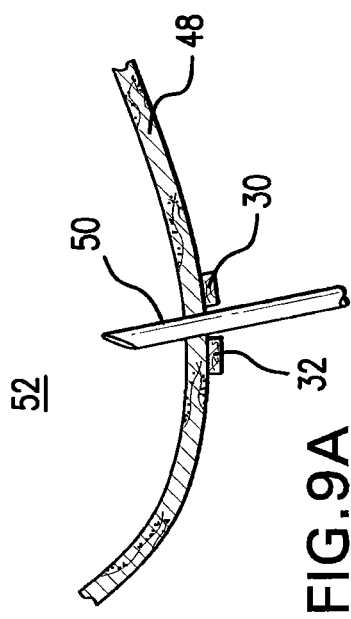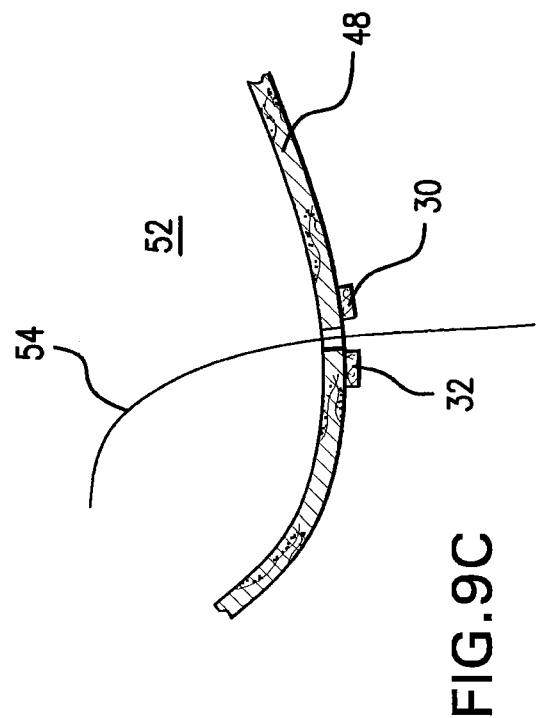

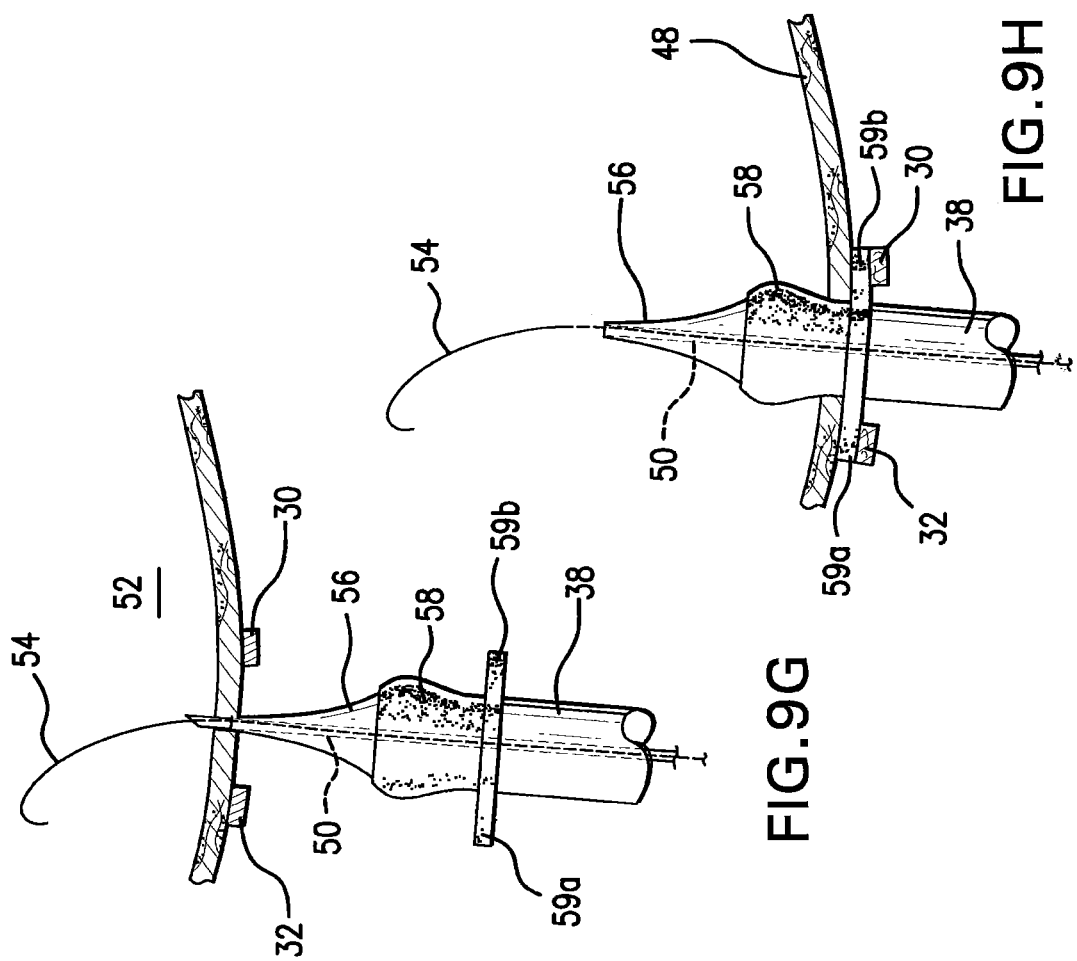
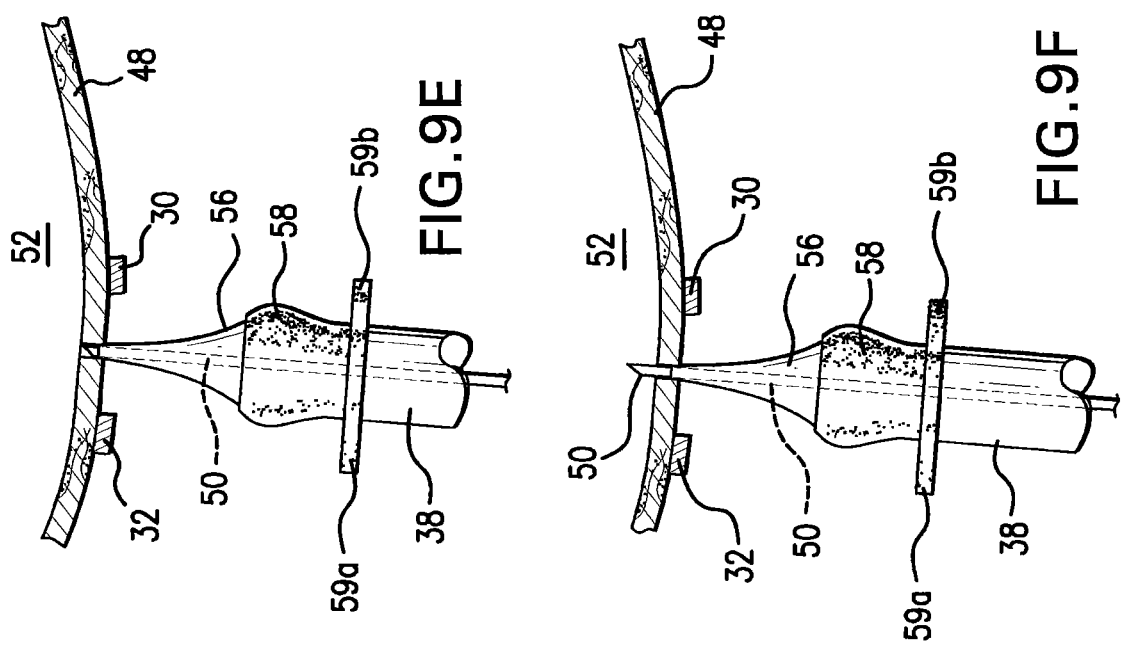

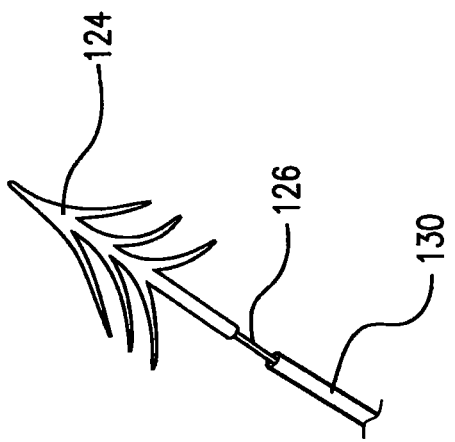
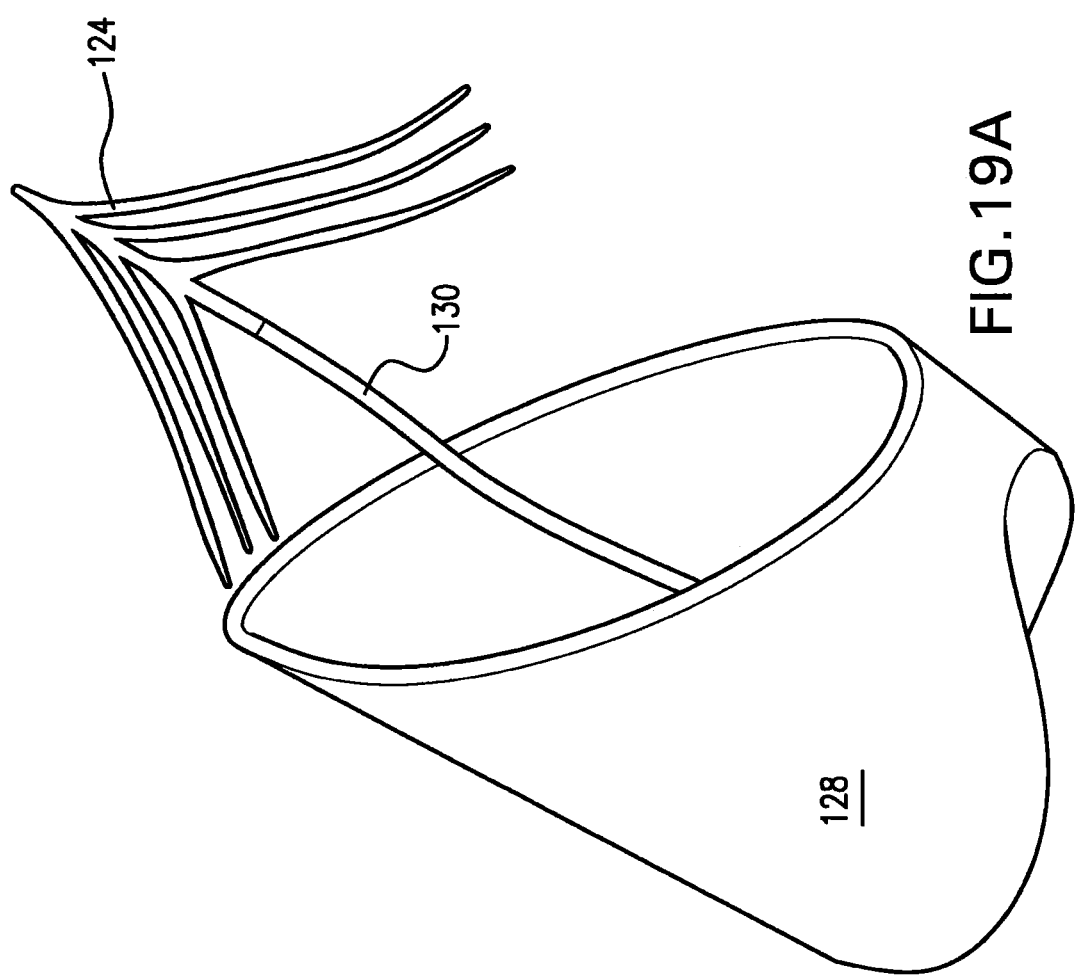
FIG. 19B
FIG. 19A

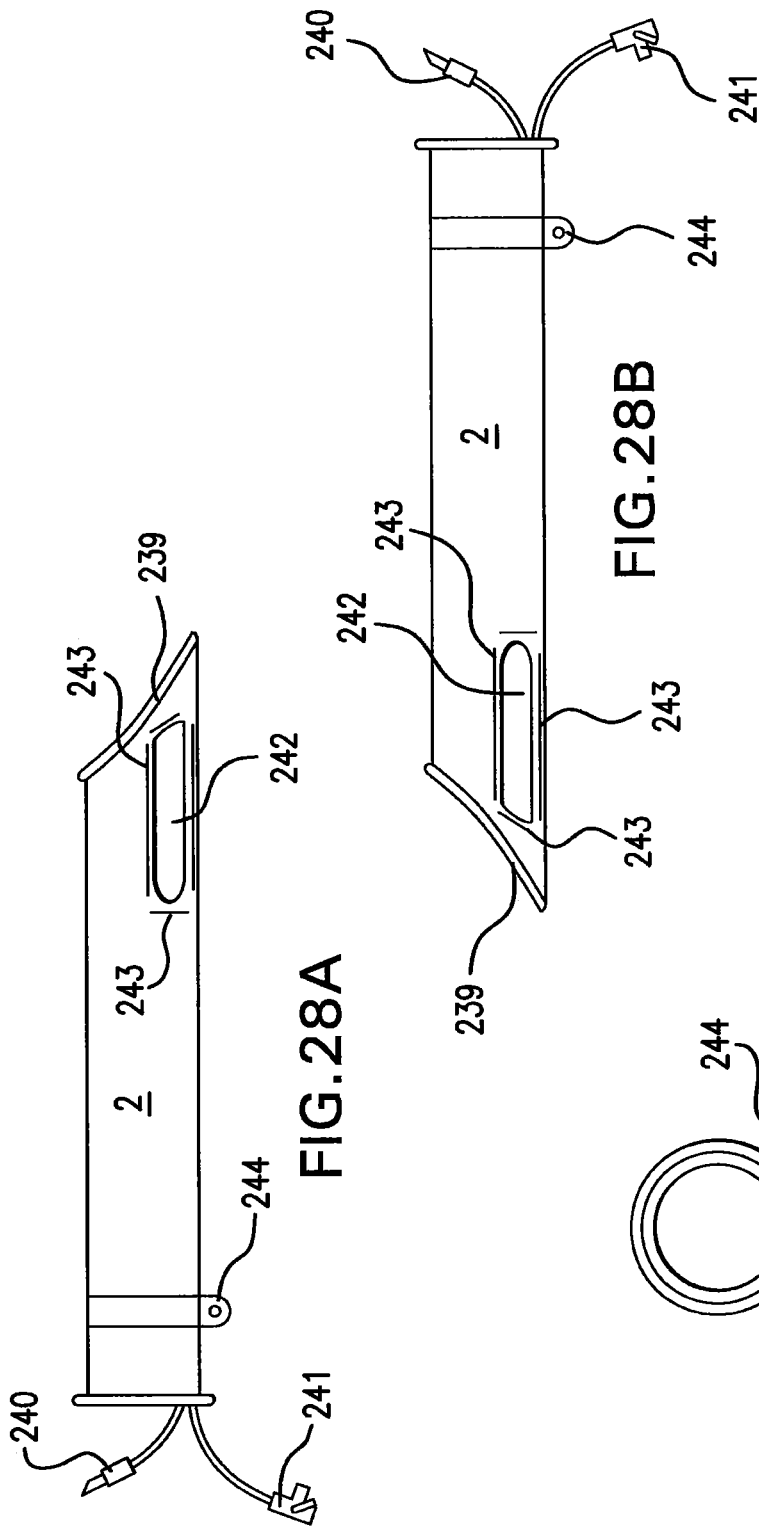

METHODS AND DEVICES FOR ENDOSCOPIC ACCESS TO THE HEART

RELATED APPLICATIONS

The present application is a divisional of U.S. patent application Ser. No. 12/642,137, filed Dec. 18, 2009, which itself claims priority to U.S. Provisional Patent Application No. 61/203,173, filed Dec. 19, 2008, and U.S. Provisional Patent Application No. 61/262,372, filed Nov. 18, 2009 the contents of all of which are incorporated by reference in their entireties herein.

FIELD OF THE INVENTION

The present invention relates to methods and devices for endoscopic access to the heart, including direct endoscopic access to the left atrium.

BACKGROUND

Traditionally, access to the left atrium and the structures within the left atrium has been limited to direct surgical access via sternotomy or thoracotomy or by percutaneous access via the femoral vessels and crossing the intra-atrial septum from the right to the left atrium. Although some therapies may be applied to the left atrial surface (as for atrial fibrillation), there are other therapies which are beneficial when applied within, or through, the left atrium, rather than on the left atrial surface. These therapies may include, but are not limited to, the treatment of mitral valve pathology, aortic valve pathology, atrial and ventricular dysarrhythmias, management of the left atrial appendage, and placement of leads and sensors to manage heart failure in conjunction with implanted devices.

To gain access to the left atrium via surgical approach (sternotomy or thoracotomy) cardiopulmonary bypass is usually required. Once this is initiated, the left atrium can be surgically opened with an incision. These incisions have allowed the introduction of large instruments and the surgeon's hands into the chest and abdomen to perform complex surgical procedures. The surgeon can then perform the necessary procedure to the left atrium and to structures inside the left atrium.

Interventional cardiologists or electrophysiologists may gain access to the left atrium by percutaneous cannulation of the femoral vein, and positioning a catheter across the atrial septum into the left atrium. Via this trans-septal approach, cardiologists can perform percutaneous procedures within the left atrium, such as catheter ablations. However, the trans-septal approach is difficult to perform and leaves the patient with a potential atrial septal defect.

Also, patients with a failing heart may require mechanical cardiac support either temporarily or permanently, to remain alive. Mechanical support can be temporary until the heart recovers and can return to independent function, or may be long-term until an appropriate heart becomes available for transplantation. This type of mechanical support can require the placement of large cannulas in the heart and great vessels (aorta, pulmonary artery) to pump the blood for the heart. When the right heart fails, a device can be connected to the right atrium and pulmonary to pump blood from the body to the lungs. When the left heart fails, a device may be connected to the left atrium and the aorta to pump blood from the lungs to the body. In some situations, a patient may require both a right and a left heart assist device. In both situations, these mechanical support devices are placed during open heart surgical procedures using a median sternotomy and cardiopulmonary bypass.

There are currently no cardioscopic devices or methods to directly access the left atrium and certain other regions of the heart. Thus, there is a need for devices and methods to simplify access to the heart. In this way, risk to the patient, and trauma resulting from the surgery can be minimized. For example, there is a need for the cardioscopic and pericardioscopic devices, methods and systems of the present invention which encompass methods, devices, and systems for cardiac assistance (temporary or long-term), epicardial lead placement, ablative therapy, and placement of epicardial shock devices, and other therapeutic treatments that can be accomplished while the heart is beating.

SUMMARY

The present inventions relate generally to devices and methods for directly visualizing and operating upon and within the heart, including the left atrium and the right atrium.

In certain embodiments, the present invention comprises the development of new, and the improvement of existing, surgical tools, instrumentation, techniques, and methods to directly visualize and perform procedures upon and within the heart, including the left atrium, the right atrium, and structures within, and in proximity to, the left atrium and the right atrium. Utilizing cardioscopic access to the atrium, instrumentation may be positioned within the atrium directly.

The present invention, in certain embodiments, encompasses methods, devices and systems to access and perform procedures within the heart, including the left atrium, the right atrium, left ventricle, right ventrical, left atrial appendage, aorta, and to the aortic and mitral valve via the left or right atrium. Embodiments of the present invention also encompass methods, devices and systems to access and perform procedures within the pericardium to allow direct cannulation of the left atrium, left ventricle, right atrium, right ventricle, aorta, and pulmonary artery for cardiac support technology.

Embodiments of the present invention also encompass methods, devices and systems to access and perform electrophysiologic procedures including endocardial ablation within the heart, including the left atrium and the right atrium, on the right and left ventricles, and epicardial/endocardial lead placement. Such methods, devices and systems may employ an atrial portal and/or pericardial portal as described herein. Also, such methods, devices and systems may employ a pericardial portal as described herein. The methods, devices and systems of the present invention may comprise accessory devices such as needles, wires, and ports designed to be used with embodiments of either the atrial portal or the pericardial portal.

The present invention may be embodied in a variety of ways. For example, in one embodiment, the present invention comprises a method to access the atrium of a heart of a subject, the method comprising; inserting the distal end of an atrial portal into the pericardium of the subject; manipulating the proximal end of the atrial portal to position the distal end of the atrial portal at the surface of the atrium; determining an entry location for the atrial portal to be inserted into the atrium; inserting the atrial portal into the atrium; and securing the position of the atrial portal in the atrium.

In other embodiments, the present invention comprises devices for accessing the atrium in a heart in a subject, the device comprising an atrial portal having a configuration such that the distal end of the atrial portal can access the atrium endoscopically via the pericardial sac while the proximal end of the atrial portal can extend to outside of the subject.

In yet other embodiments, the present invention comprises systems for accessing the atrium of a heart in a subject, the system comprising an atrial portal having a configuration such that the distal end of the atrial portal can access the atrium endoscopically via the pericardial sac while the proximal end of the atrial portal can extend to outside of the subject.

In an embodiment, the atrium accessed by the devices, methods and systems of the invention is the left atrium.

DESCRIPTION OF THE FIGURES

The present invention may be further understood by referring to the following non-limiting figures which illustrate embodiments of the present invention.

FIG. 6 illustrates a left atrial portal passing into the left atrial wall and secured by a purse string suture in accordance with an embodiment of the present invention.

FIGS. 7A-7D show a suture capture device, where panel A shows the device which is passed through a tourniquet, FIG. 7B shows capture of the suture, FIG. 7C shows the suture being retrieved from the distal end of the tourniquet, and FIG. 7D shows the suture from a purse string suture in the atrial wall pulled through the tourniquet and out the proximal opening, so that tension applied to the proximal end of the suture can be used to tighten the distal ends of the suture in accordance with an embodiment of the present invention.

FIGS. 8A-8D illustrate a pericardial portal with a tourniquet, a left atrial portal, and an endoscope inside the distal opening of the pericardial portal in accordance with an embodiment of the present invention, where FIG. 8A shows an atrial portal in the lumen of a pericardial portal, FIG. 8B shows a guide wire being inserted into the entry location for an atrial portal under view of an endoscope in a pericardial portal, FIG. 8C shows an atrial portal being inserted in the atrium over a guide wire, and FIG. 8D shows an atrial portal in position in the atrium wall, with the purse string sutures tightened around the atrial portal using a tourniquet inside a pericardial portal.

FIGS. 9A-9H demonstrate placement of a left atrial portal in a left atrial wall in accordance with an embodiment of the present invention, where FIGS. 9A-9D show the components separately, and FIGS. 9E-9H show an embodiment that employs the left atrial portal, dilator introducer, and introducer needle substantially simultaneously, such that FIG. 9A shows purse string sutures positioned with pledgets on the epicardial surface, and a hollow bore needle is placed into the left atrium; FIG. 9B shows a guide wire passed through the needle and into the left atrium; FIG. 9C shows the needle removed and the guide wire passing from outside the abdomen, through a pericardial port (not shown) and inside the left atrium; and FIG. 9D demonstrates the position of a left atrial portal within the left atrium over the guide wire where a removable dilating introducer enlarges the opening of the left atrial wall over the wire; FIG. 9E shows a purse string suture and pledgets on the left atrial epicardial surface, and the left atrial portal, dilator, and needle placed in the middle of the purse string suture; FIG. 9F shows the needle advanced into the left atrium; FIG. 9G shows a guide wire been passed through the needle and positioned inside the left atrium allowing the left atrial portal, dilator, and needle to be advanced as one unit through the left atrial wall; and FIG. 9H shows the left atrial portal within the left atrium over the guide wire with the needle removed from the atrium and back into the atrial portal.

FIG. 10A and FIG. 10B show alternate embodiments of the distal end of an atrial portal; FIG. 10C and FIG. 10D shows an embodiment of the proximal end of an atrial portal; FIG. 10E depicts the an atrial portal with a nonremovable port, a one-way valve and a stopcock assembly; FIG. 10F shows an embodiment of a distal port in a head on view; FIG. 10G shows a side view and FIG. 10H shows an end view of a triangular shaped proximal port with three one-way valves.

FIGS. 19A and 19B illustrate how a barbed needle is advanced out of the end of an introducer needle, where a sheath over the suture is used to advance the suture and the barbed needle out of the distal end of the introducer needle, in accordance with an embodiment of the present invention.

FIG. 26A depicts a pacing lead with the proximal end having the bipolar or unipolar lead attachment; FIG. 26B shows a head-on view of the distal end of the lead, and FIG. 26C shows the fixation unit for the lead.

FIG. 27A shows the atrial pressure sensor, FIG. 27B shows deployment of the pressure sensor in the left atrium, and FIG. 27C shows the atrial pressure sensor in a final deployed position.

FIGS. 28A-28C depict a pericardial portal in accordance with an embodiment of the present invention in various views: right view (FIG. 28A), left view (FIG. 28B), and end view (FIG. 28C).

DETAILED DESCRIPTION

Figure 1:
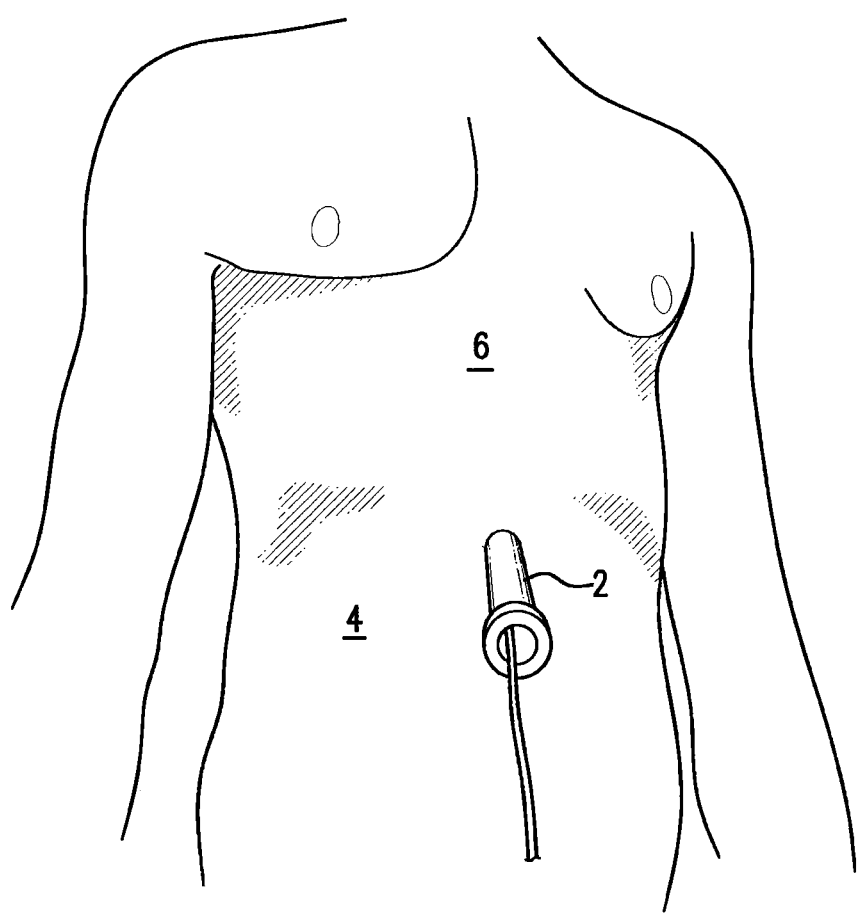
FIG. 1 illustrates the surface anatomy of a person and a location for insertion of a pericardial and atrial portal in accordance with an embodiment of the present invention.

Embodiments of the present invention include new devices, and improvements to existing devices, instrumentation, and procedures for providing direct access to the left atrium, or other regions of the heart, via minimally invasive, endoscopic approaches. In certain embodiment, the devices, methods and systems of the present invention comprise an atrial portal as described herein. In yet other embodiments, the devices, methods and systems of the present invention comprise a pericardial portal as described herein. Embodiments of the present invention also comprise methods for using such atrial portals and pericardial portals to perform surgery on the heart, and systems (e.g., kits) comprising these portals in combination with other therapeutic devices.

Thus, in certain embodiments, the devices, methods and systems of the present invention may be used with accessory devices. Examples of such devices include, but are not limited to, devices and instrumentation such as needles, wires, and ports designed to be used for positioning the atrial portal utilizing pericardioscopy or similar endoscopic or minimally invasive cardiac access. Non-limiting embodiments of such devices are depicted in the diagrams and description included herein.

In other embodiments, the devices, methods and systems of the present invention may comprise the use of existing catheters, needle passers, forceps, or other intracardiac devices.

As described herein, the use of pericardioscopy or cardioscopy can in certain embodiments of the present invention, provide direct access to the pericardium and the left atrial surface. Without the pericardioscopic (e.g., pericardial portal) and cardioscopic (e.g., atrial portal) devices, methods and systems of the present invention, direct visualization and manipulation of the left atrium is only possible via large and sometimes painful incisions. Utilizing a pericardioscopic and cardioscopic approach, the left atrium can be directly cannulated using only minimally invasive, port access techniques and endoscopic instrumentation and visualization. For example, by directly cannulating the left atrium, catheters and devices can be positioned into the left atrium with minimal difficulty. Procedures such as endocardial atrial or ventricular ablations, mitral valve repair or replacement, aortic valve replacement, stent placement, management of intracardiac congenital defects or tumors, and management of the atrial appendage, and endocardial lead and/or sensor placement are examples of procedures that may be performed using the devices, methods and systems of the present invention.

As used herein, a subject or an individual is an animal. For example, the subject may comprise a mammal. In one embodiment, the subject may be a human. In certain embodiments, the subject is a patient seeking medical treatment (e.g., for a heart condition). The user of the devices, methods, and systems of the present invention may be a physician, veterinarian, or other type of health care professional.

As used herein, a portal is a chamber that provides access from outside of the subject to an organ inside of the subject, such that procedures may be performed in the organ vial the portal. An endoscopic portal is a portal that has an endoscope or other imaging device at least partly contained within its lumen such that the distal end of the portal, and tissues and/or organs positioned at the distal end of the portal, can be viewed by an operator at the proximal end. The portal thereby provides a conduit that can be fixed (if needed) at the organ to be treated, with a distal end that can be used to insert tools or devices in the organ.

As used herein, a cannula is a small tube or cylinder that is inserted into the body and that may be used to insert fluid and or tools inside the body. An endoscopic cannula is a cannula that has an endoscope or other imaging device at least partly contained within its lumen such that the distal end of the cannula, and tissues and/or organs positioned at the distal end of the cannula, can be viewed by an operator at the proximal end.

An endoscope is a small flexible tube with a light and lens that may be used to view an organ or body part via a cannula or a portal.

As used herein, the words "proximal" and "distal" refer to direction closer to and away from, respectively, an operator (e.g., surgeon, physician, nurse, technician, etc.) who would insert a device (e.g., a portal of the present invention) into the patient, such that the distal end of the device is the end that is inserted inside a patient's body, while the end outside the patient's body would be the proximal end.

As used herein, the epicardial surface is the outer surface of the heart. The term epicardial surface is also used to refer to the innermost of the two layers of pericardium.

The endocardium is the membrane that lines the cavities of the heart and forms part of the heart valves—i.e., the innermost layer of the heart.

Also, as used herein, the pericardial surface is the outer surface of the pericardial sac. The pericardium is a double-walled sac that contains the heart and the roots of the great vessels.

Also, as used herein, pericardioscopy and/or pericardioscopic refers to endoscopic devices and methods that can provide access to the pericardium and the epicardial (outer) surface of the heart. Cardioscopy and/or cardioscopic, refers to endoscopic devices and methods that can provide access to the endocardial (inner) surface of the heart. In general, pericardioscopic and cardioscopic access to the thoracic cavity may be made via an incision in diaphragm. Or, other types of access may be used. The procedures performed in and on the heart may be surgical, where surgery encompasses physical manipulation of the heart tissue in a significant manner. In certain embodiments, surgery comprises making incisions in the heart tissue. Or, the procedures may involve emplacing a device and/or tool on or in the heart tissue. Or, the procedures may comprise mapping of electrical current within at least a portion of the heart tissue.

Furthermore, in this specification and the appended claims, the singular forms "a," "an" and "the" include plural referents unless the context clearly dictates otherwise. Thus, for example, the term "a lumen" is intended to mean a single lumen or a combination of lumens, "a fluid" is intended to mean one or more fluids, or a mixture thereof.

Methods, Devices and Systems for Endoscopic Access to the Heart

Embodiments of the present invention comprise methods, devices, and systems for endoscopic access to the heart, including direct endoscopic access to the left atrium. The present invention may be embodied in a variety of ways.

In certain embodiments, the present invention may comprise methods to access the atrium of a subject so as to perform surgical procedures upon the atrium. The method may comprise the steps of inserting the distal end of an atrial portal into the pericardium of the subject; manipulating the proximal end of the atrial portal to position the distal end of the atrial portal at the surface of the atrium; determining an entry location for the atrial portal to be inserted into the atrium; inserting the atrial portal into the atrium; and securing the position of the atrial portal in the atrium. In an embodiment, the atrium is the left atrium and the device comprises a left atrial portal. In other embodiments, the atrium is the right atrium, and the device comprises a right atrial portal. For each of the embodiments disclosed herein, the atrial portal may access either the right or left atrium as required, and as understood by those of skill in the art. Thus, for most embodiments, reference to the left atrial portal will include an atrial portal that can be used to access a right atrium.

In certain embodiments, a pericardioscopic portal is used in combination with the atrial portal. Thus, in certain embodiments, the method may comprise inserting the atrial portal into a pericardioscopic portal and positioning the distal end of the pericardioscopic portal at the surface of the atrium.

In certain embodiments, at least one of an ultrasound probe, an endoscope, or other imaging device is used in combination with the atrial portal. Thus, in certain embodiments, the method may comprise using an ultrasound probe positioned at the distal end of the atrial portal to provide an image of body structures present near the distal end of the atrial portal. In an embodiment, a pericardial portal may be used to position an endoscope to be used with the atrial portal. Or, an ultrasound probe may be included in the lumen of the pericardial portal. Or, the imaging device may be delivered independently of either the atrial portal or the pericardioscopic portal.

In certain embodiments, the method provides sutures around the opening (defect) made in the wall of the atrium, as a way to secure the atrial portal in the atrium wall. The sutures may be tightened such that the insertion of the atrial portal into the atrium wall does not result in loss of blood from the atrium. Thus, in certain embodiments, the method may comprise providing sutures in the surface of the atrium that surround the entry location for the atrial portal and tightening the sutures around the atrial portal upon insertion of the atrial portal in the atrium to secure the atrial portal in the atrium. In an embodiment, a pericardial portal is used to position tools used to make the sutures. Or, the suturing tools may be included in the lumen of the atrial portal. Or, the suturing tools may be delivered independently of either the atrial portal or the pericardioscopic portal.

The sutures may comprise (or be used in combination with) a pledget, or a plurality of pledgets, or other type of reinforcing element to distribute the pressure from the sutures more evenly on the tissue to reduce injury to the tissue.

In certain embodiments, the method may comprise the use of a tourniquet type device to tighten the sutures that have been emplaced in the atrium wall such that there is a tight seal between the sutures and the atrial portal. Thus, in certain embodiments, the method may comprise providing a tourniquet to tighten the sutures around the atrial portal. The tourniquet may be positioned adjacent to the atrial portal. In certain embodiments a cardioscopic Rommel tourniquet may be used. Or, other types of tourniquets that can be used cardioscopically may be used. Also, in certain embodiments, the tourniquet comprises a suture capture device which allows a user with access to the proximal end of the tourniquet to tighten the sutures around the atrial portal so as to secure the atrial portal in the atrium. In an embodiment, a pericardial portal is used to position the tourniquet and/or the suture capture device. Or, the tourniquet and/or the suture capture device may be included in the lumen of the atrial portal. Or, the tourniquet and/or the suture capture device may be delivered independently of either the atrial portal or the pericardioscopic portal.

In certain embodiments, the atrial portal is inserted into the atrium wall by making a small (needle-sized) defect (i.e., 0.1-3 mm, or 0.2 to 2 mm, or about 0.5 to 1 mm in size) in the wall and then advancing the atrial portal into the wall through the defect. This type of entry can minimize loss of blood as the atrial portal is inserted into the atrium wall. Thus, in certain embodiments, the step of inserting the atrial portal into the atrium comprises using an introducer needle contained within the atrial portal to puncture the atrium wall.

Once the defect has been made in the atrium, a guide wire may be inserted into the atrium. This guide wire may then provide a platform for insertion of the atrial portal and associated tools into the atrium. Guide wires generally used for such surgical procedures may be employed. For example, in certain embodiments, a 0.014 guide wire (about 0.35 mm in diameter) or a 0.038 guide wire (about 1 mm in diameter) may be used. For example, in certain embodiments, the method may comprise inserting a guide wire through the needle used to make a defect in the atrium, and withdrawing the needle such that the guide wire is inserted into the atrium at the entry location for the atrial portal. The method may further comprise threading the atrial portal over the guide wire and into the atrium.

The atrial portal has a diameter that is greater than the diameter of a needle or a guide wire. Thus, in certain embodiments, the distal tip of the atrial portal may comprise a dilating introducer. In certain embodiments, the dilating introducer may be graduated, such that it is more narrow at the most distal point of the introducer and widens to the circumference of the main body of the atrial portal at the proximal end of the introducer. Thus, in certain embodiments, the step of inserting the atrial portal into the atrium comprises inserting a dilating introducer positioned at the distal end of the atrial portal into the entry location and pushing the introducer distally into the atrium wall to enlarge the opening at the entry location. Or, other types of graduated distal tips may be used to facilitate entry of the atrial portal into the atrium.

There may be a need to secure the atrial portal in the wall of the atrium. In one embodiment, sutures emplaced in the atrium wall can be used to tighten the atrium wall around the circumference of the atrial portal once the portal has been inserted in the atrium wall. Also, in certain embodiments, the distal end of the atrial portal may comprise a cap that is configured to assist with securing the atrial portal in the atrium wall. The cap may be made of a rubber or other expandable or inflatable material that can be expanded at least at certain parts of the cap so as to prevent the portal from moving distally or proximally in relation to the atrial wall. Thus, in certain embodiments, the method may comprise using a flexible cap positioned on the distal end of the atrial portal to secure the distal end of the atrial portal in the atrial wall. In certain embodiments, at least a portion of the cap can be expanded laterally away from the central longitudinal axis of the atrial portal. In this way, the cap may increase the tightness of the seal between the outer surface of the atrial portal and the atrium wall. Also, and as described in more detail herein, the cap may, in certain embodiments, comprise a shape that is larger (i.e., has a greater circumference) on the distal end of the cap then a central portion of the cap and/or a proximal portion of the cap when the atrial portal is inserted into the entry location of the atrium. In this way, the cap may prevent the atrial portal from being pulled proximally out of the atrium. Also, in certain embodiments, the cap may comprise an expandable or extendable portion on the proximal end of the cap that can be used to prevent the atrial portal from being pushed more distally into the atrium.

The atrial portals of the present invention can provide direct access to either the left atrium or the right atrium and portions of the heart that can be accessed from the left or right atrium. For example, once the atrial portal is in position in the left atrium, the left or right atrium endocardium, mitral valve, left ventricle, aorta, vessels leading to or from the heart, and other structures may be accessed. Also, the pericardial portals of the present invention may be used to provide access to the epicardial surface or the surface of the pericardial sac. Thus, in certain embodiments, the method may comprise inserting a tool in the atrium using the atrial portal and in some cases the pericardial portal of the present invention. Alternatively, the present invention provides methods to access either the epicardial surface or the pericardial surface using a pericardial portal.

In this way, using the atrial portals and the pericardial portals of the present invention, therapeutic procedures may be performed on the heart, e.g., by inserting tools to perform such therapeutic procedures into the atrium via the atrial portal or by accessing the pericardial surface or the epicardial surface using a pericardial portal.

There may be a variety of methods used to position a tool that has been inserted into the heart via an atrial portal at the correct location in the heart. In certain embodiments, the tool may be threaded over a guide wire that extends from the proximal end of the atrial portal (i.e., the part of the atrial portal that exits the body) to the distal end of the atrial portal (i.e., the part of the atrial portal that is inserted into the atrium).

A variety of tools may be inserted into the atrium for use in therapeutic procedures in either the atrium or other structures and regions of the heart. Also, a variety of tools may be employed on the epicardial (or pericardial) surface for use in therapeutic procedures on either the atrium or other structures and regions of the heart.

In certain embodiments, the tool may comprise an ablation element that is used to ablate a portion of the atrium or another part of the heart and/or vessels leading to or from the heart (e.g., a vessel leading into or out of the left atrium). In an embodiment, such ablation may be used to treat atrial fibrillation (AF). Alternatively, such ablation may be used to reduce a valve from a first extended configuration to a smaller configuration.

In other embodiments, the tool may comprise an electrode that is used to measure electrical activity at a site in the atrium or another region of the heart.

Or, the tool may comprise an inner cannula for implanting at least one of a stent, or a valve in the heart. For example, in certain embodiments of using an atrial portal, the method may comprise manipulating the proximal end of an inner cannula and/or catheter comprising a stent and/or valve prosthesis to position the stent and/or valve prosthesis within a vessel leading into or from the atrium. The inner cannula and/or catheter for implanting a valve and/or a stent may, in certain embodiments, comprise an expandable member to expand a diseased valve or vessel in the subject prior to emplacement of the therapeutic valve and/or stent. Also, in some embodiments, the inner cannula and/or catheter may comprise a capture device that can be positioned adjacent to the sight of implantation of the valve and/or the stent to trap debris that may be loosened from the vessel or the valve during the implantation procedure.

In other embodiments, an atrial portal of the present invention may be used for delivery of devices that can be used for mitral valve reduction. Thus, in certain embodiments, the method may comprise implanting at least two barbed needles near a valve in need of reduction and pulling distally (e.g., using sutures attached to the proximal end of the barbed needles) on the two implanted barbed needles to reduce the circumference of the valve. For example, an inner catheter or cannula comprising a barbed needle attached to a suture may be threaded through an atrial portal and implanted in the posterior annulus of the mitral valve. In an embodiment, the barbed needle may be contained within an introducer prior to positioning in the mitral valve. Also, in an embodiment, a sheath that extends proximally and that covers the suture, but provides stiffness, may be used to push the barbed needle through the introducer and into the tissue.

Embodiments of the present invention also comprise devices for cardioscopic and pericardioscopic access of the heart. In certain embodiments, the present invention comprises device for accessing an atrium of the heart in a subject so as to perform a therapeutic procedure upon the atrium or to access other regions of the heart. The device may comprise an atrial portal having a configuration such that the distal end of the atrial portal can provide cardioscopic access the atrium by insertion of the distal end of the portal into the atrium while the proximal end of the atrial portal can extend to outside of the subject. In an embodiment, the portal is fashioned to access the left atrium. Or, the portal may be fashioned to access the right atrium. For each of the embodiments disclosed herein, the atrial portal may access either the right or left atrium as required, and as understood by those of skill in the art. Thus, for most embodiments, reference to the left atrial portal will include an atrial portal that can be used to access a right atrium.

Yet other embodiments of the present invention comprise a pericardial portal. In certain embodiments, the pericardial portal may be fashioned to have a configuration such that the distal end of the pericardial portal can provide pericardioscopic access the pericardium or epicardium, while the proximal end of the pericardial portal can extend to outside of the subject. In an embodiment, the pericardial portal may be fashioned to have a configuration such that when an atrial portal is inserted into the lumen of the pericardial portal, the distal end of the atrial portal can access the atrium while the proximal end of the atrial portal can extend to outside of the subject.

In certain embodiments, the present invention may comprise a system. For example, in certain embodiments, the system may comprise an atrial portal in combination with a tool to be used with the atrial portal. Or, the system may comprise an atrial portal to be used in combination with a pericardial portal. Or, the system may comprise a pericardial portal in combination with therapeutic tool to be used with the pericardial portal.

In certain embodiments, the devices and/or systems of the present invention may comprise an imaging tool. In certain embodiments, the imaging tool may be an ultrasound probe or an endoscope to provide an image of body structures present near the distal end of the atrial portal or the pericardial portal. The endoscope may be positioned near the distal end of the atrial portal to provide a visual image of body structures present near the distal end of the atrial portal. In an embodiment, a pericardial portal is used to position the endoscope or the ultrasound probe. Or, an ultrasound probe may be included in the lumen of the atrial portal.

In certain embodiments, the devices and/or systems of the present invention comprise a tool to provide sutures around the opening (defect) made in the wall of the atrium, as a way to secure an atrial portal in the atrium wall. The sutures may be tightened such that the insertion of the atrial portal into the atrium wall does not result in loss of blood from the atrium. In an embodiment, a pericardial portal comprises the tool configured for emplacing sutures in the atrial wall to secure the atrial portal in the atrium. Or, the suturing tools may be included in the lumen of the atrial portal. Or, the suturing tools may be delivered independently of either the atrial portal or the pericardioscopic portal. For example, in certain embodiments of the devices and systems of the present invention, the sutures are of a configuration so as to surround the atrial portal upon insertion of the atrial portal in the atrium such that tightening the sutures around the atrial portal secures the atrial portal in the atrium.

The sutures may comprise (or be used in combination with) a pledget, or a plurality of pledgets, or other type of reinforcing element to distribute the pressure from the sutures more evenly on the tissue to reduce injury to the tissue.

In certain embodiments, the devices and/or systems of the present invention may comprise a tourniquet type device to tighten the sutures that have been emplaced in the atrium wall such that there is a tight seal between the sutures and the atrial portal. The tourniquet may be positioned adjacent to the atrial portal. In certain embodiments a cardioscopic Rommel tourniquet may be used. Or, other types of tourniquets that can be used cardioscopically may be used. Also, in certain embodiments, the tourniquet comprises a suture capture device which allows a user with access to the proximal end of the tourniquet to tighten the sutures around the atrial portal so as to secure the atrial portal in the atrium. In an embodiment, the tourniquet and/or the suture capture device is provided as part of a pericardial portal. Or, the tourniquet and/or the suture capture device may be included in the lumen of the atrial portal. Or, the tourniquet and/or the suture capture device may be delivered independently of either the atrial portal or the pericardial portal.

In certain embodiments of the devices and systems of the present invention, the atrial portal is inserted into the atrium wall by making a small (needle-sized) defect (i.e., 0.1-3 mm, or 0.2 to 2 mm, or about 0.5 to 1 mm in size) in the wall and then squeezing the atrial portal into the wall through the defect. This type of entry can minimize loss of blood as the atrial portal is inserted into the atrium wall. Thus, in certain embodiments, atrial portal further comprises a needle within the lumen of the atrial portal, wherein the needle is configured to puncture the atrium so as to provide an opening for insertion of the left portal into the atrium.

Once the defect has been made in the atrium, a guide wire may be inserted into the atrium. This guide wire may then provide a platform for insertion of the atrial portal and associated tools into the atrium. Guide wires generally used for such surgical procedures may be employed. For example, in certain embodiments, a 0.014 guide wire (about 0.35 mm in diameter) or a 0.038 guide wire (about 1 mm in diameter) may be used. For example, in certain embodiments, the atrial portal further comprises a guide wire, wherein the guide wire is configured to provide a path for insertion of the atrial portal into the atrium by threading the atrial portal over the guide wire and into the atrium, and withdrawing the needle such that the guide wire is inserted into the atrium at the entry location for the atrial portal. The method may further comprise threading the atrial portal over the guide wire and into the atrium.

The atrial portal may generally have a diameter that is greater than the diameter of a needle or a guide wire. Thus, in certain embodiments of the devices and systems of the present invention, the distal tip of the atrial portal may comprise a dilating introducer. In certain embodiments, the dilating introducer may be graduated, such that it is more narrow at the most distal point of the introducer and widens to the circumference of the main body of the atrial portal at the proximal end of the introducer. Thus, in certain embodiments, the distal end of the atrial portal comprises a dilating introducer, wherein the dilating introducer is configured so as to be inserted in an opening in the atrial wall so as to enlarge the opening of the atrial wall for insertion of the atrial portal into the atrium. Or, other types of graduated distal tips may be used to facilitate entry of the atrial portal into the atrium.

There may be a need to secure the atrial portal of the devices and systems of the present invention in the wall of the atrium. In one embodiment, sutures emplaced in the atrium wall can be used to tighten the atrium wall around the circumference of the atrial portal once the portal has been inserted in the atrium wall. Alternatively or additionally, in certain embodiments of the devices and systems of the present invention, the distal end of the atrial portal may comprise a cap that is configured to assist with securing the atrial portal in the atrium wall. The cap may be made of a rubber or other material that can be expanded at least at certain parts of the cap so as to prevent the portal from moving distally or proximally in relation to the atrial wall. Thus, in certain embodiments, the cap can be expanded laterally away from the central longitudinal axis of the atrial portal. In certain embodiments, at least a portion of the cap can be expanded laterally away from the central longitudinal axis of the atrial portal. In this way, the cap may increase the tightness of the seal between the outer surface of the atrial portal and the atrium wall. Also, and as described in more detail herein, the cap may, in certain embodiments, comprise a shape that is larger (i.e., has a greater diameter) on the distal end of the cap then at a central portion of the cap and/or a proximal portion of the cap when the atrial portal is inserted into the entry location of the atrium. In this way, the cap may prevent the atrial portal from being pulled proximally out of the atrium. Also, in certain embodiments, the cap may comprise an expandable or extendable portion on the proximal end of the cap, wherein the extendable portion is configured to be positioned on the outer atrial surface so as to prevent the atrial portal from being inserted into the atrium further than the length of the cap.

As noted above, the atrial portals of the devices and systems of the present invention can provide direct access to either the left atrium or the right atrium and portions of the heart that can be accessed from the left or right atrium. Also, the pericardial portals of the present invention may be used to provide access to the epicardial surface or the surface of the pericardial sac. Thus, using the atrial portals and the pericardial portals of the present invention, therapeutic procedures may be performed on the heart, e.g., by inserting tools to perform such therapeutic procedures into the atrium via the atrial portal or by accessing the pericardial surface or the epicardial surface using a pericardial portal.

There may be a variety of methods used to position a tool that has been inserted into the heart via an atrial portal of the devices and systems at the correct location in the heart. In certain embodiments, the atrial portal or pericardial portal may comprise a guide wire for positioning tools on or in the heart. Thus, in certain embodiments of the devices and systems of the present invention, the tool is configured to be threaded over a guide wire that extends from the proximal end of the atrial portal (and/or the pericardial portal) to the distal end of the atrial portal and/or the pericardial portal. The tool may then be threaded over the guide wire that extends from the proximal end of the atrial portal (i.e., the part of the atrial portal that exits the body) to the distal end of the atrial portal (i.e., the part of the atrial portal that is inserted into the atrium). Or, the tool may be threaded over a guide wire that extends from the proximal end of the pericardial portal (i.e., the part of the pericardial portal that exits the body) to the distal end of the pericardial portal (i.e., the part of the pericardial portal that is near the heart).

Using the devices and systems of the present invention, a variety of tools may be inserted into the atrium for use in therapeutic procedures in either the atrium or other structures and regions of the heart. Also, a variety of tools may be employed on the epicardial (or pericardial) surface for use in therapeutic procedures on either the atrium or other structures and regions of the heart.

Thus, in certain embodiments of the devices and systems of the present invention, the tool may comprise an ablation element that is used to ablate a portion of the atrium or another part of the heart and/or vessels leading to or from the heart (e.g., a vessel leading into or out of the atrium). In an embodiment, such ablation may be used to treat atrial fibrillation (AF), atrial tachycardia or flutter, as well as ventricular arrhythmias such as ventricular tachycardia. Alternatively, such ablation may be used to reduce a valve from a first extended configuration to a smaller configuration.

In other embodiments, the tool may comprise an electrode that is used to measure electrical activity at a site in the atrium or another region of the heart.

Or, the tool of the devices and systems of the present invention may comprise an inner cannula for implanting at least one of a stent and/or a valve prosthesis in the heart. For example, in certain embodiments of using an atrial portal, the method may comprise manipulating the proximal end of the inner cannula and/or catheter to position the stent and/or valve prosthesis within a vessel leading into or from the atrium. The inner cannula for implanting a valve and/or a stent may, in certain embodiments, comprise an expandable member to expand a diseased valve or vessel in the subject prior to emplacement of the therapeutic valve and/or stent. Also, in some embodiments, the inner cannula and/or catheter may comprise a capture device that can be positioned adjacent to the sight of implantation of the valve and/or the stent to trap debris that may be loosened from the vessel or the valve during the implantation procedure.

In other embodiments of the devices and systems of the present invention, the atrial portal may be used for delivery of devices that can be used for mitral valve reduction. Thus, in certain embodiments, the method may comprise implanting at least two barbed needles near a valve in need of reduction and pulling distally on the two implanted barbed needles (e.g., using sutures attached to the barbed needles) to reduce the circumference of the valve. For example, an inner catheter or cannula comprising a barbed needle attached to a suture may be threaded through the atrial portal and implanted in the posterior annulus of the mitral valve. In an embodiment, the barbed needle may be contained within an introducer prior to positioning in the mitral valve. Also, in an embodiment, a sheath that extends proximally and that covers the suture, but provides stiffness is used to push the barbed needle through the introducer and into the tissue.

Atrial Portal Procedures and Devices

In certain embodiments, the present invention relates to atrial portal procedures and devices for performing such procedures. The atrial portal may, in certain embodiments, be used in combination with a pericardioscopic portal which can provide access to the pericardium for the atrial portal and other devices. Alternatively and/or additionally, the atrial portal may be used with a pericardioscopic cannula.

There is often, however, a need to directly access the left atrium without using a trans-septal approach. Thus, certain embodiments are of the methods, devices and systems may be used to directly access the left and/or the right atrium.

For example, in certain embodiments, after positioning a left atrial portal and/or a pericardial portal inside the pericardial sac, the left atrium may be directly visualized such that the posterior left atrium with associated left and right inferior pulmonary veins can be identified. The appropriate site for insertion of the left atrial portal in the atrium (i.e., the entry location) may differ depending upon the procedure to be performed within the left atrium. For example, mitral valve procedures may require differing placement than ablative procedures. After identifying the appropriate entry location for the left atrial portal, an endoscope (e.g., contained within a pericardial portal) may be positioned for optimal visualization of the left atrial portal entry location.

At this point, a suture may be positioned near the entry location in the atrial wall. As discussed in more detail herein, the suture (or sutures) may be used to secure the atrial portal in the heart wall. Also, the sutures may be used to close the entry location (i.e., the orifice made in the left atrium) after the atrial portal is removed.

In certain embodiments, a suture or sutures may be positioned around the circumference of the entry location. For example, in certain embodiments, the suture or sutures may be positioned in a purse string manner as illustrated in detail herein. Or, other arrangements and/or suturing techniques may be used. In certain embodiments, the suture is used in combination with pledgets. Such pledgets can provide support for the sutures and also provide a surface to abut the left atrial portal so as to secure the left atrial portal in the atrium wall.

The size of the suture, and the size of the entry location for the atrial portal may be varied as required by the size of the atrial portal. For example, where a purse-string technique is employed, the purse-string may have pledgets on at least two sides and may be configured to surround the entry location appropriately sized for the atrial portal. As described in more detail below, a atrial portal needle and/or introducer may then be positioned at the location chosen for insertion of the atrial portal (i.e., the entry location), and the needle and/or introducer then inserted directly into the left or right atrium in the center of the purse-string suture.

In certain embodiments, insertion of a needle (i.e., an introducer needle) into the atrium may be performed after administering heparin. Also, in certain embodiments, insertion of an introducer needle into the atrium may be performed with the patient in Trendelenburg position to maintain elevated atrial pressure during cannulation. Once the tip of the introducer needle is in the atrium, a guide wire can be positioned into the atrium through the needle. This wire may be used to maintain access to the atrium. In certain embodiments, the guide wire may be a long flexible J-tipped guide wire with distal flexible tip. Or, other guide wires may be used.

In certain embodiments, and as described in more detail herein, the atrial portal may be placed in position through the atrial wall over a dilating introducer (e.g., a graduated sheath). In certain embodiments, the dilating introducer may have a flexible tip. For example, in certain embodiments, a dilating introducer may be placed over a guide wire that has been inserted in the atrium, and pushed into the atrial wall to expand the opening in the atrial wall to allow placement of a left atrial portal through the wall.

In certain embodiments, and as described in more detail herein, the atrial portal may comprise an expandable member or members that may be used to secure the distal end of the atrial portal into the atrial wall. The expandable member may, in alternate embodiments, be expanded with air or another gas, or a fluid (e.g., saline). In certain embodiments, the expandable member may comprise a balloon or inflatable member. In an embodiment, the expandable member or members is fashioned as a cap at the distal end of the atrial portal.

In certain embodiments, the atrial portal (and pericardial portal) and parts of the atrial portal and/or pericardial portal that contact the interior of the atrium or the heart are heparin coated. In certain embodiments, the expandable member or members is heparin coated. In certain embodiments, the dilating sheath and atrial cap is heparin coated.

For example, there may be an expandable member positioned at, or very close to the distal end of the atrial portal, such that when the atrial portal is inserted into the atrium, this expandable member constitutes an internal expandable member. In this way, once the atrial portal is in position, the internal expandable member may be inflated (e.g., with saline) to maintain traction on the internal surface of the atrial wall, such that the atrial portal cannot be pulled proximally out of the opening once the internal expandable member has been expanded.

In certain embodiments, the atrial portal may also comprise an external inflatable and/or expandable member (i.e., an expandable member that is positioned external to the atrium when the atrial portal is inserted in the atrial wall). The external inflatable and/or expandable member may be positioned more proximally along the atrial portal such that when the atrial portal is inserted into the atrium, this expandable member constitutes an external expandable member. In this way, once the atrial portal is in position, the external expandable member may be inflated (e.g., with saline) to maintain traction on the external surface of the atrial wall, such that the atrial portal cannot be pushed distally further into the opening once the internal expandable member has been expanded. In this way, the internal expandable member and the external expandable member can secure the atrial portal in the atrial wall. In an embodiment, the external expandable member is an inflatable member. Alternatively, solid flaps or other elements that extend from the cap may be used.

In an embodiment, both the internal expandable member and the external expandable member are part of a cap at the distal end of the atrial portal.

In certain embodiments, the atrial portal, introducer needle, and the dilating introducer may be used as a single unit to insert the atrial portal into the atrium. The single unit may provide increased stability for procedures that have significant lateral or horizontal torque placed on the device. In this embodiment, there may be a tapered suture tie area on the distal end of the atrial portal for securing the device to the atrium. After a securing suture (e.g., purse-string suture) has been placed, the unit (i.e., atrial portal, introducer needle and dilating introducer) can be positioned (e.g. under direct visual access by endoscopy) onto the surface of the atrium, and within the identified entry location (e.g., in the center of the purse-string suture) with the needle withdrawn into the dilator. The needle can be advanced into the atrium. Next, a guide wire may be advanced into the atrium. The needle may then be partially withdrawn and the entire unit advanced to allow the dilating introducer and distal portion of the atrial portal to be inside the atrial cavity. The purse string suture may then tightened, as is described in more detail herein, thereby securing the atrial portal to the left atrium. In an embodiment, expandable members on the distal end of the atrial portal may be inflated, thereby securing the distal tip of the atrial portal into the left atrium. The guide wire, introducer needle, and dilating introducer may then be withdrawn.

At this point, i.e., once the atrial portal is introduced into the atrium, various tools and/or devices may be inserted into the atrium.

In certain embodiments of the devices, methods and systems of the present invention, heparin is administered to prevent thrombus formation within the atrium. For example, a left atrial portal can be perfused with heparinized saline to prevent thrombus formation within the device.

Atrial Portal Procedures a. Ablation Procedures in the Left Atrium

Currently, performing ablation in the left atrium is a difficult procedure, that requires extensive training to perform, and that is not without significant risk to the patient, especially for the targeted patient population (i.e., patients who have cardiac disease). Access to the left atrium during percutaneous catheter ablation typically has been performed by passing a needle across the atrial septum (i.e., the wall between the left and right atrium), positioning a wire from the right to the left atrium, and then dilating an opening between the two atria large enough to allow manipulation of catheters inside the left atrium. This can be a challenging procedure, and consequently, is performed by relatively few physicians. For example, ablation procedures to treat atrial fibrillation generally require two atrial septal defects: one for the ablation catheter and another for an interrogation electrode. At the completion of this type of procedure, the defects in the septum remain, allowing the inappropriate flow of blood between the left atrium and the right atrium until the defect closes, which generally requires about two to four months. Additionally, repeat ablation procedures using the trans-septal approach can be associated with increased complications due to the scar tissue that has formed from prior trans-septal access.

Embodiments of the devices, methods and systems of the present invention allow for direct cannulation of the left atrium to perform ablation procedures. Direct cannulation of the left atrium avoids the need to cross the intra-atrial septum, thereby eliminating the technical challenge of crossing the septum to gain access to the left atrium. Also, the risk of post-procedure atrial septal defects is significantly reduced, as no defect is made in the septum during the surgery.

Additionally, direct cannulation of the left atrium allows the placement of larger ports and more sophisticated instruments into the left atrium. Once the left atrial portal is in place, a physician can insert an ablation tool to perform procedures (e.g., ablative procedures to treat atrial fibrillation) inside of the heart with less risk and less complexity.

b. Heart Failure Sensors

In patients who have a failing heart, implantation of therapeutic devices such as pacemakers and/or implantable cardioverter defibrillators (ICDs) is a generally common treatment, as such devices may ameliorate symptoms so as to delay and/or prevent the patient requiring a ventricular assist device. Current devices may incorporate "heart failure" sensors, which can for example, measure transthoracic impedance as a measure of worsening heart failure. Devices that measure direct pressure have been developed, although these devices primarily measure pressure in the right atrium, right ventricle or right ventricular outflow tract and infer changes in right sided pressure as a reference to left sided pressures. As a result, there is not always be a direct comparison of left sided filling pressures.

The devices, methods and systems of the present invention may, in certain embodiments, be used for measurement of left atrial pressure. Although measurement of left atrial pressure by a trans-septal puncture from a superior subclavian approach has been explored, the procedure is complicated and therefore rarely, if ever, performed. For example, the trans-septal approach adds another "lead" within the vascular structures, increasing the risk for stenosis or occlusion of the vein. Also, the vein used for implantation may not be of appropriate size to allow placement of all of the required leads. For example, many implants use a biventricular device which has three leads, and thus, require a large vein for introduction.

Direct cannulation of the left atrium using the devices, methods and systems of the present invention can eliminate the difficulty of crossing the intra-atrial septum from the superior approach. Direct cannulation can reduce difficulties associated with emplacing multiple leads within the vascular structures. Using a left atrial portal of the present invention to provide access to the left atrium can allow placement of left atrial pressure sensors which have a greater accuracy in assessing left sided filling pressures. The lead can then be tunneled back either from an epigastric access, or via the pericardium in a superior fashion to the generator pocket (generally emplaced subcutaneously).

In certain embodiments, the devices, methods and/or systems of the present invention may include a sensor "button" that uses a pressure sensor and a wireless communication with the device. In this way, remote monitoring of the atrial pressure may be performed. Also, combination lead therapies that contain sensors and the ability to pace the left atrium may be provided using the devices, methods and/or systems of the present invention.

c. Left Atrial Appendage Therapies

Atrial fibrillation is responsible for about 15% of all strokes (Sandercock et al., BMJ 1992; 305:1460-5; Wolf et al., Am. Heart J., 1996; 131:790-5; and Kannel et al., Am. J. Cardiol., 1998; 82:2 N-9N) and evidence suggests that about 90% of these strokes are related to thrombus formation in the left atrial appendage (Aberg et al., Acta Med. Scand., 1969:185:373-9; Stoddard et al., J. Am. Coli Cardiol. 1995; 25:452-9; and Blackshear and Odell, Ann. Thorac. Surg., 1996:61:755-9). The PLAATO® device has been developed to percutaneously close the left atrial appendage (LAA) and exclude it from intra-cardiac circulation thereby potentially reducing the risk of embolic thrombus migration and stroke. This is less invasive than cardiac surgical removal of the LAA and may decrease the risk of stroke in those patients with atrial fibrillation (AF). However, to emplace the PLAATO® device, physicians must gain access to the left atrium via the atrial septum, which, as described previously, can be associated with complicating factors.

The devices, methods and systems of the present invention can, in certain embodiments, provide direct access to the left atrium for placement of these devices. Additionally, because the left atrial appendage can be directly visualized using pericardioscopy, procedures, instrumentation and devices for emplacing an occlusive device around the base of the LAA from the epicardium can be facilitated with endocardial manipulation of the LAA. For example, the left atrial portal can be adjusted in size to accommodate the device being utilized. The additional ability to access the LAA via the pericardial sac and from the endocardial aspect may decrease the complexity of LAA device deployment. Also, ability to access the LAA via the pericardial sac may decrease the complexity of LAA occlusion and excision surgically.

d. Valve Therapies

There is a need to improve methods for treating both mitral and aortic valve diseases. Currently, endovascular placement of valves, either by percutaneous femoral access or trans-apical access may be used.

The devices, methods and systems of the present invention may be used to provide access to the left atrium in a minimally invasive fashion, such that valve disorders may be treated without arresting the heart. For example, in one embodiment, the left atrial portal can be positioned and with the use of fluoroscopy or other types of imaging (e.g., intracardiac and epicardial ultrasound), positioned such that valves in the heart (e.g., the mitral and aortic valves) are visualized and accessed to perform structural repairs.

For example, using the devices, methods and/or systems of the invention, the mitral valve annulus may be reduced internally by positioning a reducing device, such as a band, a ring or suture material in the posterior mitral valve annulus. In this way, one can reduce the annulus and improve mitral annular dilatation which causes mitral valve regurgitation. Such direct manipulation of the posterior mitral valve annulus may be performed using a left atrial portal of the present invention. In certain embodiments, imaging guidance, either via an ultrasound probe positioned within the left atrial portal or via epicardial ultrasound, is used to visualized the valve. For example, using ultrasound, the amount of reduction can be determined in real time because the heart is beating and functioning during the reduction. The degree of reduction can be adjusted based on the improvement of the valve function. Using the devices, methods and systems of the present invention such valve therapies may be performed on the beating heart, endoscopically, and without cardiopulmonary bypass.

Additionally or alternatively, placement of expandable mitral valve and aortic valve prosthesis may be performed using the devices, methods and systems of the present invention. In an embodiment, after the left atrial portal is positioned in the left atrial wall, a guide wire within the lumen of the left atrial portal may be threaded through the left atrium and into the valve to be treated. Next, devices (e.g., replacement valves) may be positioned in the valve as required. Alternatively, devices necessary to deploy percutaneous valve technology through the left atrial portal may be used. Again, using the devices, methods and systems of the present invention such valve therapies may be performed on the beating heart, endoscopically, and without cardiopulmonary bypass.

e. Cardiac Assist Devices

Patients with acute post-cardiotomy heart failure (heart failure after open heart surgery) or chronic, end-stage heart failure may require mechanical support with an "artificial heart". These devices, like the NOVACOR® (World Heart, Salt Lake City, Utah) or HEARTMATE® (Thoratec, Pleasanton, Calif.) help the heart pump blood when it is unable to keep up with the demands of the body. Traditionally, placement of these devices has required median sternotomy and cardiopulmonary bypass. Cannulas to connect the pump to the heart must be inserted into the right atrium and pulmonary artery for right heart support and in the left atrium and aorta for left heart support.

The devices, methods and systems of the present invention may be used to provide access to the left or right atrium in a minimally invasive fashion, such that the left atrium can be cannulated for access by an artificial heart. For example, using the devices, methods and systems of the present invention, a cannula may be placed in the left atrium to drain blood from the lungs into a heart pump. Also using the devices, methods and systems of the present invention, another return cannula or bypass graft may be inserted into the femoral artery, the subclavian artery, the aorta, or other artery. The blood may then be pumped from the left atrium to the systemic arterial system with the left sided cardiac assist device, a "blood pump" positioned outside the heart.

In yet other embodiments, the devices, methods and systems of the present invention may be used to insert a small, tubular centrifugal pump through the left atrium and into the ascending aorta. By placing this type of pump in the left atrium or left ventricle, blood can be pumped from the left atrium and left ventricle out the aorta to support the left heart. The entire pump can be contained within the failing heart as a "bridge to recovery" to be removed when the cardiac function recovers, or as a "bridge to transplantation" to be removed upon cardiac transplantation. The IMPELLA® device (Abiomed, Danvers, Mass.) is an example of such device.

Because such centrifugal pumps are currently emplaced via percutaneous access, there may be size constraints on the size of the pump that can be used as the pump must be of a caliber small enough to fit through the femoral artery. Such limitations on the size of the pump can result in limitations on the flow rate that can be achieved. Using the devices, methods and systems of the present invention, a larger device can be placed through the left atrium, thereby allowing higher flow rates and added cardiac support.

Alternatively, the devices, methods and systems of the present invention may be used to emplace a similar centrifugal pump within the right atrium and right ventricle to pump blood from the right atrium and right ventricle out the pulmonary artery to the lungs.

Emplacement of Cardioscopic Atrial Pursestring (CAP)

The atrial portal of the present invention provides a conduit for direct access to the atrium. In order to maintain hemostasis and prevent air entrainment when using the atrial portal for surgical access to the heart, the present invention comprises devices, methods and systems to secure the atrial portal in the wall of the atrium in an manner such that blood is not lost from the atrium via the incision used for insertion of the atrial portal in the left atrium. As described above, a suture may be positioned near the entry location in the atrial wall. The suture (or sutures) may be used to secure the atrial portal in the heart wall. Also, the suture may be used to close the entry location (i.e., the orifice made in the atrium) after the atrial portal is removed.

In certain embodiments, a suture (or sutures) may be positioned around the circumference of the entry location to seal the atrial tissue around the device. For example, in certain embodiments, a suture may be positioned in a purse string manner. In certain embodiments, the purse-string suture can be placed with traditional endoscopic needle drivers, or with an automated needle driver (Endostitch, Covidian, Dublin, Ireland). The purse-string also occludes the opening in the left atrium at procedure completion.

In certain embodiments, the present invention comprises devices, methods and systems for placing the purse-string automatically. For example, in some embodiments, the cardioscopic atrial purse string (CAP) device may be placed over the atrial portal and advanced to the atrial surface. Upon deployment, a suture on a needle may then be passed into the atrial epicardium, and then the suture may be passed outward (i.e., out of the atrial wall) to be retrieved. By deploying two to four needles into the myocardium in a circular pattern, the purse-string may be developed and the retrieved ends can be used to secure the atrial portal to the left atrial epicardial surface. As the purse-string is tightened, by pulling proximally (i.e., away from the heart) the atrial wall may be tightened around the atrial portal, thereby preventing loss of blood from the atrium, and the entry of air into the heart.

Upon completion of the surgical procedure, and removal of the atrial portal, the suture may be further tightened (again by pulling the sutures distally) and the strings tied to permanently secure the defect in the atrium.

Pericardial Portal

Other embodiments of the present invention may comprise a pericardial portal. Similar to the atrial portal, the pericardial portal can provide access to the pericardial space. As described in more detail herein, such access can allow for insertion of other devices (e.g., surgical tools, electrodes, ablation elements and the like) into the pericardial space, as for example, for use with a atrial portal. As described in more detail herein, in certain embodiments, the pericardial portal allows direct access, without continuous visualization, to the epicardial surface of the heart.

In an embodiment, the distal end of the pericardial portal is shaped to facilitate positioning and securing of the portal on the cardiac side of the pericardium. In certain embodiments, the distal end is not completely flush along the entire circumference, but is tapered such that it extends outward for at least part of the circumference. Also, in certain embodiments, the pericardial portal has a substantially flattened distal end.

In certain embodiments, the portal may have side access ports that allow lateral access into the pericardial space. These side ports may include radiographic markings to facilitate positioning the side ports in the pericardial space.

The pericardial portal may be inserted by the surgeon into the patient via the diaphragm either at the subxyphoid location or at the transdiaphragmatic location in the central tendon of the diaphragm. Or, other routes for inserting the pericardial portal may be used depending upon the procedure to be performed.

Once in place, direct access inside the pericardial sac may allow various epicardial procedures to be performed. In addition to facilitating procedures performed with the atrial portal, such procedures may include epicardial mapping and ablation, epicardial imaging (ultrasound, direct visualization using flexible scopes), placement of epicardial pacing leads and other epicardial technologies. The pericardial portal significantly reduces the concern for cardiac injury, while allowing pericardial access using existing methods and instrumentation. Using the pericardial portal of the present invention can allow for improved manipulation of cannulas and other devices in the pericardial sac or the heart.

Examples of therapies that may be performed using the pericardial portal of the present invention include the following therapeutic procedures.

a. Pacing Therapies

Pacing in patients with sick sinus syndrome is usually performed from the right atrium by endocardial/transvenous lead placement. However, using this approach, intra-atrial conduction delay may prevent correct left atrial/left ventricular synchrony. Such delay may lead to inadequate left ventricular filling and reduced cardiac output.

Pacing of the left atrium can restore this synchrony which may be of significant benefit in the heart failure patient. For example, it has been shown that pacing of the left atrium can reduce acute episodes of atrial fibrillation after cardiac surgery. Additionally, it is believed that left atrial pacing may also help prevent long-term episodes of atrial fibrillation.

Currently, left atrial pacing may be achieved by placing leads on the epicardial surface of the left atrium at the time of open heart surgery, or during transvenous lead placement into the coronary sinus. However, it has been found that the transvenous approach (using either active or passive fixation leads) can have an increased risk for dislodgement of the leads. Also, there may often be a lack of suitable veins to the left atrium off the coronary sinus, thereby resulting in the need for surgical placement by thoracotomy or sternotomy (i.e., cutting into the pleural cavity or through the breast bone).

Biventricular pacing devices may be required for patients with advanced heart failure. Such biventricular pacing devices generally require placement of leads on the mid-lateral left ventricle in a vein off the coronary sinus from a transvenous approach. The anatomy of the coronary sinus is variable and may not have adequate veins in the mid-lateral position, or the veins may contain a stenosis, or have significant tortuosity so as to prevent placement of a left ventricular pacing lead. Surgical placement of a left ventricular lead may be performed, but requires a thorascopic or thoracotomy approach.

Also, pediatric patients who need pacing therapies usually require epicardial lead placement. Such epicardial leads are generally placed using a thoracotomy with most leads placed on the right atrium and right ventricle. Chronic right ventricular pacing can lead to left ventricular dysfunction in a subset of patients.

As described in more detail herein, in various embodiments of the devices, methods and systems of the present invention, the pericardial portal of the present invention may be used for placement of leads on the epicardial surface of the heart. Use of the pericardial portal and associated methods and systems of the present invention can allow for placement of leads where currently lead placement technologies are limited by lack of suitable anatomy and eliminates the need for large incisions in the chest (e.g., thoracotomy).

b. Epicardial Ablation

Arrhythmias may have epicardial foci that are unable to be ablated from an endocardial approach. This leaves the option for either medical therapy or epicardial ablation. Epicardial ablation is currently performed only at specialized centers primarily due to the technical difficulties in gaining access to the pericardium. Current techniques have an increased risk for epicardial vascular damage or chamber perforation due the lack of significant space between the pericardium and the heart.

As described in more detail herein, in various embodiments of the devices, methods and systems of the present invention, the pericardial portal of the present invention may be used to provide access for an electrophysiologist to perform epicardial ablation without the increased risk currently associated with pericardial access.

c. CorCap

The CorCap device is a mesh sock that may be placed on the epicardial surface of the heart to restrict the overall volume of the heart so as to treat heart failure which can result from dilation of the heart. The CorCap device does not require suturing to the epicardium, but does require access to the heart by thoracotomy.

As described in more detail herein, in various embodiments of the devices, methods and systems of the present invention, the pericardial portal of the present invention may be used for deployment of a CorCap (or similar device) into the pericardial space. The CorCap may then be positioned using thorascopic tools, thereby eliminating the need for thoracotomy in these high risk patients.

Emplacement of a Left Atrial Portal

FIG. 1 illustrates the surface anatomy of a person with the location of the cardioscopic port. A relatively small (e.g., 2-3 cm) incision in the midline below (caudad to) the xyphoid allows access to the abdomen within the peritoneum or to the pericardial sac outside the peritoneum.

As illustrated in the figures, the cardioscopic (e.g., atrial) portal, or pericardial portal, may be positioned through the peritoneum and through the central tendon of the diaphragm. However, as is known by those of skill in the art, other routes may be used provide access to the pericardial sac via a sub-xyphoid location. For example, in one embodiment, a pericardial portal or atrial portal can be inserted into the abdomen through a small (e.g., about 1-3 cm) incision in the abdominal wall just below the xyphoid, and positioned adjacent to the diaphragm. Next, a cutting tool at the distal end of the pericardial portal 2 may be used to make a defect (i.e., opening) in the diaphragm.

The pericardial portal and/or atrial portal may then be threaded though the abdominal wall until the pericardium is identified. For example, the pericardium may be identified under direct vision behind the xyphoid and outside the peritoneal cavity or visualized with endoscopic guidance and an incision made in the pericardial sac for positioning of the atrial portal or the pericardial portal. Access to the epicardial surface of the heart via this sub-xyphoid approach enables procedures on the surface of the heart described herein.

In FIG. 1, a pericardial portal 2 is seen in the upper abdomen 4 but not in the thorax 6. A similar entry is performed for the atrial portal (not shown).

Figure 2:
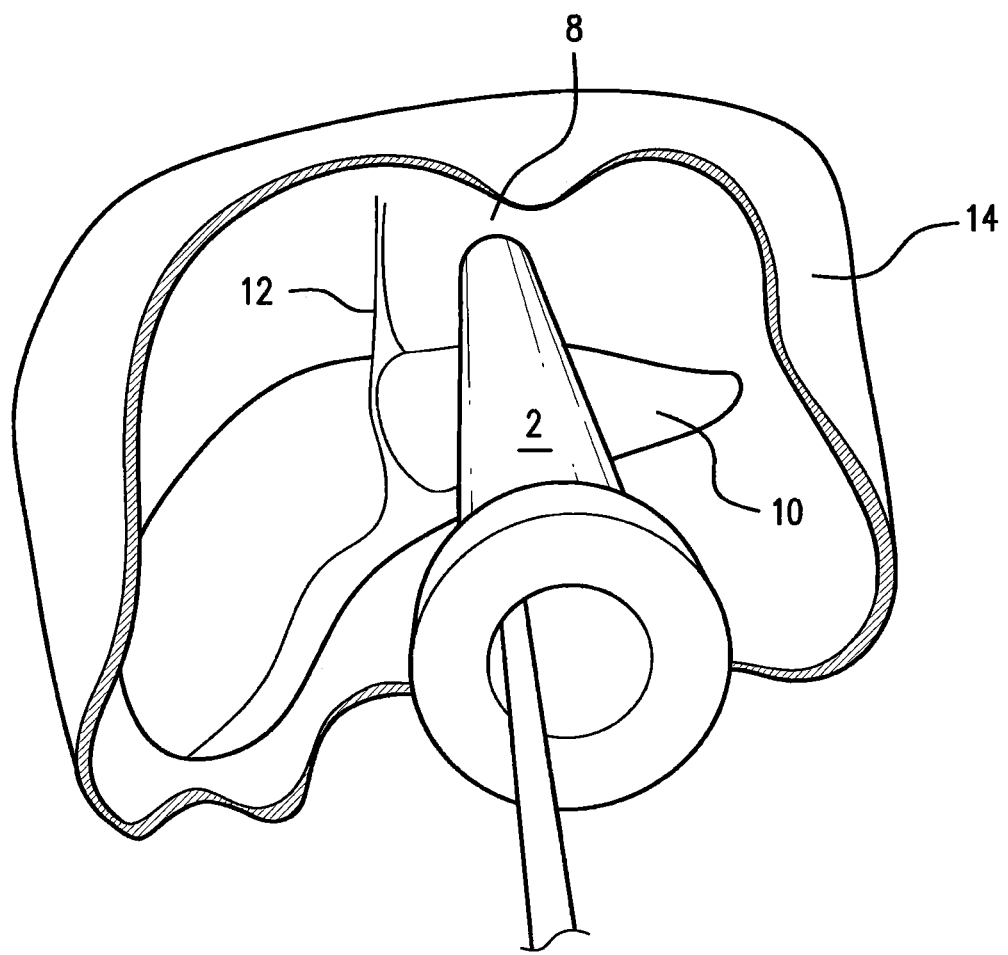
FIG. 2 illustrates a pericardial portal within the peritoneal cavity in accordance with an embodiment of the present invention.

In FIG. 2, the pericardial portal 2 is pictured within the peritoneal cavity. The pericardial portal 2 is shown traversing the abdomen and penetrating the diaphragm in the central tendon 8, anterior to the left lobe of the liver 10 and to the left (i.e., anatomically) of the falciform ligament 12. The diaphragm 14 is depicted.

In certain embodiments, as where using a pericardial portal, procedures may be performed where the pericardial sac is not opened, but the surgery or positioning of a therapeutic device or tool (e.g., defibrillator pads) is done on the outer surface of the pericardium. The pericardial portal may be positioned via a surgical defect in the central tendon of the diaphragm such that the pericardial space is elevated and the distal end of the pericardial portal can be positioned behind the pericardial sac. The distal end of the pericardial portal may create a temporary space between the pericardium and adjacent mediastinal structures. This allows extra-pericardial surgical procedures to be performed.

Alternatively, a cutting tool that extends from the distal end of the pericardial portal or the left atrial portal can be used create an incision in the pericardial sac allow for the distal end of the portal to be inserted into the pericardial sac and positioned in the pericardial space so as to create a temporary space within the pericardium (i.e., the pericardial sac). Positioning of the distal end of the portal within the pericardial sac allows surgical procedures to be performed directly on the epicardial surface (i.e., the surface of the heart).

Each of the stages of positioning an atrial portal, or a pericardial portal may utilize an endoscope positioned within the lumen of the portal. In this way, the posterior side of the heart and/or other organs or body tissues of interest can be directly visualized using a viewing device (e.g., camera) at the proximal end of the endoscope.

There are a variety of routes that may be used to access the organ or tissue of interest. In certain embodiments, access to the pericardium is via an incision below the xyphoid process and an incision in the diaphragm. In other embodiments, access to the pericardium may be obtained by a transcervical pathway. For example, access to the pericardium and the intrapericardial space may be gained by an incision above the clavicles and the sternum, by creating a space in the pre-tracheal fascial plane anterior to the trachea and posterior to the great vessels and cardiac structures and between the pleural spaces. Alternatively, the pericardium may be accessed by creating a window in the pericardium behind the great vessels and superior to the dome of the left atrium. The devices, methods and systems of the present invention allow access to the heart from the posterior side of the patient, without interference from other organs in the thoracic cavity or the spine.

Figure 3:
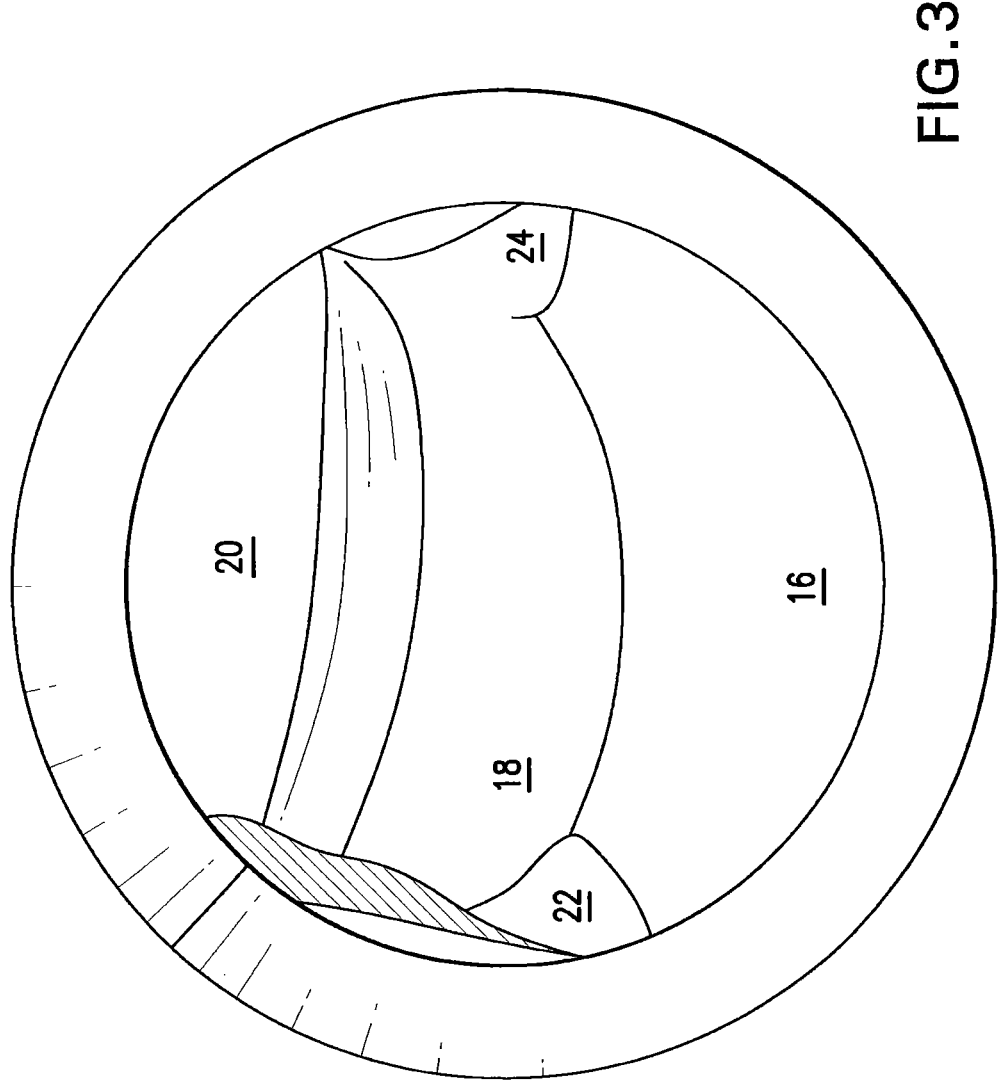
FIG. 3 illustrates the view at the distal end of a pericardial portal in accordance with an embodiment of the present invention.

FIG. 3 illustrates an embodiment of a view at the distal end of a pericardial portal 2 or the distal end of an atrial portal. The view may be provided via an endoscope that is positioned within the lumen of the pericardial portal and/or an atrial portal. The view is within the pericardial sac. The posterior pericardium 16 is seen behind the posterior left atrium 18. The coronary sinus 20 is seen close to the end of the pericardial portal 2. The right 22 and left 24 inferior pulmonary veins are illustrated. The anatomical structures are seen while the heart is beating and supporting normal circulation.

Figure 4:
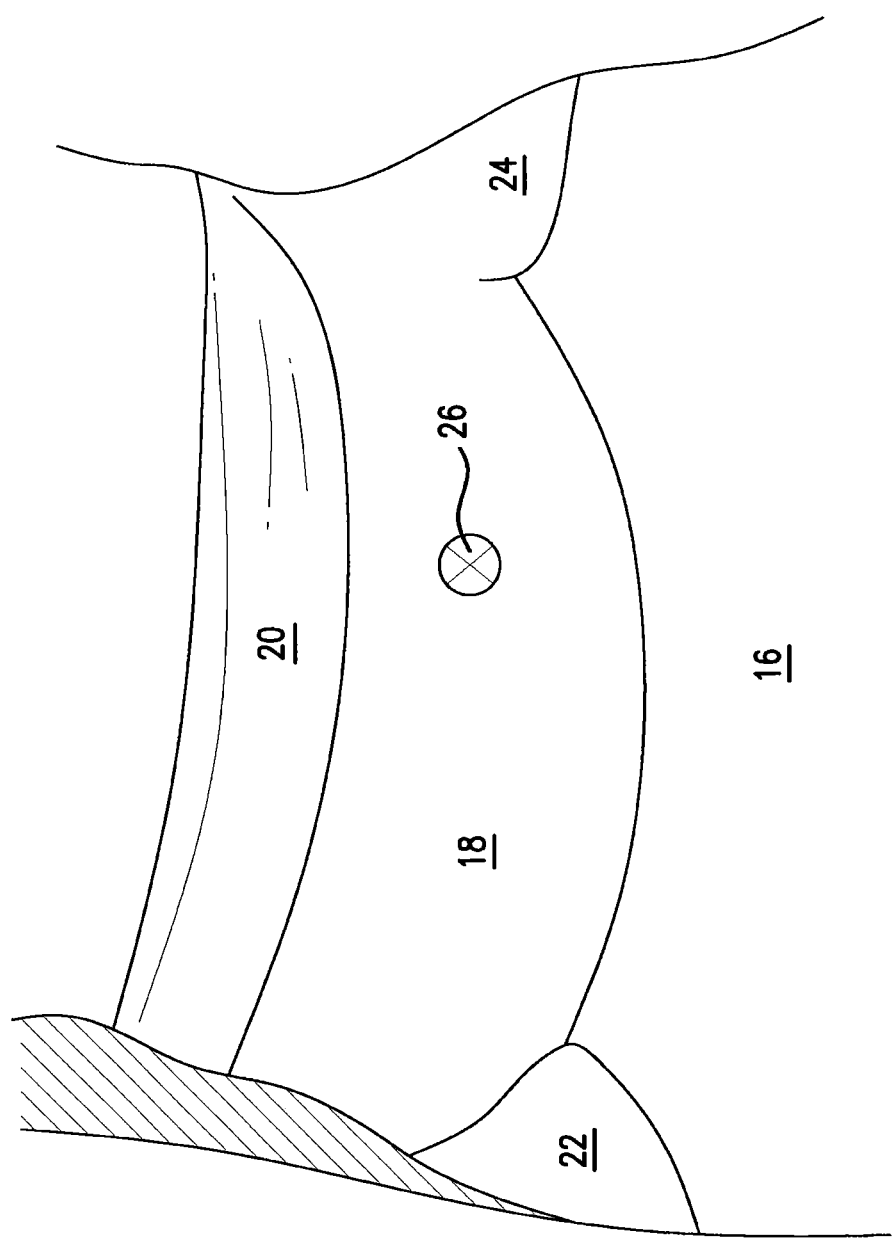
FIG. 4 illustrates a similar view of the pericardial anatomy as seen in FIG. 3, showing an entry location for placement of a left atrial portal in the left atrial wall in accordance with an embodiment of the present invention.

FIG. 4 illustrates a similar view of the pericardial anatomy as seen in FIG. 3. The entry location 26 for placement of a left atrial portal is identified. The entry location (i.e., the position on the heart for insertion of the left atrial portal through the atrial wall) may differ depending upon the type of procedure being performed. For example, the left atrial portal may be positioned closer to the left inferior pulmonary vein 24 for aortic valve procedures but closer to the right inferior pulmonary vein 22 for mitral valve procedures.

Figure 5:
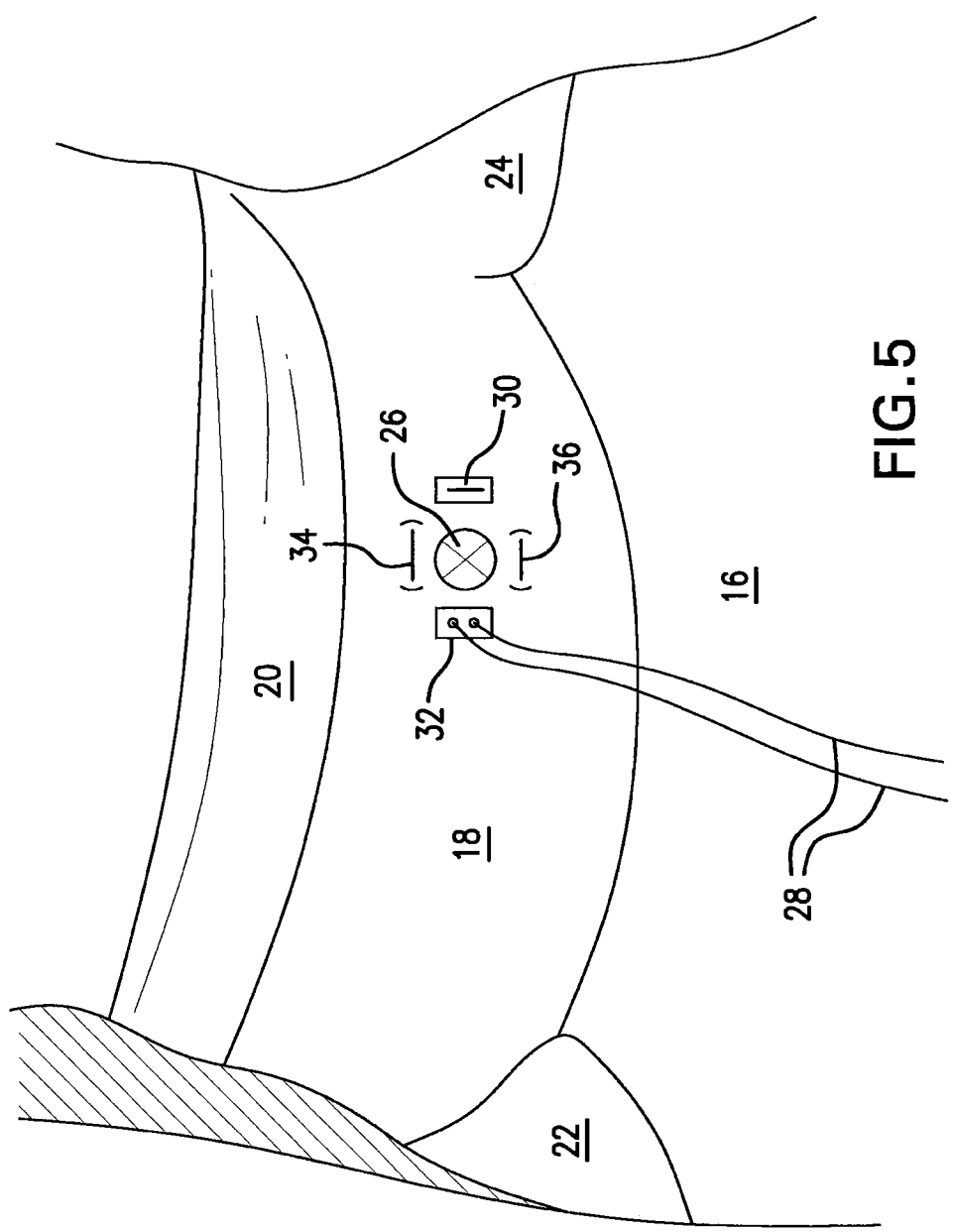
FIG. 5 illustrates a purse string suture that has been placed around an entry location for a left atrial portal in accordance with an embodiment of the present invention.

FIG. 5 illustrates an embodiment of a purse string suture 28 that has been placed around the left atrial portal position 26. The suture 28 can be placed with endoscopic needle driver and other endoscopic suturing instrumentation. Cotton pledgets 30,32 may be used to improve the seal for the atrial portal in the left atrium, as well as to prevent trauma to the atrial tissue. Although 2 pledgets are shown, the number of pledgets may be varied as required by the size of the portal. For example, in some cases no pledgets are required, whereas in other cases more than 2 pledgetts are required. Also, other types of support elements may be used. The suture passes through one pledget 30. The suture is threaded inside the left atrial wall between 30 and 34 and between 30 and 36. The suture is seen on the atrial surface at 34, 36. The suture is then threaded inside the left atrial wall between 34 and 32 and between 36 and 32, and then both ends of the suture are passed through another pledget 32 directly opposite the first pledget with respect to the entry location 26 on the surface of the left atrium 18. When the suture is tightened, the pledgets can approximate and close the purse string around the left atrial portal location 26 so as to provide hemostasis and secure the left atrial portal to the left atrial surface 18.

FIG. 6 illustrates a left atrial portal 38 passing through the outer surface 18 of the left atrium and secured by the purse string suture 30, 32, 34, 36. As illustrated in FIG. 6, the proximal end of the left atrial portal 38 may exit out of the abdomen of the patient.

Also depicted in FIG. 6 is cardioscopic tourniquet 40 that can be used to secure the suture 28 around the left atrial portal 38. In an embodiment, the tourniquet may be a Rommel tourniquet. The cardioscopic Rommel tourniquet should be sturdy enough to provide sufficient resistance to close the purse string as the suture 28 is tightened. Also, the tourniquet must also be of sufficient length for the proximal end of the tourniquet to be manipulated by the physician. In one embodiment, the cardioscopic Rommel tourniquet 40 may be made of latex-free plastic and is about from 10 to 30, 12 to 28, 14 to 26, 16 to 24, or 18 to 22, or about 20 inches in length and has an internal diameter of 1.0 to 3.0, or 1.5 to 1.8, or about 2.0 to 2.5 mm.

FIGS. 7A-7D illustrate an embodiment of a suture capture device 47 that may be used with a left atrial portal of the present invention. The suture capture device 47 may be passed through the cardioscopic Rommel tourniquet 40 (FIG. 7A) to capture the suture 28. The suture capture device may then be used to pull the suture into the distal end the tourniquet (FIG. 7B), through the tourniquet (FIG. 7C), and out the proximal opening of the tourniquet (FIG. 7D) where tension can be applied to the suture 28 to secure the purse string 30,32,34,36 against the cardioscopic Rommel tourniquet 40.

FIG. 8A illustrates a pericardial portal 2 with the cardioscopic Rommel tourniquet 40, a left atrial portal 38, and an endoscope 44 emerging from the distal opening of the pericardial portal. FIG. 8A illustrates an embodiment where the tourniquet 40 is being used by a physician to secure the purse string 28 around the left atrial portal. Also, shown in FIG. 8A is an endoscopic camera 44 attached to a video head 46 outside the proximal opening of the pericardial portal 2.

In some cases, where the pericardial portal 2 may not have an adequate opening to accommodate all the instruments required, a different access for placement may be used. This embodiment is depicted in FIGS. 8B-8D.

Figure 8B:
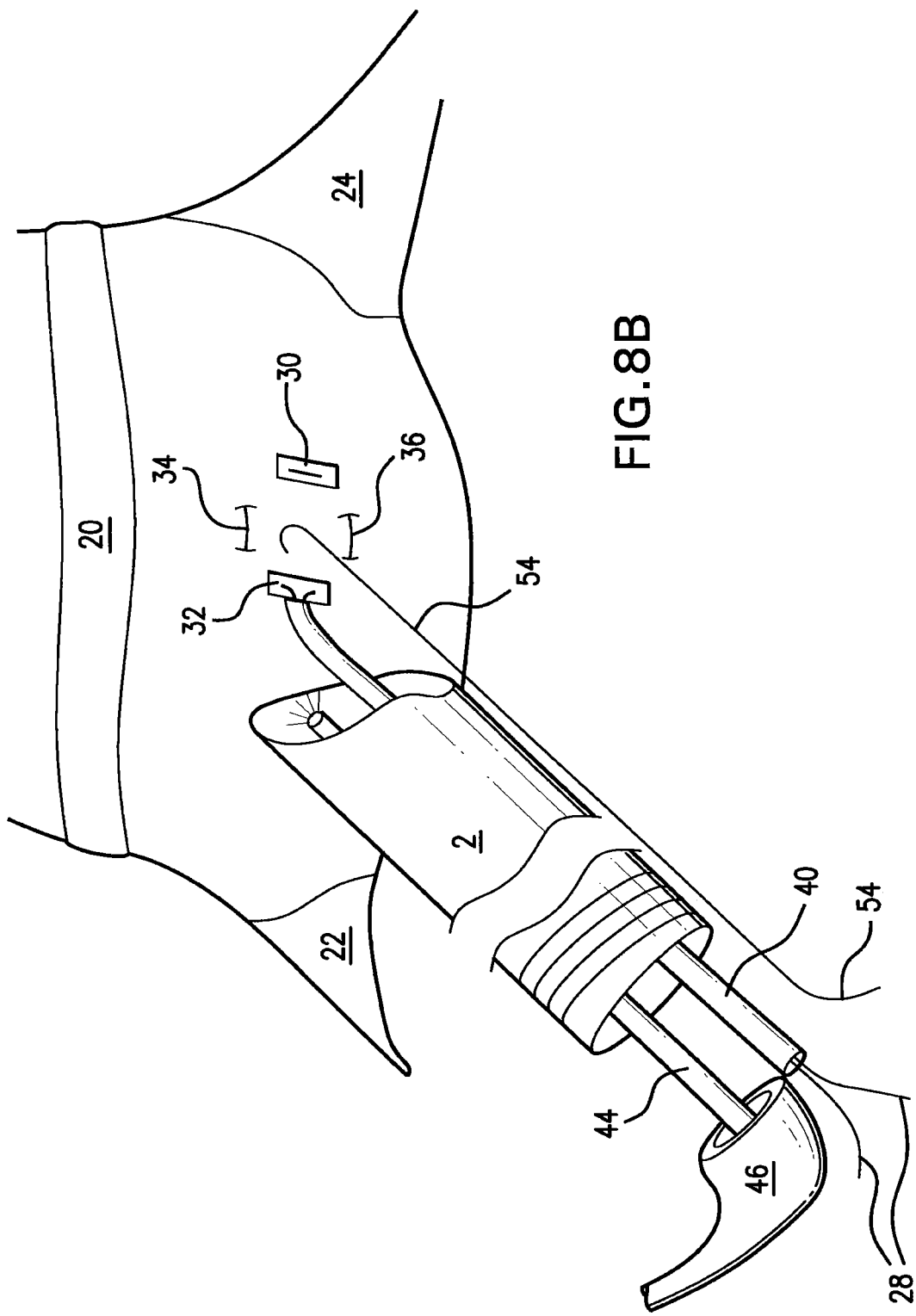

Thus, FIG. 8B demonstrates the pericardial portal 2 with a cardioscopic Rommel tourniquet 40, and an endoscope 44 emerging from the distal (and proximal) openings of the pericardial portal. In this embodiment, a separate guide wire 54 may be placed outside of the pericardial portal 2 and into the pericardial space. The guide wire may then be inserted into the entry location selected for insertion of the left atrial portal into the left atrium (shown in FIG. 8C as centered within the purse string suture 30,32,34,36). The guide wire 54 can be placed through the same access as the cardioscopic portal 2 or through a secondary access using an introducer needle positioned outside the pericardial portal and into the left atrium under endoscopic visualization of the endoscope within the pericardial portal.

Figure 8C:
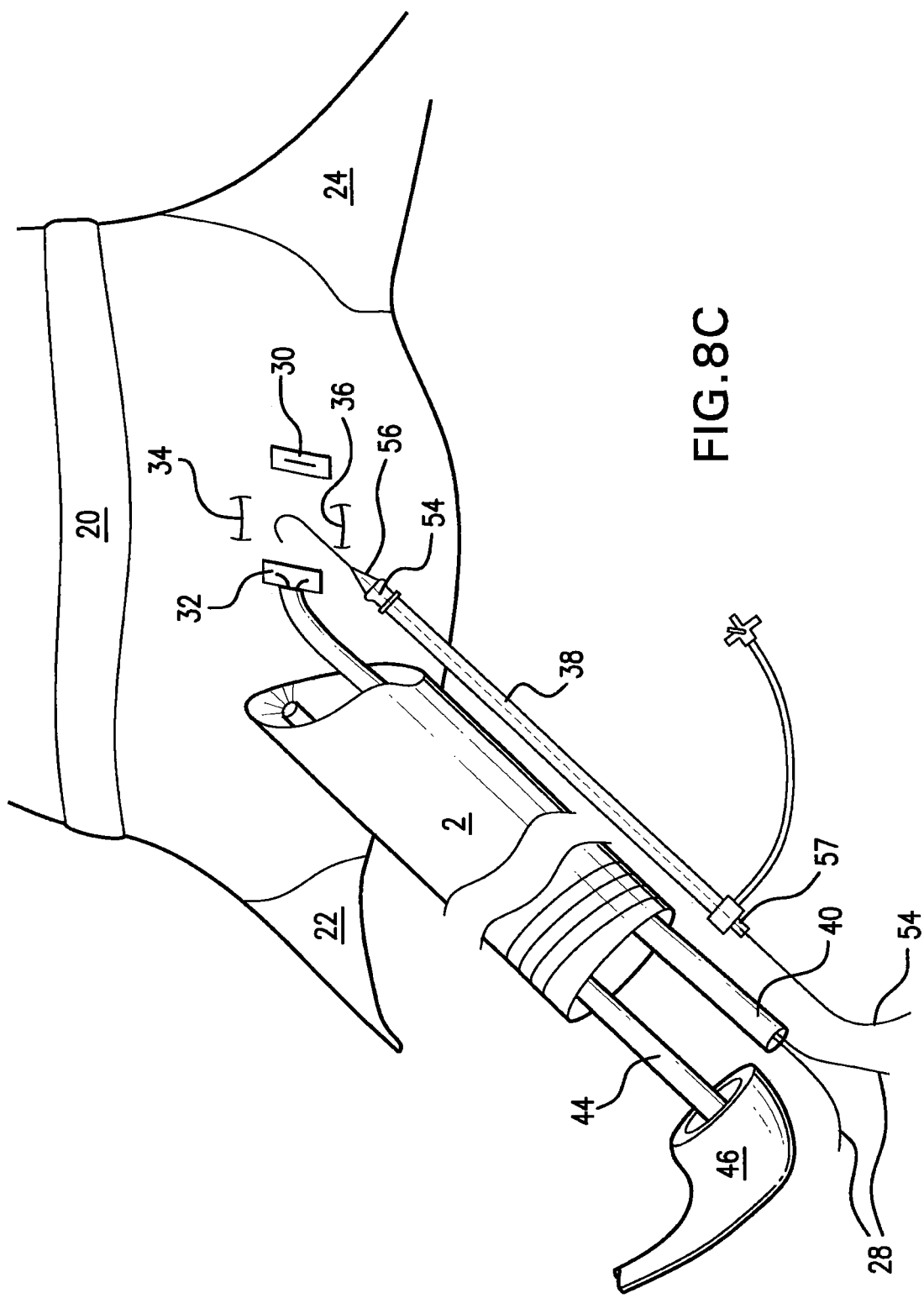
Figure 8D:
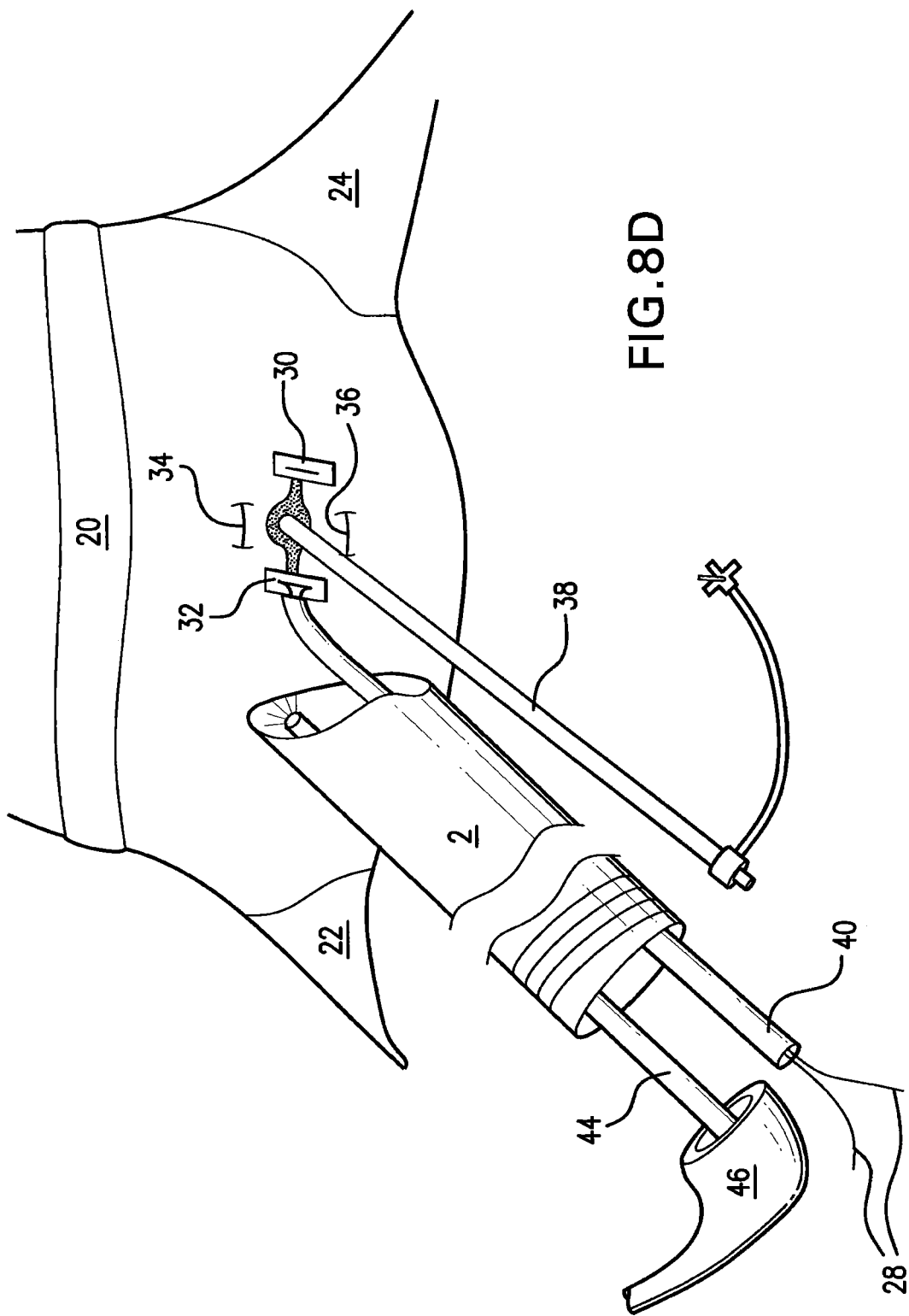

FIG. 8C shows the left atrial portal 38 with a dilating introducer 56 positioned at the distal end of the left atrial portal. The dilating introducer 56 can be used to increase the opening in the atrial wall as the left atrial portal is inserted into the entry location by manipulating the proximal end 57 of the introducer. As shown in FIG. 8C, the left atrial portal can be advanced along the guide wire 54 into the pericardial space and until the distal end of the left atrial portal is in adjacent to the entry location. Next the left atrial portal can be threaded over the guide wire and inserted into the left atrial wall as described in more detail in FIGS. 9A-9H. Final placement of the left atrial portal 38 when external to the pericardial portal 2, is shown in FIG. 8D.

FIGS. 9A-9H demonstrate placement of a left atrial portal in the left atrial wall. In FIG. 9A, the purse string has been positioned and the pledgets 30,32 are seen on the epicardial surface of the atrial wall 48. A hollow bore needle 50 can be placed in the middle of the purse string (i.e., at the identified entry location 26 for the left atrial portal) and into the left atrium 52. As shown in FIG. 9B, a wire with a flexible tip 54 may be passed through the distal end of the needle 50 and positioned inside the left atrium 52. As shown in FIG. 9C, the needle may then be pulled proximally out of the atrial wall 48 while leaving the wire in the atrium. In one embodiment, and as depicted in FIG. 9C, the guide wire inserted into the left atrium passes from outside the abdomen through the pericardial portal (not shown) and into the left atrium 52. FIG. 9D demonstrates the position of the left atrial portal 38 within the left atrium 52 over the guide wire 54. As shown in FIG. 9D, the left atrial portal 38 may be advanced over the guide wire 54 and positioned adjacent to the entry location. At this point, a removable dilating introducer 56 within the left atrial portal central lumen can be positioned over the wire 54 so as to engage the opening 28 in the left atrial wall 48. By pushing the left atrial portal distally, the dilating introducer may be inserted into the left atrial wall, thereby expanding the opening.

At this point, the left atrial portal may be secured in the left atrial wall. FIG. 9D demonstrates the use of a distal cap 58 to secure the left atrial portal 38 in the left atrial wall. The distal cap may be made of firm silastic or other surgically acceptable material. In certain embodiments, the cap may be coated with heparin. In certain embodiments, the distal cap may be formed with a central opening and an external diameter that is widens from proximal to distal. In this way the most distal part of the cap is wider than the proximal end of the cap. In an embodiment, the cap narrows at the portion of the cap that is located within the left atrial wall 48. The narrow neck helps secure the cap and the portal to the left atrial surface.

In certain embodiments, the cap may have elements on the proximal end of the cap to secure the cap in the atrial wall so as to prevent the left atrial portal from be inserted any further into the left atrium, so as to limit the amount of device which can be placed inside the left atrium. For example, in some embodiments, the cap may comprise at least two flat elements (e.g., wings) 59*a*, 59*b* that extend from the central diameter of the cap. The wings may be of the same material as the rest of the cap or may be made of a different material. The wings may be positioned at about the narrow neck of the cap. The wings may also provide additional security as the pledgets 30, 32 can be positioned external to the wings of the cap to secure the wings to the left atrial wall as the purse string is tightened. In an embodiment, and as shown in FIGS. 9A-9H, the wings may be inserted underneath the pledgets 30,32 such that tightening the sutures can be used to further secure the portal against the atrial wall.

FIGS. 9E-9H, shows an embodiment where the left atrial portal, dilating introducer, and needle are inserted as one unit. In FIG. 9E, the purse string has been positioned and the pledgets 30,32 are seen on the epicardial surface of the left atrium 48. The left atrial portal 38, dilating introducer 56, and needle 50 are positioned in the middle of the purse string on the left atrium 52. FIG. 9F shows the needle 50 advanced through the wall 48, and into the left atrium 52. FIG. 9G shows an embodiment where a wire with a flexible tip 54 has been passed through the needle 50, and is positioned inside the left atrium 52. The left atrial portal unit 38, dilating introducer 56, and needle 50 (which in some cases may be partially withdrawn) can then be advanced as one unit through the left atrial wall 48. FIG. 9H, shows the left atrial portal 38 threaded over the guide wire 54 and into within the left atrium 52, but with the needle withdrawn back into the left atrial portal and removed via by the operator by pulling the needle proximally out of the left atrial portal.

Figure 10B:
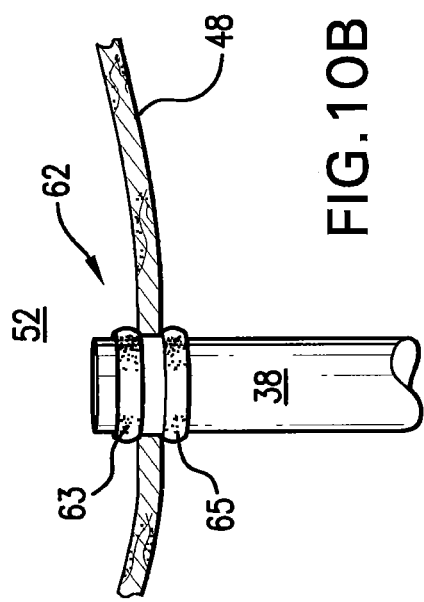
FIGS. 10A-10H illustrate other embodiments of a portal in accordance with alternate embodiments of the present invention, where
Figure 10D:
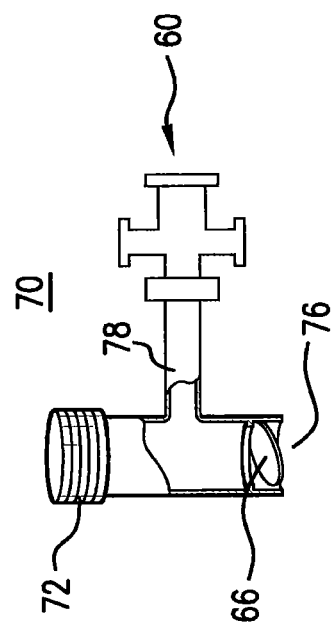
Figure 10A:
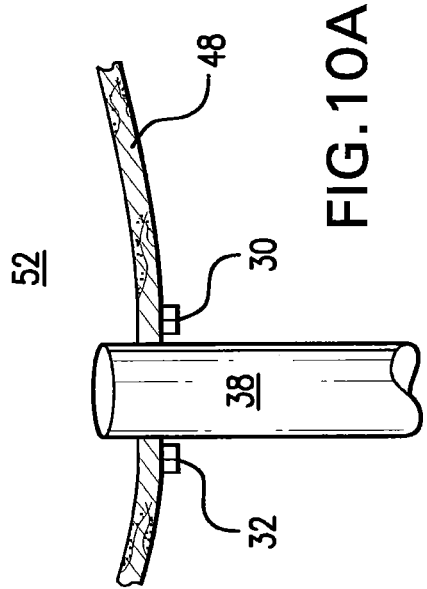

FIGS. 10A and 10B illustrate other embodiments of the left atrial portal. FIG. 10A illustrates the distal end of a left atrial portal without the atrial wall cap. As shown in FIG. 10A, this embodiment may be secured in the atrial wall 48 by tightening the purse string suture and pledgets 30, 32 once the distal open end is within the left atrium 52.

FIG. 10B is an embodiment of a left atrial portal that comprises an expandable cap 62 at the distal end of the left atrial portal. In an embodiment, the expandable cap may be used to secure the left atrial portal to the left atrial wall 48. In an embodiment, the expandable cap 62 has a distal portion 63 which, once inside the left atrium 52, can be expanded so as to increase the diameter of the cap and secure positioning of the cap so that the cap (and thus, the left atrial portal) cannot be pulled out of the atrium. The expandable cap 62 also has a more proximal portion 65 which is positioned external to the left atrium such that when this portion of the cap is expanded, the cap (and thus, the left atrial portal) cannot be further inserted into the atrium. In an embodiment, the cap may be heparin coated. The cap may be expanded with a gas (e.g., air) or a fluid (e.g., saline) that is injected through a lumen opening at the proximal end of the left atrial portal.

The proximal end of the left atrial portal may be fashioned to allow manipulation and access to various tools that are to be inserted into the left atrium. Also, the proximal end of the left atrial portal may be fashioned so as to facilitate insertion of the left atrial portal into the into the atrial wall by the physician, as e.g., to facilitate use of an ultrasound probe or other imaging equipment, or to facilitate use of needles, guide wires, the dilating introducer and/or the expandable distal cap as described herein.

Figure 10C:
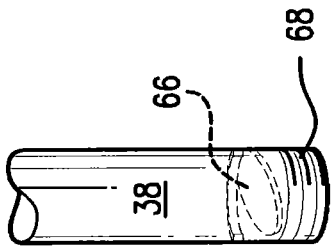

One embodiment of a proximal end of an atrial portal and/or a cardioscopic portal of the present invention is shown in FIG. 10C. There may be an addition to the proximal end to allow the passage of devices over the atrial portal, such as a larger portal to be inserted over the atrial portal 38. For example, a portal may be threaded over an atrial portal and used to place a suture in the atrial wall. In an embodiment, such an over-lying portal is a pericardial portal 2.

In certain embodiments, the proximal end of the atrial portal or a pericardial portal of the present invention may comprise a one way valve 66. Additionally or alternatively, the proximal end of the atrial portal or pericardial portal of the present invention may also have threads 68 for the attachment of extensions and adaptors 70. Such proximal adaptors and/or end pieces may have a cap 72 which can attach to threads 68 on the left atrial portal or the pericardial portal of the present invention. Also, in certain embodiments, such proximal adaptors may comprise one or more one-way valves 66. Where the proximal adaptor provides an extension to the portal, if may further comprise an open proximal end 76. Also, in certain embodiments, the proximal adpator/end piece may comprise an arm 78 for the attachment of a valve (e.g., a three-way valve or other valves) 60 for infusion of fluids.

Figure 10E:
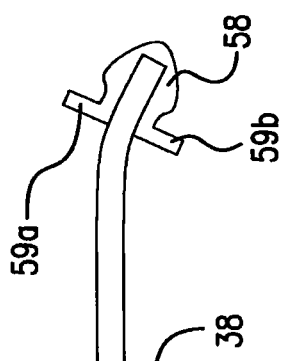

FIG. 10E, depicts an alternate embodiment of the proximal end of a left atrial portal or pericardial portal of the present invention. Thus, as illustrated in FIG. 10E, the left atrial portal 38 or a pericardial portal may, in certain embodiments, comprise a nonremovable port 72 having a one way valve 66 and a stopcock assembly 60. This configuration may be used to decrease the chance for air to enter into the left atrium as could occur with a detachable threaded proximal port (e.g., if port 72 were detachable). FIG. 10F shows an embodiment of a proximal port 72 in a head on view. The one-way valve opening 66 may be sized to accept the dilator introducer 56 used for introduction of the distal end of the left atrial portal into the left atrium.

Figure 10G:
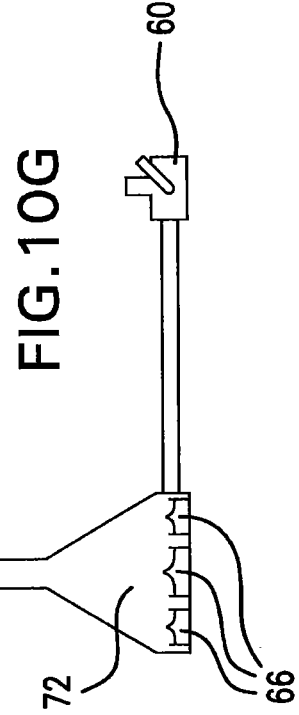
Figure 10H:
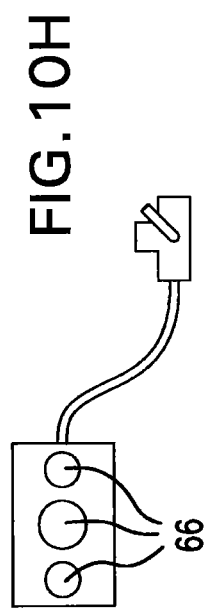
Figure 10F:
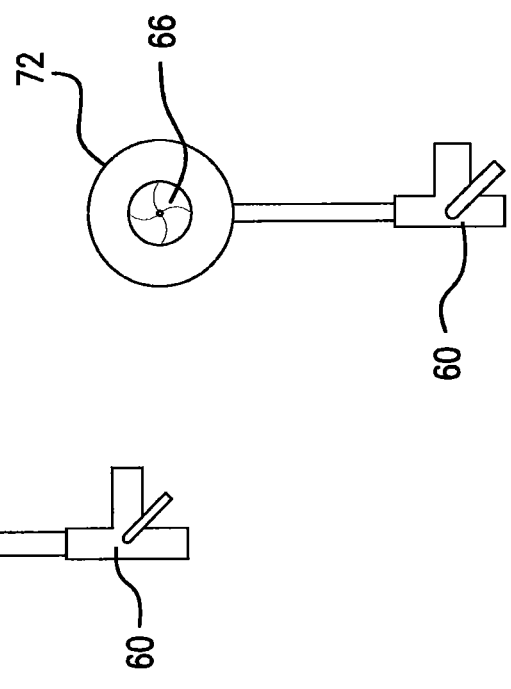

FIGS. 10G and 10H depict a proximal port 72 with a diameter that expands towards the proximal direction. As shown in FIG. 10G, the port may comprise multiple valves (e.g., one-way) that provide access to a left atrial portal or a pericardial portal of the present invention. The port shown in FIGS. 10G (top view) and 10H (head-on view) may comprise multiple one-way valves 66. Although the port is depicted as being triangular in shape, other shapes may be used. The left atrial portal 38 or pericardial portal can be sized as needed to allow more than one catheter or other instrument to be passed into the left atrium. An example is a mapping and ablation catheter.

Figure 11:
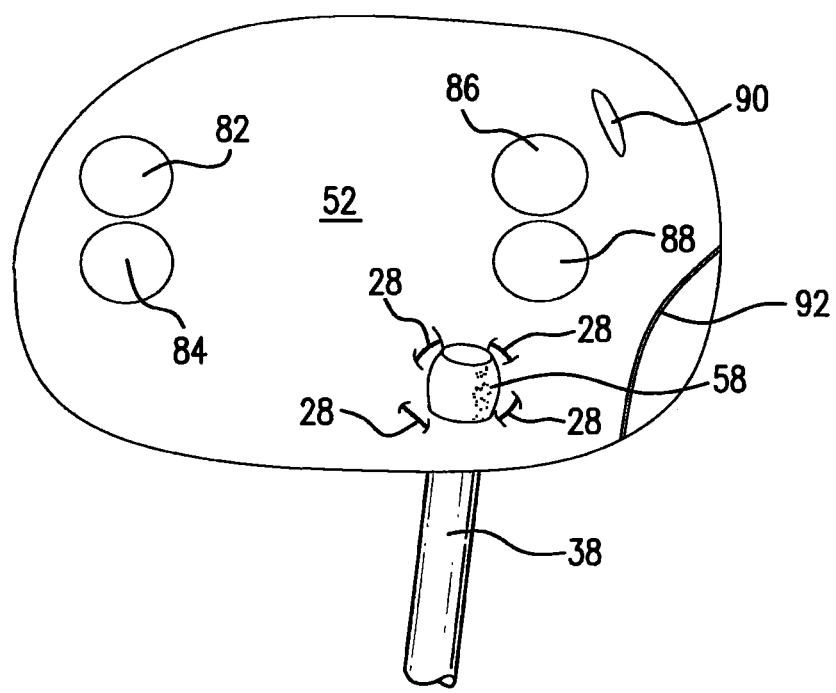
FIG. 11 illustrates the inside of the left atrium with the left atrial portal shown with the internal portion of the distal cap seen within the internal wall of the left atrium in accordance with an embodiment of the present invention.

FIG. 11 is a diagram of the inside of the left atrium 52 as accessed by a left atrial portal 38 of the present invention showing the right superior pulmonary vein orifice 82, the right inferior pulmonary vein orifice 84, the left superior pulmonary vein orifice 86, the left inferior pulmonary vein orifice 88, and the orifice to the left atrial appendage 90. The posterior annulus of the mitral valve 92 is also depicted. It can be seen that the distal end of the left atrial portal 38 enters the left atrium 52 such that the internal portion of the distal cap 58 is within the internal wall of the left atrium surrounded by the purse string suture 28.

Figure 12:
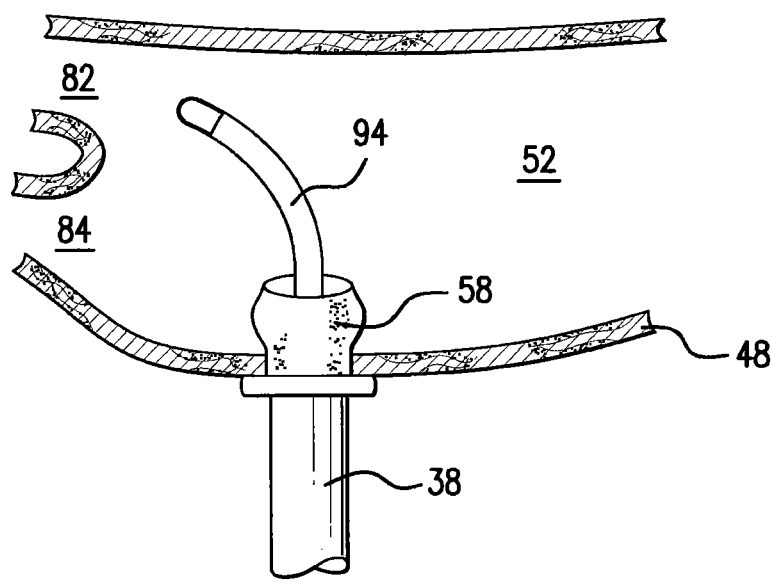
FIG. 12 illustrates the distal end of a left atrial portal having a distal cap positioned in the left atrial wall and having a catheter passing into the left atrium from outside the abdomen and through the central lumen of the left atrial portal in accordance with an embodiment of the present invention.

As described in detail herein, the devices, methods and systems of the present invention can provide for direct access to insert surgical tools and/or therapeutic devices in the left atrium. FIG. 12 illustrates a left atrial portal 38 and distal cap 58 positioned in the left atrial wall 48 such that the left atrial portal provides access to the left atrium 52. In an embodiment, and as illustrated in FIG. 12, the left atrial portal allows for a catheter (ablation, sensing electrode, angiography, or pressure-monitoring) 94 to be inserted directly into the left atrium 52 from outside the abdomen via the central lumen of the left atrial portal 38. The catheter may, for example, be an ablation catheter that can be directed into the right superior pulmonary vein orifice 82 or the right inferior pulmonary vein orifice 84 to treat arrhythmias originating in these locations. Other embodiments may include placing electrodes or pressure monitoring catheters at anatomical locations within the left atrium.

Figure 13:
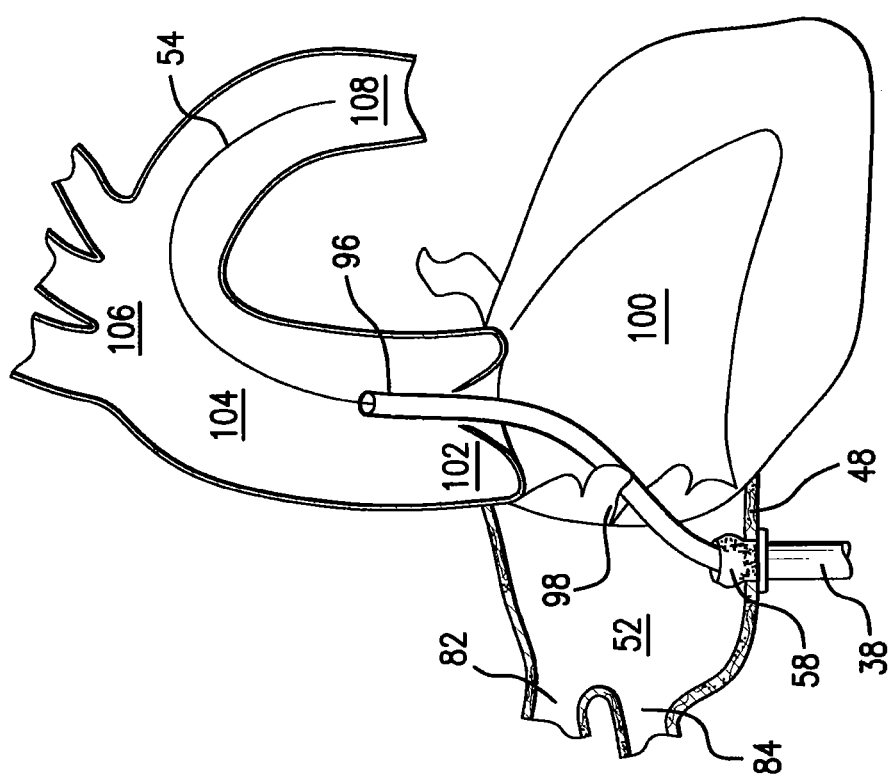
FIG. 13 illustrates a left atrial portal being positioned for repair of a valve in accordance with an embodiment of the present invention.

As described in detail herein, the devices, methods and systems of the present invention can provide for direct access for treatment of valves in the left atrium or parts of the heart that are accessible via the left atrium. FIG. 13 illustrates an embodiment of a method of using a left atrial portal of the present invention for repairing valves in the heart. Thus, as illustrated in FIG. 13, the left atrial portal 38 and distal cap 58 are positioned in the left atrial wall 48 so as to provide access, via the distal opening of the left atrial portal 38 to the inside of the left atrium 52. As shown in FIG. 13, a catheter with a hollow central lumen 96 may be threaded into the left atrium via the central lumen of the left atrial portal 38. The catheter may then be threaded by the physician manipulating the catheter at the proximal end of the left atrial portal to the valve requiring therapy. For example, in an embodiment, and as depicted in FIG. 13, the catheter may be threaded through the mitral valve 98, and through the left ventricle 100, out the aortic valve 102, and into the ascending aorta 104. Next, and as shown in FIG. 13, a guide wire having a flexible tip 54 may be passed through the catheter 96 into the ascending aorta, through the aortic arch 106 and down the descending thoracic aorta 108. The catheter 96 can then be removed leaving the wire 54 in place. This wire provides a platform for the positioning of devices (stents, valves) in the aortic valve 102 or the aorta 104,106, 108.

In an embodiment, echocardiography or ultrasound can be used to confirm positioning of the guide wire and other tools in the heart. Alternatively, in some embodiments, an endocardiograpic catheter positioned in the lumen of the left atrial portal or alternatively advanced into the left atrium may be used.

Figure 14:
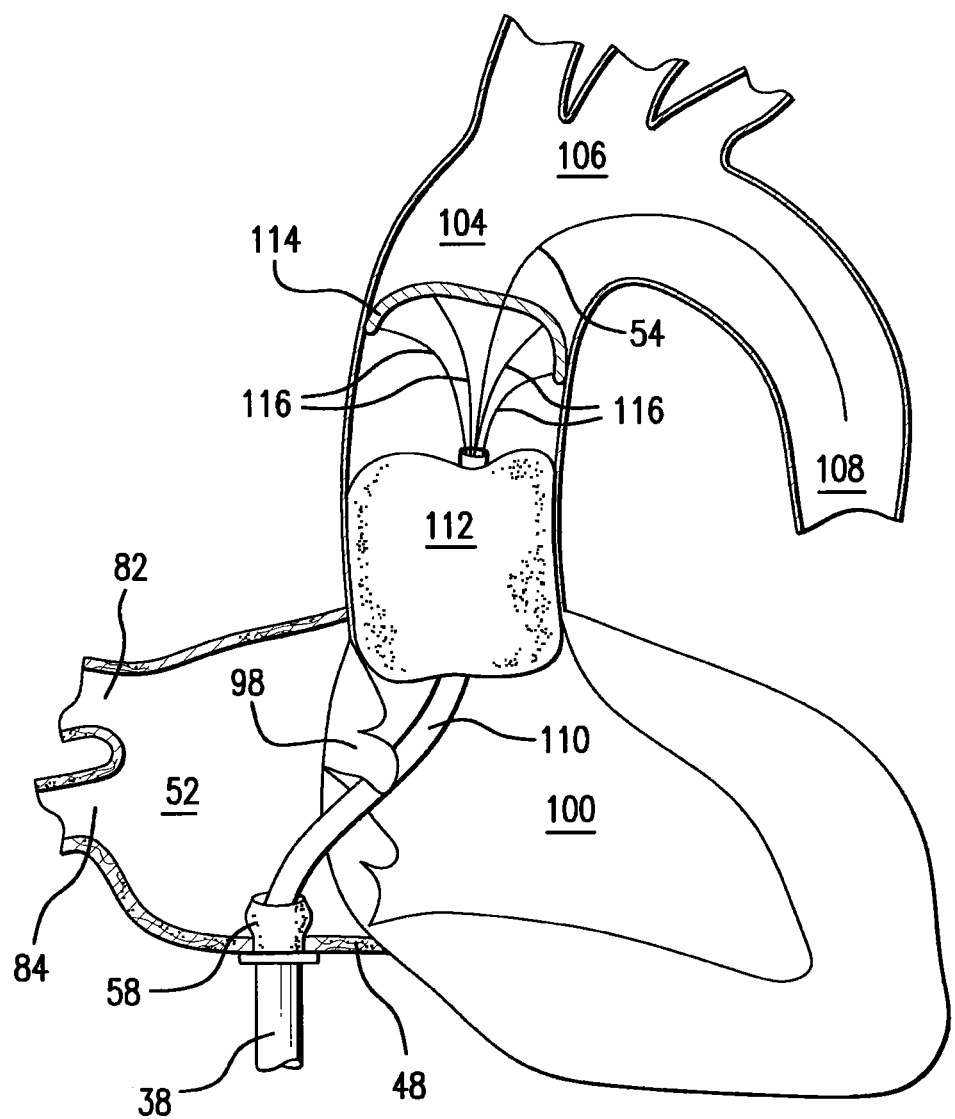
FIG. 14 illustrates a valve and balloon dilator catheter and associated dilating balloon being positioned and expanded at the location of the aortic valve using a guide wire as a platform for manipulation into position in accordance with an embodiment of the present invention.

In certain embodiments, and as illustrated in FIG. 14, the catheter 96 may be removed to allow for emplacing a dilator catheter 110 and associated dilating balloon 112 in the aorta using a left atrial portal of the present invention. Thus, as illustrated in FIG. 14, the catheter 96 (not shown) may be pulled back into the left atrial portal. At this point, a dilator catheter and balloon may be threaded along the guide wire 54 and positioned in the aortic valve. The balloon 112 may be expanded (e.g., with saline) to an appropriate pressure to compress the diseased aortic valve to the wall of the aorta, thus increasing the internal diameter of the aortic valve and making it more acceptable for stented valve deployment. In certain embodiments, and as depicted in FIG. 14, the device used for valve repair may include a debris capture device 114 to capture any debris which may be broken free from the vessel or the valve during the procedure. In an embodiment, the device for capturing such debris may be shaped like a parachute or umbrella. The debris capture device 114 may be positioned on the guide wire 54 downstream (i.e., in relation to blood flow) of the balloon 112 to capture loosened debris so as to decrease the risk of embolic event such as stroke. The capture device 114 may be included as part of the balloon dilator 110 or may be a separate, independent device. The deployment of the capture device may be performed by advancing the capture device 114 in an unexpanded configuration out the distal end of the catheter 110. Once released from the catheter 110, the capture device can be expanded (opened) by the intrinsic blood flow in the aorta. The capture device 114 may include attachment cords 116. Such attachment cords 116 can provide support, maintain the device in an expanded configuration despite variations in blood flow, and provide a mechanism for removal of the capture device at completion of the procedure. For example, once the procedure for repair of the valve is completed, the attachment cords 116 can be withdrawn, collapsing the capture device 114 around the debris, and then the collapsed capture device (and captured debris) can be withdrawn through the left atrial portal 38. Once the aortic valve is adequately dilated, the balloon is withdrawn leaving the guide wire 54 in position.

Figure 15:
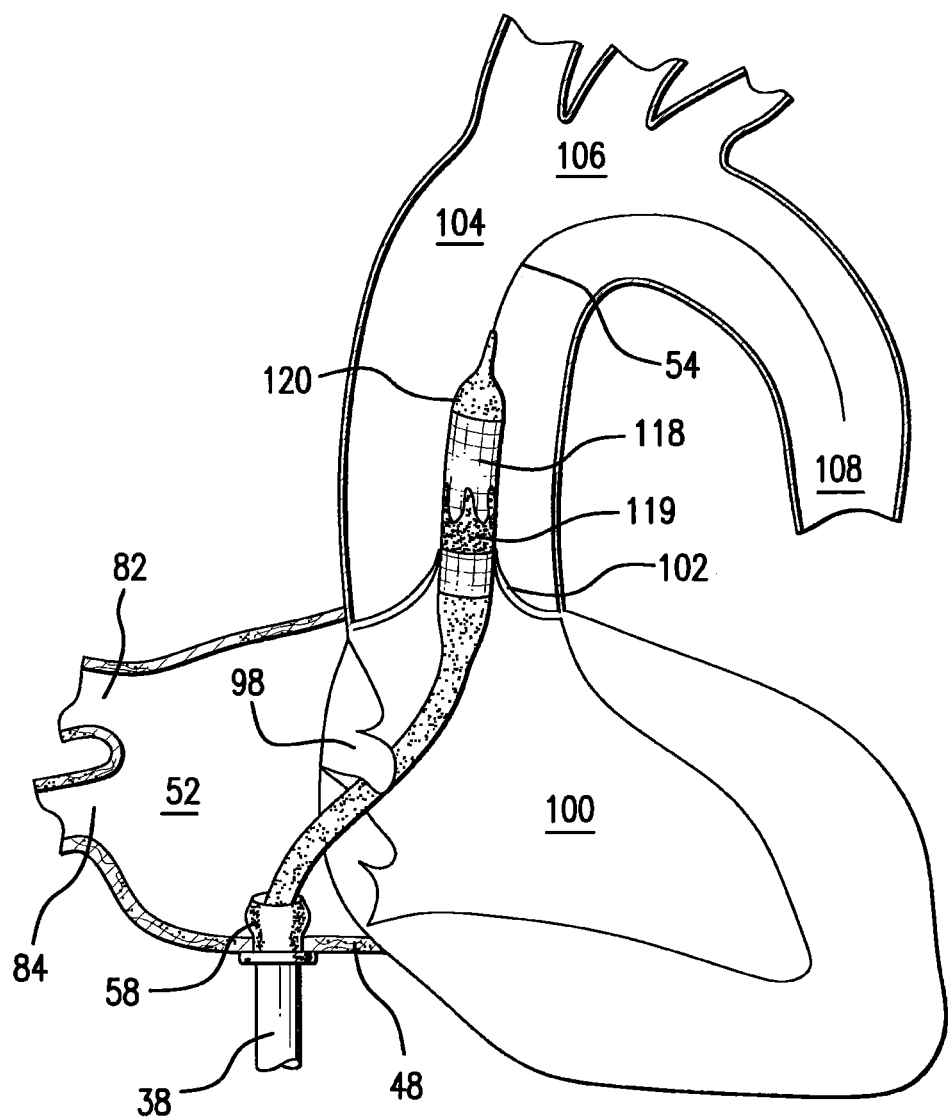
FIG. 15 illustrates an aortic valve stent prosthesis on a sheath with a tapered distal end in accordance with an embodiment of the present invention.

As described in detail herein, the devices, methods and systems of the present invention can provide for direct access for emplacement of stented valves in the left atrium or parts of the heart that are accessible via the left atrium. FIG. 15 demonstrates the stented aortic valve prosthesis 118, 119 on a sheath 120 with a tapered distal end that has been advanced and over the guide wire 54 and positioned in the aorta 104. In an embodiment, the sheath may have an expandable portion on which the stent 118 and valve prosthesis 119 is mounted. When expanded, the sheath can secure the prosthesis into the appropriate position at the aortic valve 102. Once the stent 118 and prosthesis 119 are deployed such that it is securely positioned within the wall of the aorta, the introducer 120 can be removed leaving the guide wire 54 in position.

Figure 16:
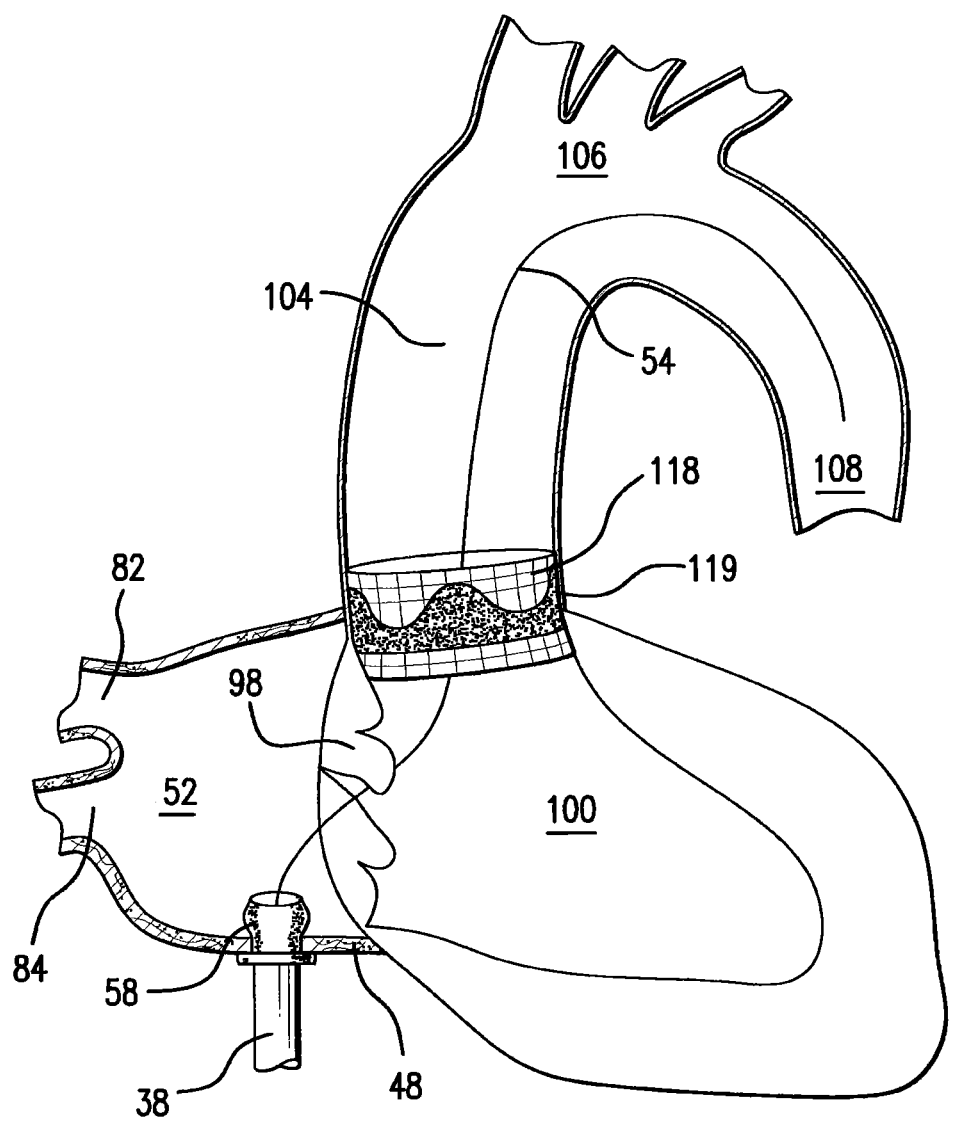
FIG. 16 illustrates an aortic valve stent prosthesis emplaced in the aortic valve after delivery with a left atrial portal in accordance with an embodiment of the present invention.

FIG. 16 demonstrates an aortic stented valve prosthesis 118, 119 in appropriate positioned at the location of the aortic valve. At this point, the guide wire 54 and the left atrial portal 38 may be removed and the purse string suture (not shown) can be tightened to close the opening in the left atrial wall 48.

Figure 17:
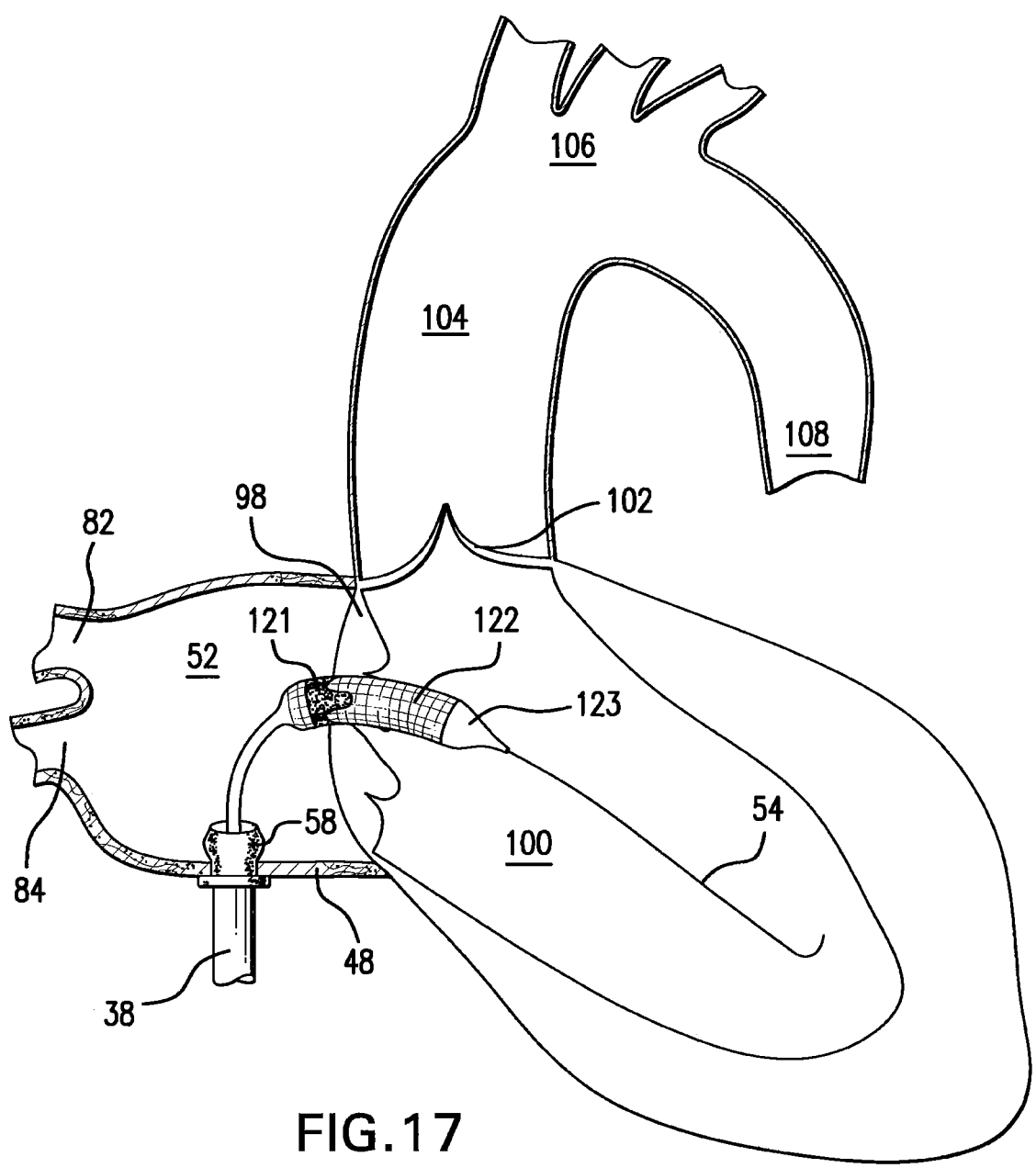
FIG. 17 illustrates a mitral valve stent prosthesis emplaced in the mitral valve in accordance with an embodiment of the present invention.

The devices, methods and systems of the present invention may be used to treat other valves that are accessible via the left atrium. FIG. 17 depicts emplacement of a stented mitral valve prosthesis at the mitral valve 98 using the devices, methods and systems of the present invention. The stented mitral valve prosthesis 121, 122 may be deployed in the similar manner as described for the aortic valve, as for example using an expandable introducer 123 to deploy the stent 122 and prosthesis 121 into the appropriate position in the valve 98. Again, the guide wire 54 may be used as a platform to position the introducer 123 and the stent and prosthesis 121, 122. In this embodiment, the guide wire is threaded into the left ventricle 100. Echocardiography can be used to confirm position of the aortic and the mitral valve prosthesis and to confirm appropriate location and function after deployment.

As described in detail herein, the devices, methods and systems of the present invention can provide for direct access for reduction of the posterior annulus of the mitral valve for patients with mitral regurgitation. To enable reduction of the posterior annulus of the mitral valve, suture material can be positioned into the posterior annulus to provide an anchor for tissue approximation. FIG. 18A demonstrates one embodiment of one such suture anchor device. FIG. 18A is an example of a "twosided" barbed needle 124 with attached suture 126. The barbed suture can be deployed into the annulus of the posterior mitral valve to secure the suture in the annulus of the posterior mitral valve for annular approximation. When the barbed needle is inserted, counter-traction (i.e, by pulling distally) can be used to engage the barbs in the mitral valve annulus tissue such that the barbed needle is securely positioned in the annulus of the posterior mitral valve. Such barbed needles can be inserted easily using the devices, methods and systems of the present invention and, by securing two or more sutures, can provide sufficient capture of the mitral valve annulus to allow reduction of the posterior mitral valve annulus.

Figure 18C:
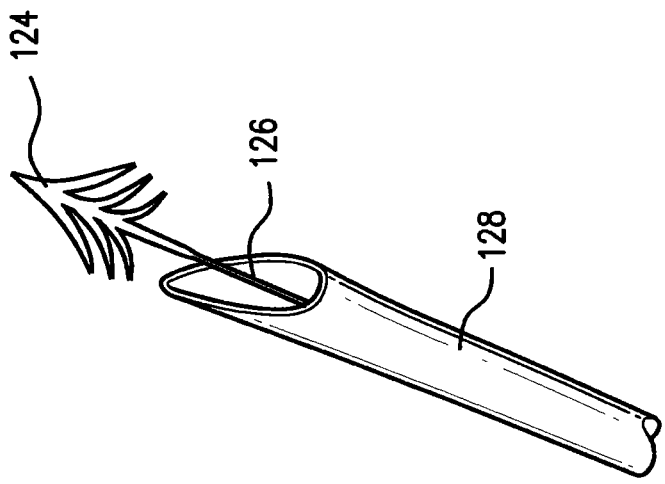
FIGS. 18A-18C illustrate a barbed needle as unsheathed (FIG. 18A), or being delivered using an introducer needle (FIG. 18B) and emerging from the introducer needle (FIG. 18C) in accordance with an embodiment of the present invention.
Figure 18B:
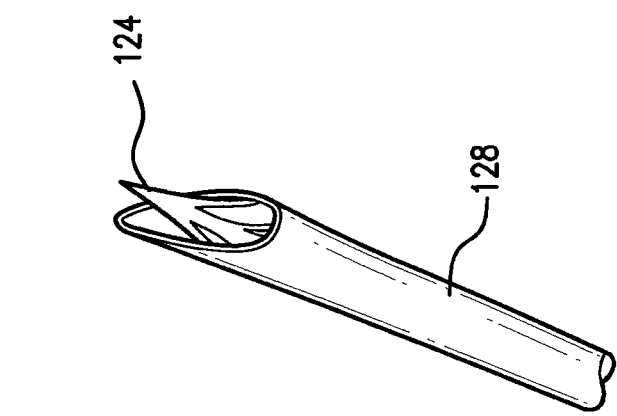
Figure 18A:
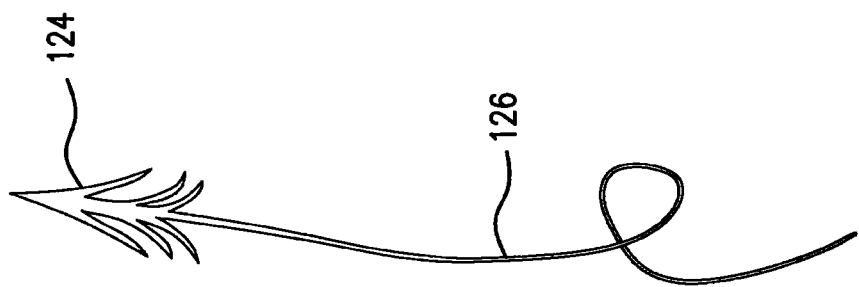

FIGS. 18B and 18C shows a barbed needle 124 and associated introducer needle 128 that may be used to insert the needle in the proper location. The barbed needle 124, when within the introducer needle 128 does not have the barbs exposed (FIG. 18B). When the barbed needle 124 is advanced, as in FIG. 18C, the barbs are exposed and can be securely inserted into (i.e., capture) adjacent tissue, preventing removal and retraction.

In certain embodiments, the barbed needle also comprises a sheath, positioned over the suture, and that abuts the base (i.e., proximal end) of the needle. Such a sheath may be used to push the needle out the distal end of the introducer needle. FIGS. 19A and 19B, demonstrates how the barbed needle 124 is advanced out the end of the introducer needle 128 using a sheath 130 that is threaded over the suture 126. As the sheath 130 is advanced, it is able to push against the base of the barbed needle 124. The sheath 130 has a central lumen which is large enough to cover the suture 126, but which is not larger than the barbed needle 124. This allows the physician manipulating the proximal end of the sheath to introduce the barbed needle into the tissue as the sheath is advanced distally through the introducer needle.

Figure 20:
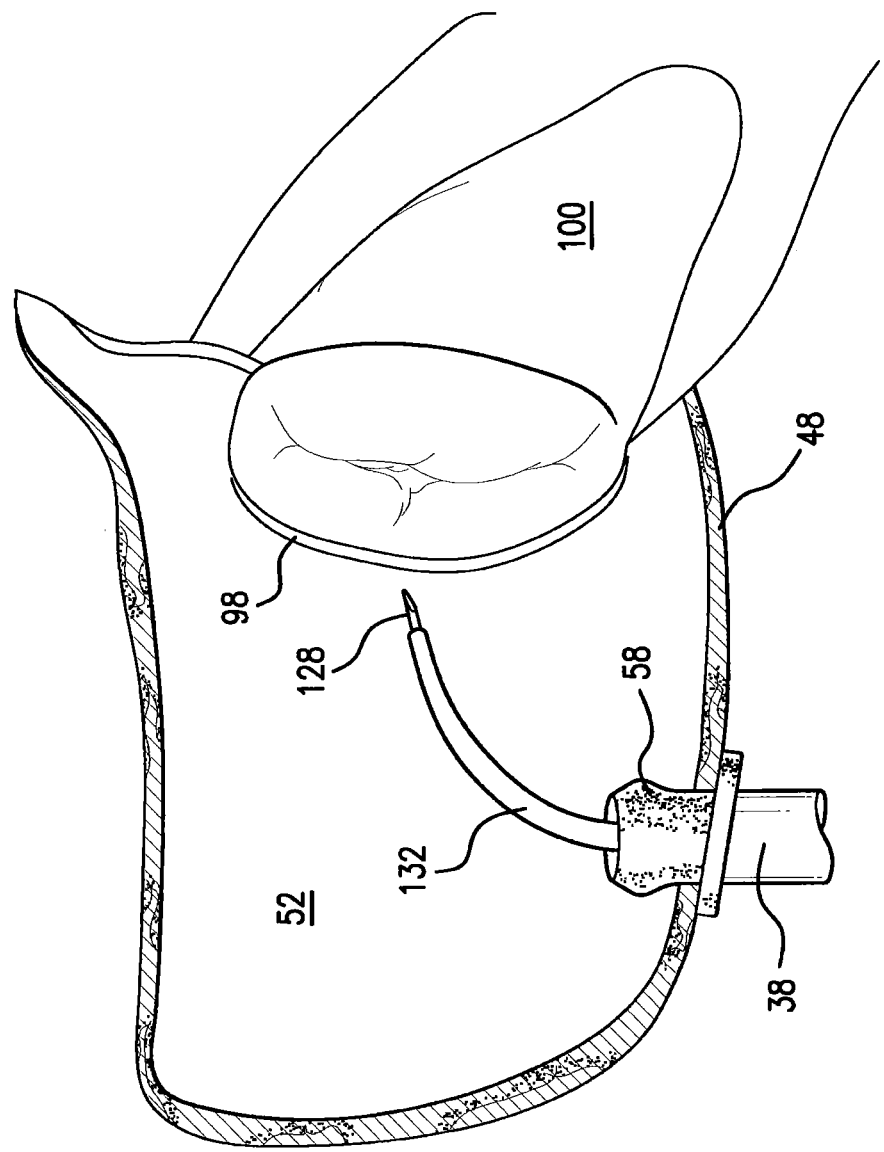
FIG. 20 illustrates an introducer needle being used to deliver a barbed needle to the posterior mitral valve annulus in accordance with an embodiment of the present invention.

FIG. 20 demonstrates one example of the use of the devices, methods and systems of the present invention for positioning an introducer needle 128 (and associated barbed needle, not shown) into the posterior mitral valve annulus 98. As shown in FIG. 20, the introducer needle 128 may be contained within the central lumen of a steerable catheter or sheath 132. The steerable sheath 132 may be passed through the left atrial portal 38 into the left atrium 52 and towards the mitral valve 98. Once the distal end of the steerable sheath is positioned close to the mitral valve, the introducer needle 128 can be advanced out the distal end of the steerable sheath 132.

Figure 21:
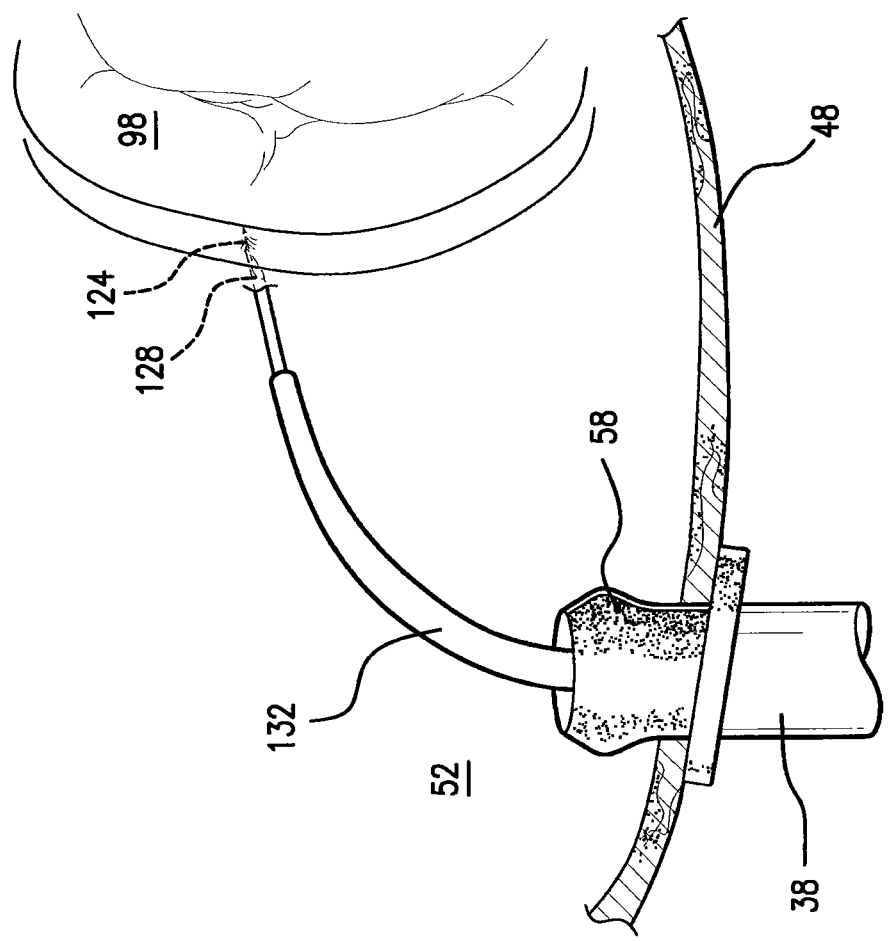
FIG. 21 illustrates the positioning of a barbed needle in the posterior annulus tissue of the mitral valve in accordance with an embodiment of the present invention.

FIG. 21 depicts placement of the introducer needle 128 in the posterior annulus tissue of the mitral valve 98. As shown in FIG. 21, the steerable sheath 132 can be manipulated so as to emerge from the left atrial portal 38, and is threaded through the left atrium 52, and to the mitral valve where the introducer needle 128 is inserted into the annulus of the mitral valve using echocardiographic guidance. Once the introducer needle 128 is in position, the barbed needle 124 may be advanced into the annular tissue where it is secured.

Figure 22:
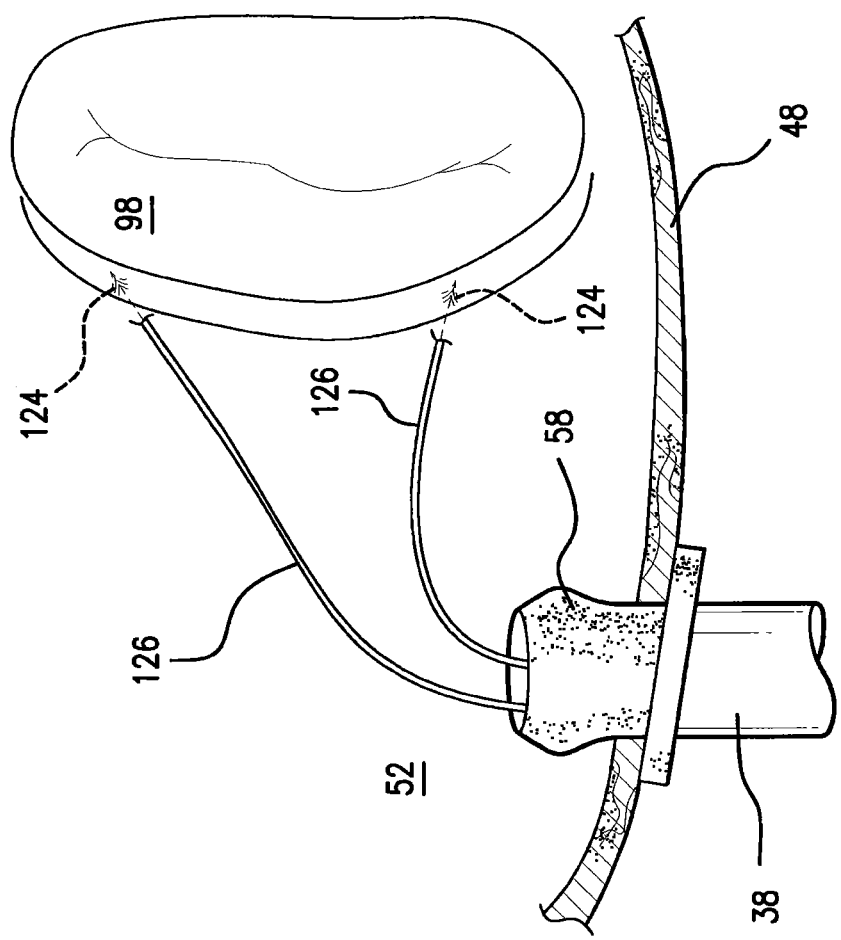
FIG. 22 illustrates two barbed needles positioned in the posterior annular tissue of the mitral valve in accordance with an embodiment of the present invention.

Reduction of the posterior mitral valve annulus may generally employ two or more such barbed needles that are implanted in the posterior mitral valve annulus. FIG. 22 demonstrates two barbed needles 124 in the posterior annular tissue of the mitral valve 98. The needles are generally positioned at a distance from each other which may range from about 1 to 5 cm, depending upon the extent of reduction required. As illustrated in FIG. 22, the suture 126 of each barbed needle 124 may exit the left atrium 52 via the left atrial portal 38. The location of the barbed needles 124 in the annulus is selected to cause the posterior annulus to be reduced when the sutures are tightened and the needles are brought into approximation. As the needles are approximated, the annulus will be plicated, or reduced. Using the devices, methods and systems of the present invention, reduction of the mitral valve annulus may be evaluated, in real-time (i.e., on the beating heart), by echocardiography to determine reduction in mitral valve regurgitation as the sutures are tightened.

Figure 23:
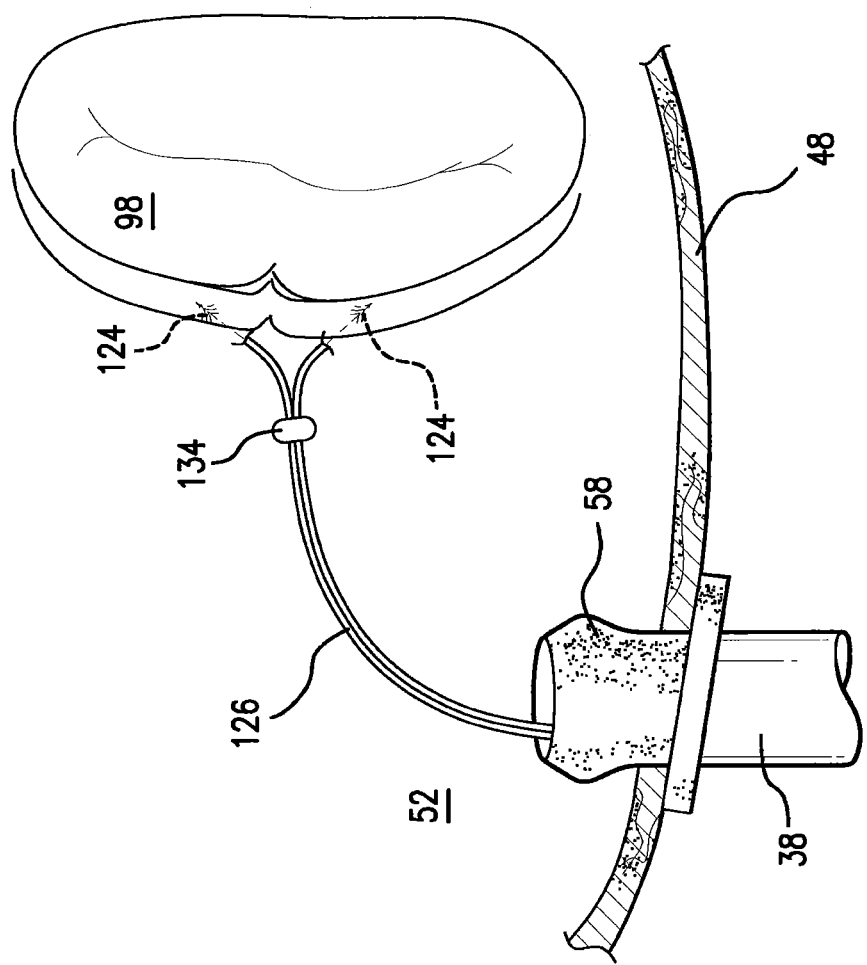
FIG. 23 illustrates the reduction of the annulus as the barbed needles positioned in the posterior annular tissue of the mitral valve are drawn closer to each other in accordance with an embodiment of the present invention.

FIG. 23 depicts the reduction of the annulus as two barbed needles 124 are drawn closer to each other. A clasp 134 may be advanced over the suture to the point that the clasp approximates the barbed needles and holds them in the correct position. In an embodiment, advancement of the clasp 134 over the suture 126 may be done using a clasp advancing catheter (not shown) with an open central lumen that can be threaded over the suture (i.e., one suture per barbed needle) to push the clasp distally. The clasp may be advanced as the mitral valve regurgitation is interrogated. Once the appropriate reduction of the annulus is achieved and the mitral regurgitation is eliminated, the clasp advancing catheter may be removed, leaving the clasp 134 remaining in position with the appropriate tension on the sutures 126.

Figure 24:
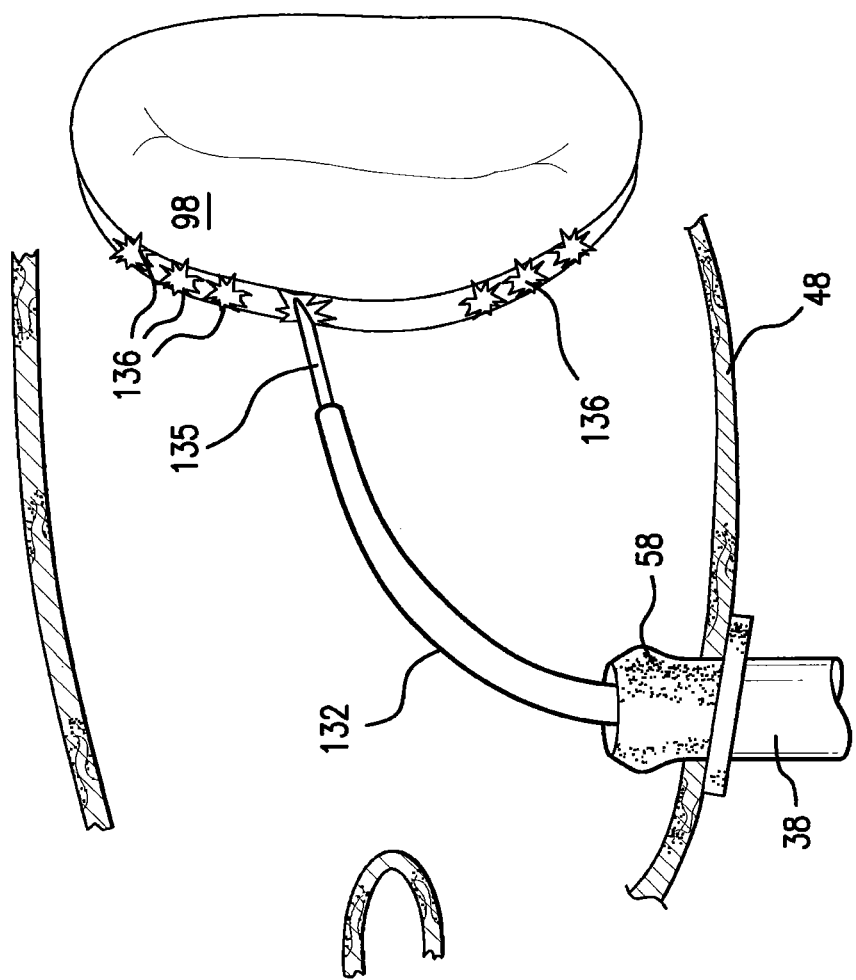
FIG. 24 illustrates posterior mitral valve reduction using ablation in accordance with an embodiment of the present invention.

FIG. 24 depicts another embodiment of posterior mitral valve reduction. Using a steerable sheath 132 positioned through the left atrial portal 38, a radiofrequency needle 135 may be positioned at selected locations in the mitral valve annulus. Ablation of the tissue 136 to create a scar can then lead to contraction of the tissue around the mitral valve. When a series of ablations 136 within the posterior mitral valve annulus are created, the contraction which occurs can reduce the annulus and thereby reduce mitral regurgitation. The radiofrequency needle 135 generates thermal heat within the cardiac tissue.

Figure 25:
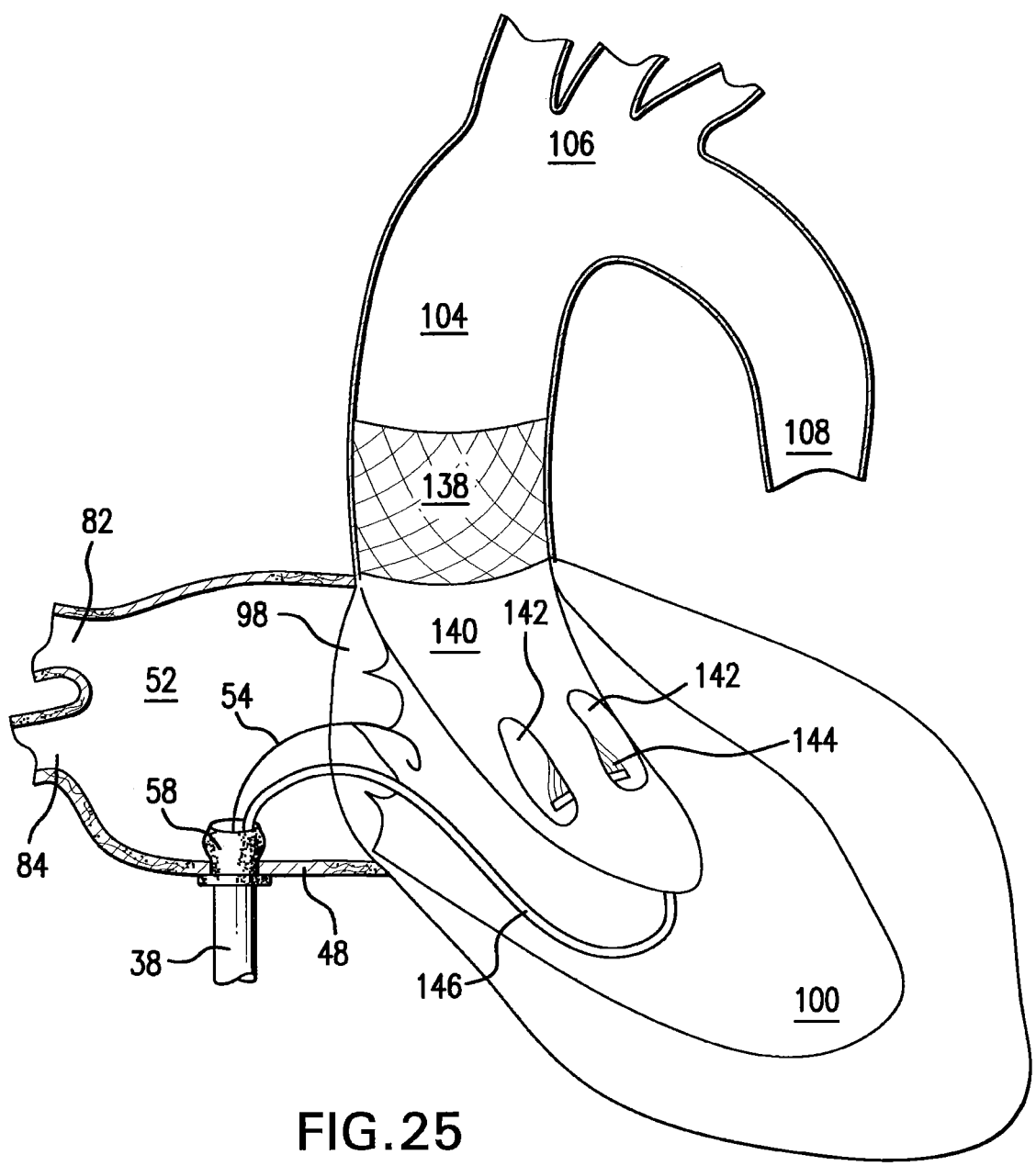
FIG. 25 illustrates emplacement of an intracardiac assist device for a bridge to transplantation in accordance with an embodiment of the present invention.

As described in detail herein, the devices, methods and systems of the present invention can provide for direct access to the heart to allow for implantation of intracardiac assist devices (ICADs). FIG. 25 demonstrates an embodiment of an intracardiac assist device 140 for a bridge to transplantation. When positioned in the left ventricle, the ICAD is used to encourage blood flow from the left ventricle 100 out the aorta 104. As depicted in FIG. 25, the ICAD 140 may be secured, in some embodiments, by a stent positioned at the ejection end 138 of the ICAD. The stent 138 may be part of the ICAD 140 or, in alternate embodiments, may be a separate device. The ICAD generally is configured with inflow openings 142, where blood may be drawn into the ICAD. The blood may then be ejected with a pump 144 contained within the ICAD 140. In alternate embodiments, the internal ICAD pump may be a centrifugal head pump, a diaphragm pump, or an impellar type pump.

Similar to implantation of other devices, and as depicted in FIG. 25, the ICAD may be inserted over a guide wire 54 (partially withdrawn) which is positioned using a left atrial portal 38. Thus, as shown in FIG. 25, the guide wire may be threaded through the left atrium 52, the mitral valve 98, the left ventricle 100, and out the aorta 104. With the guide wire 54 in place, the ICAD device may then be inserted and, once in appropriate position, the distal stent portion deployed to secure the device. As known by those in the art, other embodiments may include other mechanisms to secure the ICAD to the endocardial surface and prevent migration.

Once the ICAD is secured in place, energy may supplied by a cable 146 which exits through the mitral valve 98 and left atrium 52 to a power source (e.g., generator) placed subcutaneously in the abdominal wall. In a similar manner, temporary assist devices which currently exist on the market, i.e. NOVACOR® (World Heart, Salt Lake City, Utah) or HEARTMATE® (Thoratec, Pleasanton, Calif.), may be inserted. A venous drainage cannula can be inserted through the left atrium 52 and into the left ventricle 100 via a left atrial incision similar to the one for the left atrial portal. This cannula can be connected to the temporary assist device in the abdominal wall on the inferior side of the diaphragm. The arterial inflow limb (i.e., the part of the pump used to return the blood to the aorta from the left atrium or left ventricle) can be a woven graft tunneled to the subclavian artery on the left or right or to the abdominal aorta. In a similar manner, an IMPELLA® device (Abiomed, Danvers, Mass.) can be inserted via the left atrial portal into a position in the left ventricle so that the ejected blood passes into the aorta.

Figure 26A:
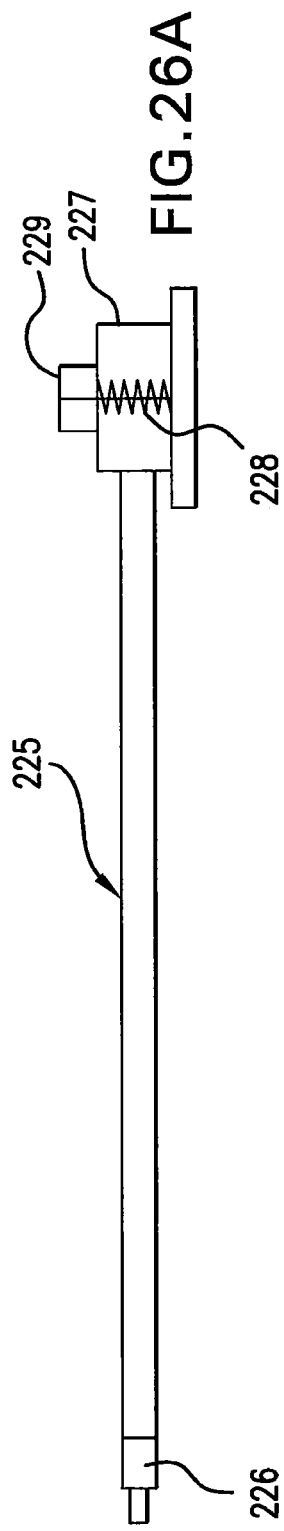
FIGS. 26A-26C illustrate a pacing lead for use with an atrial portal in accordance with an embodiment of the present invention, where
Figure 26B:
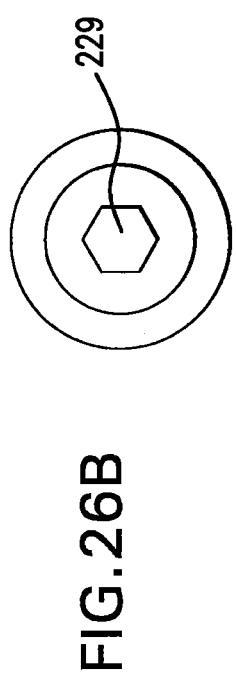
Figure 26C:
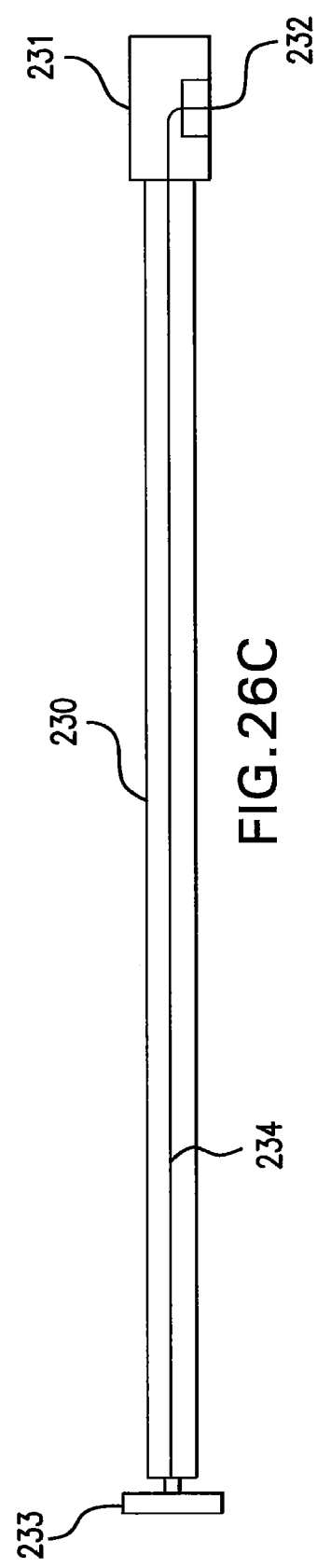

As described in detail herein, the devices, methods and systems of the present invention can provide for direct access to the heart to allow for implantation of electrical leads for pacing the heart. FIGS. 26A-26C, depict an embodiment of a cardioscopic pacing lead that may be implanted within the heart or on the outer surface of the heart using an atrial portal, or a pericardioscopic portal of the present invention. Thus, as shown in FIG. 26A, the cardioscopic pacing lead 225 may have a proximal end having the bipolar or unipolar lead attachment 226. In certain embodiments, and as depicted in FIG. 26A, the distal end may have an active fixation mechanism 227. The fixation mechanism may, in certain embodiments include an extendable/retractable screw 228 and an external head 229. The shape of the head may be varied as required; FIG. 26B depict a head that is of a hexagon shape (head-on view) but other shapes may be used. For example, in alternate embodiments, the head may be rectangular, square, or another polygonal shape to facilitate use of a socket type wrench being used to rotate the head and screw the coil into the epicardial tissue.

FIG. 26C shows an embodiment of a fixation unit 230 for the lead (not shown in unit). The distal end 231 of the fixation unit may have a recessed cavity 232 for insertion of the head (e.g., shown as hexagon shape) which fits over the active fixation mechanism 227 and onto the external head 229. In certain embodiments, the extendable/retractable screw 228 (FIG. 26A) can be either advanced or withdrawn by use of a handle 233 which may be attached by a cable mechanism or gear mechanism 234 to the distal end 231 of the fixation unit, and which may have the ability to rotate. This can allow for either extension or retraction of the extendable/retractable screw 228.

Figure 27A:
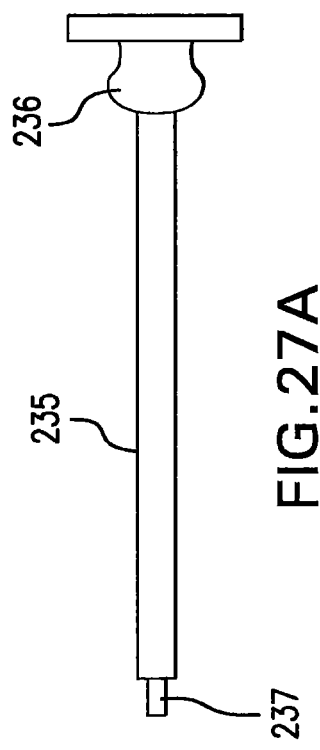
FIGS. 27A-27C illustrate an atrial pressure sensor and deployment of such a sensor in the left atrium in accordance with an embodiment of the present invention, where
Figure 27C:
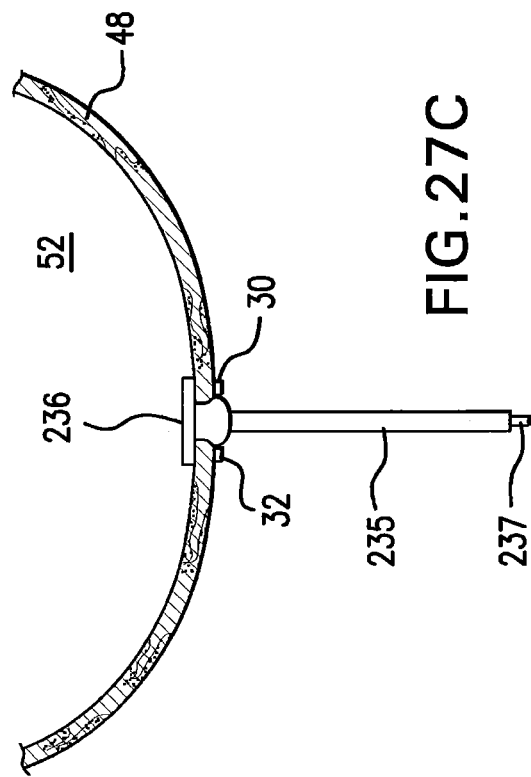
Figure 27B:
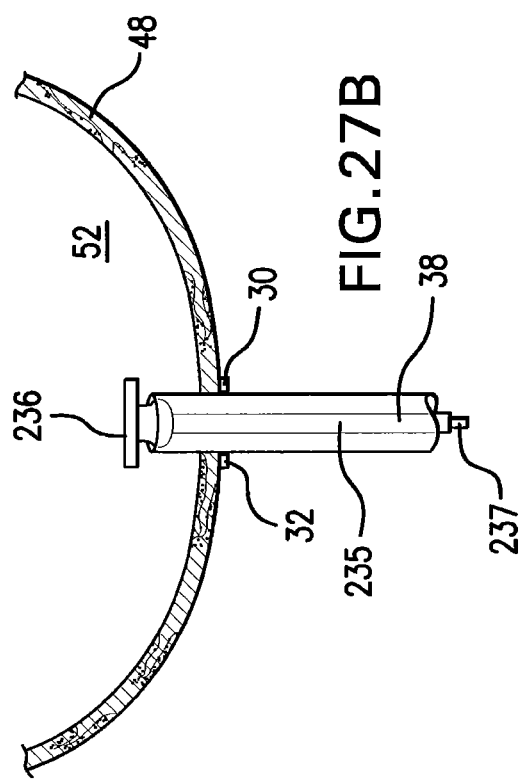

As described in detail herein, the devices, methods and systems of the present invention can provide for direct access to the heart to allow for implantation of left atrial pressure sensors. FIGS. 27A-27C, depict an embodiment of a left atrial pressure sensor, and deployment of such a sensor in the left atrium in accordance with an embodiment of the present invention. FIG. 27A shows the left atrial pressure sensor 235 having a proximal end 237 and a distal end 236, and which may be emplaced using a left atrial portal of the present invention. The distal end 236 may be made of silicone or similar material, and be sized to have a circumference that is larger the inside diameter of the left atrial portal 38, but which is flexible enough to be inserted through the distal opening of the left atrial portal 38 and deployed into the left atrium 52 (FIG. 27B). The depiction in FIG. 27B shows the left atrial portal 38 deployed in the atrial wall and having the pressure sensor 235 contained within the lumen of the left atrial portal and emerging from the distal end of the left atrial portal into the atrium 52. At this point, the distal end 236 of the pressure sensor 235 may then be pulled proximally against the left atrial wall 48. Once the pressure sensor has been positioned to abut the left atrial wall 48, the left atrial portal 38 can be removed (i.e., pulled out of the patient), and the suture (not shown) and pledgets 30,32 tightened to secure the pressure sensor in position. FIG. 27C shows a left atrial pressure sensor 235 in the final deployed position.

As noted in the various embodiments described herein, in certain embodiments, the devices, methods and systems of the present invention provide access to the pericardial space. FIGS. 8A-AD depict an embodiment of a portion of a pericardial portal of the present invention. FIGS. 28A-28C, depict an alternate embodiment of a pericardial portal 2 of the present invention. Thus, as shown in FIGS. 28A-28C, in some embodiments, the distal end 239 of the pericardial portal 2 may be tapered to prevent trauma to the cardiac structures and to allow the distal end to be flush against the myocardium. In certain embodiments, the pericardial portal may include a tube to provide suction 240. Also in certain embodiments, the pericardial portal may include an infusion port 241 incorporated into the wall of the pericardial portal, and which allows for suctioning of the pericardial space and infusion of fluid or contrast. Near the distal end of the pericardial portal there may be access ports 242 on either side of the portal to allow the passage of instruments, catheters, or scopes out of the portal. These access ports 242 may be outlined with radiographic markers 243 to allow visualization under fluoroscopy. The proximal end may, in certain embodiments, have a securing mechanism 244 to prevent slippage.

Figure 29:
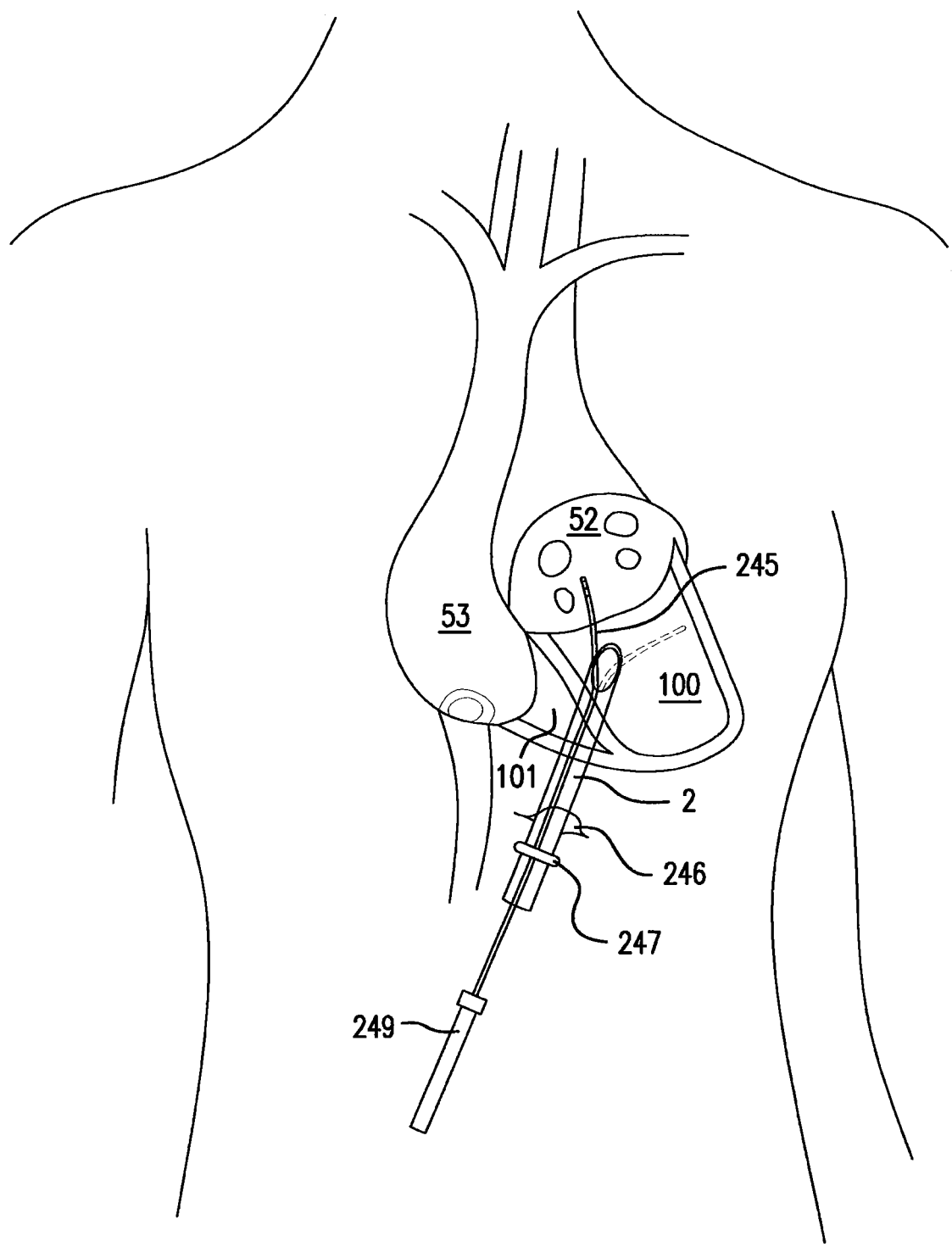
FIG. 29 shows a pericardial portal with ablation catheters on the epicardial surface of the left atrium and left ventricle in accordance with an embodiment of the present invention.

FIG. 29 shows the pericardial portal 2 with ablation catheters 245 on the epicardial surface of the left atrium 52 and left ventricle 100. Shown is the right atrium 53, right ventricle 101, the pericardial cannula 2 inserted via an incision 246 into the pericardial space. The distal end of the catheter 249 may be manipulated by the physician.

Methods of Making Left Atrial Portals

In other embodiments, the present invention may comprise methods of making the devices either singly, or in combination with other therapeutic devices as kits or systems. For example, in certain embodiments, the method may comprise manufacturing an atrial portal, and/or a pericardioscopic portal of the present invention. Also, the method may comprise manufacturing inner cannulas, catheters and/or sheaths comprising a tool or tools used for the procedures described herein.

The body of the left atrial portal and/or the pericardioscopic portal may be made of a rigid material so as to provide support for manipulation of the distal end of the portal at the body site of interest. For example, the atrial portal and/or the pericardioscopic portal may be fashioned from a plastic that while soft enough to prevent trauma to any tissues or organs encountered by the portal, will allow for certain organs (e.g., the heart) to be lifted from their normal positions and manipulated as required. For example, metals such as stainless steel, spring steel, nickel titanium alloys, other alloys, or aluminum may be used. Or, the portal(s) may be made of plastic. For example, a resilient plastic such as vinyl, nylon, polypropylene, polyethylene, ionomer, polyurethane, or polyethylene tetraphthalate (PET) may be used. Again, one of ordinary skill in the art having the benefit of this disclosure would appreciate that other materials, including those that are well-known to one in the art, may be applied to configure the portals described herein.

Also, in certain embodiments, the atrial portal and/or the pericardial portal may comprise reinforcing elements. The reinforcing elements can allow the portal to bend as it is maneuvered around and to body sites of interest without allowing the portal to collapse. Such reinforcing elements may comprise strands of metal or sturdy plastic that can be molded into the portal body using methods known in the art.

The distal end of the atrial portal and/or the pericardial portal may be substantially planar. Or, the distal end may be formed so as to have a curvilinear shape. Generally, the atrial portal may comprise a distal end that is substantially flush with the cross-sectional diameter of the portal so that the distal end of the atrial portal is substantially square (i.e., perpendicular) to the long axis of the atrial portal as viewed from the side (e.g., as shown in FIG. 10A for the atrial portal and FIG. 2 for the pericardial portal). In an embodiment, the pericardial portal may have a curvilinear distal portion such that the distal opening is not parallel to the proximal opening, but includes tapering along at least a part of the circumference (e.g., as shown in FIG. 28). Also, in certain embodiments, the pericardial portal may comprise a curvilinear or hood-shaped formation at the distal end, which can provided an arched shape to the distal end of the pericardial portal. In this way, the pericardial portal may facilitate access to the heart where a straight cannula would not be able to abut the surface of the heart. Or, the pericardial portal may comprise a substantially straight cylindrical shape.

Also, in certain embodiments, the atrial portal and/or the pericardial portal may be designed to have one or more narrowed openings at certain parts of the distal opening to facilitate positioning of tools in the distal opening. Also, the distal end of the atrial portal and/or the pericardial portal may have an expanded opening, such that the circumference of the distal opening is greater than the circumference of the proximal opening of the portal.

The distal end of the atrial portal and/or the pericardial portal may be made of a rigid material so as to provide support for manipulation of the distal end at the body site of interest. For example, the distal end of the atrial portal and/or the pericardial portal may be fashioned from a plastic that while soft enough to prevent trauma to any tissues or organs encountered by the cannula, will allow for certain organs (e.g., the heart) to be lifted from their normal positions and manipulated as required. For example, in certain embodiments, Silastic or plastic with wire or Nitinol reinforcement may be used. Or, the distal end of the atrial portal and/or the pericardial portal may comprise a hard plastic (e.g., polypropylene, polyethylene) and have a rubber or foam cushion material on its distal end.

The atrial portal and/or pericardial portal may comprise a distal end having a malleable material that is suitable to contact the tissue. For example, the pericardial portal may comprise a soft lip, made of rubber or foam at its distal end.

As described herein, in certain embodiments, the atrial portal has a cap at the distal end. The cap may be made of materials such as a soft plastic, foam, rubber, polyurethane foam, or polystyrene foam. In certain embodiments, at least part of the cap may be expandable and/or inflatable so as to have an portion that can be expanded outwards of the central longitudinal axis of the portal.

Also, many of the tools used with either the pericardial portal and/or the atrial portal may comprise an inflatable member. For example, an inflatable member may be positioned on the distal end of the portal and may be inflated to provide an extended diameter when the portal is threaded between various organs or tissue sites. Or, an internal catheter having an inflatable member may be used to expand a vessel prior to implantation of a stent and/or valve prosthesis. The balloon may be made of an expandable plastic or cloth such as silastic or soft plastic or thin Gortex.

In an embodiment, the atrial portal and/or pericardial portal are cylindrical in shape. Or, the cross-sectional shape of the portals may be other shapes, such as oval, rectangular, polygonal (e.g., hexagonal, octagonal) and the like.

The atrial portal and/or pericardial portal may be constructed so as to be sufficiently rigid such that the portal does not bend substantially when inserted into other portals or when being tunneled to the body site of interest. Also, the portal(s) may comprise a material that is compatible with the other parts of the system.

Or, the atrial portal and/or pericardial portal may be fashioned to have a distal portion that can be articulated such that the distal opening can be rotated from having a configuration that is substantially straight such that the distal opening is substantially parallel with the proximal opening, to having a distal opening that is not parallel to the proximal opening of the portal. The ability to articulate may be effected by forming the end of the portal with overlapping concentric rings that can be separated from each other on one side of the portal and squeezed together on the other side of the portal. In an embodiment, the articulation may be effected proximally using a connector that can shorten one side of the portal while allowing the other side to lengthen. Or, articulation may be effected distally by pushing on a part of the distal end of the portal so as to shorten one side of the portal and lengthen the other side.

In certain embodiments, the pericardial portal or atrial portal may be fashioned to include a guide wire at its distal end. The guide wire may be made of stainless steel or other metal. The guide wire may be inserted at or near the proximal end of the portal and may extend through the portal (e.g., via a central lumen, or a lumen in the wall of the portal) to emerge at the distal end.

Also, a suction and/or infusion lumen may be incorporated into the atrial portal and/or the pericardioscopic portal. In certain embodiments, the suction lumen is an individual channel within the portal or the portal wall. The suction lumen may end with an aperture or apertures at the distal end of the portal. Or, a plurality of such suction lumens in the portal wall (e.g., one or more suction lumens surrounding, or at least partially encircling, the distal opening) may be used.

As described above, the portals of the present invention may be sized such that the atrial portal comprises a diameter less than the internal diameter of the pericardial portal. For example, the pericardial portal may comprise dimensions on the order of about 2 to 30 inches, or about 4 to 20 inches, or about 6 to 12 inches, or about 8 inches in length. Also, in alternate embodiments, the pericardial portal may have an inner diameter that ranges from about 0.15 to 3 inches, or from about 0.25 to 2.5 inches, or from about 0.35 to about 1.2 inch, or from about 0.5 to 1 inch. The atrial portal may be about the same length, but is generally smaller in diameter, having an inner diameter that ranges from e.g., from about 0.1 to 2.0 inches, or from about 0.2 to 1.5 inches, or from about 0.3 to about 1 inch, or from about 0.4 to 0.8 inches.

In yet other embodiments, the present invention comprises methods to make device that may be used with the endoscopic portals of the present invention. Such devices may be fashioned as described herein. Or, devices substantially equivalent to such devices may be fashioned.

Thus, in yet other embodiments, the present invention comprises methods to make a devices for suturing the entry location for an atrial portal (or a pressure sensor delivered by an atrial portal), or tools for performing procedures on the left or right atrium or portions of the heart accessed by the left or right atrium such as, but not limited to ablation elements, electrodes, valves, stents and the like. Also, other embodiments of the present invention comprise methods for making inner catheters/cannulas having such tools attached to the distal end with or without the inclusion of an inflatable member and associated lumen.

Depending upon the specific application, the tools/accessory devices that are made for use with a portal of the present invention may comprise a material that is flexible, such that the tool/device is able to bend, or the tool may comprise a material that is substantially rigid. Thus, in alternate embodiments, the various tools/devices may comprise a metal such as aluminum, stainless steel, spring steel, nickel titanium alloys, or other alloys. Or, the tools/accessory device may be made of plastic. For example, a resilient plastic such as vinyl, nylon, polypropylene, a polyethylene, ionomer, polyurethane, and polyethylene tetraphthalate (PET) may be used.

Each of the components used in the devices and systems (e.g., kits) of the present invention may comprise a material that may be sterilized by either chemical treatment, high temperature, and/or high pressure, exposure to sterilizing gas, or a combination of sterilization treatments as is known in the art. Also, the components of the devices and systems of the present invention may be disposable, or may be formulated to allow for cleaning, re-sterilization, and re-use.

All patents, publications and abstracts cited above are incorporated herein by reference in their entirety. It should be understood that the foregoing relates only to certain embodiments of the present invention and that numerous modifications or alterations may be made therein without departing from the spirit and the scope of the present invention as defined in the following claims.

That which is claimed is:

1. A method to access an atrium of a heart in a subject so as to perform surgical procedures upon the atrium, the method comprising:
    (a) inserting a distal end of an atrial portal into a pericardium of the subject via an incision in the pericardial sac;
    (b) manipulating a proximal end of the atrial portal to position the distal end of the atrial portal at a surface of the atrium;
    (c) determining an entry location for the atrial portal to be inserted into the atrium;
    (d) inserting the atrial portal into the atrium; and
    (e) securing the position of the atrial portal in the atrium.

2. The method of claim 1, further comprising inserting the atrial portal into a pericardial portal and positioning the distal end of the pericardial portal at the surface of the atrium.

3. The method of claim 1, wherein the atrium is the left atrium.

4. The method of claim 1, further comprising using an imaging device positioned at the distal end of the atrial portal to provides an image of body structures present near the distal end of the atrial portal.

5. The method of claim 1, further comprising providing sutures in a surface of the atrium that surround the entry location for the atrial portal and tightening the sutures around the atrial portal upon insertion of the atrial portal in the atrium to secure the atrial portal in the atrium.

6. The method of claim 1, wherein the step of inserting the atrial portal into the atrium comprises using a needle contained within the atrial portal to puncture the atrium wall.

7. The method of claim 1, wherein the step of inserting the atrial portal into the atrium comprises inserting a guide wire through a needle, and withdrawing the needle such that the guide wire is inserted into the atrium at the entry location for the atrial portal, and then threading the atrial portal over the guide wire and into the atrium.

8. The method of claim 1, wherein the step of inserting the atrial portal into the atrium comprises inserting a dilating introducer positioned at the distal end of the atrial portal into the entry location and advancing the introducer distally into the atrium wall to enlarge the opening at the entry location.

9. The method of claim 1, further comprising using a flexible cap positioned on the distal end of the atrial portal to secure the distal end of the atrial portal in the atrial wall.

10. The method of claim 1, wherein at least a portion of the cap can be expanded laterally away from the central longitudinal axis of the atrial portal.

11. The method of claim 1, further comprising inserting a tool in the atrium using the atrial portal.

12. The method of claim 11, wherein the tool comprises at least one of an ablation element, an electrode, a stent, a valve, an expandable, a debris capture device or a barbed needle.

13. The method of claim 11, wherein a cardioscopic access is via an incision in a diaphragm and via a pericardial space.

* * * * *